United States Patent
Kim et al.

(10) Patent No.: US 11,969,440 B2
(45) Date of Patent: *Apr. 30, 2024

(54) METAL (HYDR)OXIDE COMPOSITE COMPRISING POORLY SOLUBLE DRUG, METHOD FOR MANUFACTURING SAME, AND PHARMACEUTICAL COMPOSITION COMPRISING SAME

(71) Applicants: WEBIOTREE CO., LTD, Seoul (KR); CNPHARM CO., LTD., Seoul (KR)

(72) Inventors: Ho Jun Kim, Seoul (KR); Geun Woo Jin, Seoul (KR); Ki Yeok Kim, Seoul (KR)

(73) Assignees: Webiotree Co., Ltd., Seoul (KR); CNPharm Co., Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/890,796

(22) Filed: Aug. 18, 2022

(65) Prior Publication Data

US 2023/0040651 A1 Feb. 9, 2023

Related U.S. Application Data

(63) Continuation of application No. PCT/KR2021/013215, filed on Sep. 28, 2021.

(60) Provisional application No. 63/157,181, filed on Mar. 5, 2021, provisional application No. 63/153,206, filed on Feb. 24, 2021, provisional application No. 63/150,235, filed on Feb. 17, 2021, provisional application No. 63/126,717, filed on Dec. 17, 2020, provisional application No. 63/125,122, filed on Dec. 14, 2020, provisional application No. 63/085,605, filed on Sep. 30, 2020, provisional application No. 63/084,423, filed on Sep. 28, 2020.

(51) Int. Cl.
| | |
|---|---|
| *A61K 33/08* | (2006.01) |
| *A61K 31/167* | (2006.01) |
| *A61K 31/337* | (2006.01) |
| *A61P 31/14* | (2006.01) |

(52) U.S. Cl.
CPC ............ *A61K 33/08* (2013.01); *A61K 31/167* (2013.01); *A61K 31/337* (2013.01); *A61P 31/14* (2018.01)

(58) Field of Classification Search
None
See application file for complete search history.

(56) References Cited

FOREIGN PATENT DOCUMENTS

| | | | |
|---|---|---|---|
| CN | 104174028 A | | 12/2014 |
| CN | 104511027 | * | 4/2015 |
| KR | 10-2013-0035514 A | | 4/2013 |

OTHER PUBLICATIONS

Suhail et al. (Surfactants and their role in Pharmaceutical Product Development: An overview, Journal of Pharmacy and Pharmaceutics, Oct. 7, 2019). (Year: 2019).*
International Search Report for PCT/KR2021/013215 dated Dec. 31, 2021.
Tae Hyun Kim et al., "Anticancer Drug-Incorporated Layered Double Hydroxide Nanohybrids and Their Enhanced Anticancer Therapeutic Efficacy in Combination Cancer Treatment", BioMed Research International, pp. 1-11, Apr. 2014.
Xue Bi et al., "Layered Double Hydroxide-Based Nanocarriers for Drug Delivery", Pharmaceutics, 2014, pp. 298-332, vol. 6.
Jimin Xu et al., "Broad Spectrum Antiviral Agent Niclosamide and Its Therapeutic Potential", ACS Infectious Disease, 2020, pp. 909-915, vol. 6.
Goeun Choi et al., "Hydrotalcite-Niclosamide Nanohybrid as Oral Formulation towards SARS-COV-2 Viral Infections", Pharmaceuticals, 2021, pp. 1-14, 2021, vol. 14, thesis No. 486.

* cited by examiner

*Primary Examiner* — Melissa S Mercier
(74) *Attorney, Agent, or Firm* — Procopio, Cory, Hargreaves & Savitch LLP

(57) ABSTRACT

The present invention relates to a metal (hydr)oxide composite comprising a poorly soluble drug, a method for manufacturing same, and a pharmaceutical composition comprising same.

17 Claims, 47 Drawing Sheets

| PK Parameters | Niclosamide, PO | | | |
|---|---|---|---|---|
| | Yomesan | D56H | | |
| | 100 mg/kg | 100 mg/kg | 33 mg/kg | 10 mg/kg |
| AUC(last) | 2010.85 | 11599.26 | 2939.11 | 1702.92 |
| Cmax | 868.84 | 8078.23 | 2308.47 | 1542.97 |
| Tmax | 0.50 | 0.50 | 0.50 | 0.50 |
| t₁/₂ | 4.15 | 4.02 | 3.03 | 0.77 |

| PK Parameters | Niclosamide, PO | | | |
|---|---|---|---|---|
| | Yomesan | DS6H | Mg(OH)2 | MgO |
| | 100 mg/kg | 100 mg/kg | 100 mg/kg | 100 mg/kg |
| AUC(last) | 2010.85 | 11599.26 | 22437.26 | 33797.23 |
| Cmax | 868.84 | 8078.23 | 17828.61 | 21438.78 |
| Tmax | 0.50 | 0.50 | 0.50 | 0.50 |
| t½ | 4.15 | 4.02 | 2.67 | 2.37 |

| PK Parameters | Niclosamide, PO | | | |
|---|---|---|---|---|
| | Yomesan | DS6H | Mg(OH)2 | MgO |
| | 100 mg/kg | 100 mg/kg | 100 mg/kg | 100 mg/kg |
| AUC(last) | 2010.85 | 11599.26 | 22437.26 | 33797.23 |
| Cmax | 868.84 | 8078.23 | 17828.61 | 21438.78 |
| Tmax | 0.50 | 0.50 | 0.50 | 0.50 |
| $t_{1/2}$ | 4.15 | 4.02 | 2.57 | 2.37 |

METAL (HYDR)OXIDE COMPOSITE COMPRISING POORLY SOLUBLE DRUG, METHOD FOR MANUFACTURING SAME, AND PHARMACEUTICAL COMPOSITION COMPRISING SAME

CROSS-REFERENCE TO RELATED APPLICATIONS

This application is a Bypass Continuation of PCT International Application No. PCT/KR2021/013215 filed on Sep. 28, 2021, which is based on and claims priority to U.S. Patent Application No. 63/084,423 filed on Sep. 28, 2020, U.S. Patent Application No. 63/085,605 filed on Sep. 30, 2020, U.S. Patent Application No. 63/125,122 filed on Dec. 14, 2020, U.S. Patent Application No. 63/126,717 filed on Dec. 17, 2020, U.S. Patent Application No. 63/150,235 filed on Feb. 17, 2021, U.S. Patent Application No. 63/153,206 filed on Feb. 24, 2021, U.S. Patent Application No. 63/157,181 filed on Mar. 5, 2021, and PCT International Application No. PCT/KR2021/005208 filed on Apr. 23, 2021, the disclosures of which are incorporated herein by reference in their entireties.

TECHNICAL FIELD

The present invention relates to a metal (hydr)oxide composite comprising a poorly soluble drug having an effect of improving dispersibility of the poorly soluble drug and making its bioavailability excellent, a method for manufacturing same, and a pharmaceutical composition comprising same.

BACKGROUND ART

As the human lifespan is extended due to the development of technology, aging of the population is deepening in countries around the world. As the aging of the population deepens, the number of patients suffering from diseases caused by viruses and diseases caused by cancer has also increased, as well as diseases caused by living environment, eating habits, and stress are also on the rise. Accordingly, a number of drugs that are effective in antiviral agents, anti-inflammatory agents, anticancer agents, etc. have been developed, but the drugs have limitations in their application due to poor solubility, and thus improvement of solubility and improvement of bioavailability of the developed drugs have been implemented as major tasks in drug development.

In addition, due to the recent epidemic of COVID-19, the development of therapeutic agent is urgently required. However, the reality is that it is difficult to develop an appropriate therapeutic agent at the necessary time because it takes a huge amount of time to develop a new drug. Accordingly, studies are being conducted to recreate previously used drugs as antiviral agents, and these studies use the so-called "drug repositioning" method. Conventionally, drugs such as Niclosamide and Ciclesonide as therapeutic candidates for COVID-19 have been studied as therapeutic agents for COVID-19, and as anticancer drugs, docetaxel is being studied as a strong therapeutic candidate for COVID-19. Niclosamide and Ciclesonide are drugs, each of which has been approved for development as anti-parasitic agents, anti-inflammatory agents, and anti-malarial agents and is already on the market, and docetaxel has been approved for development as an anticancer agent and is already on the market. These drugs have already been verified for safety and have the advantage of being able to mass-produce, but since these drugs are poorly soluble drugs, their dissolution rate in the body is remarkably reduced, and thus there was a problem in that it was difficult to exert an appropriate effect as a COVID-19 therapeutic agent and an anticancer agent in the state of a commercially available pharmaceutical.

In the case of the poorly soluble drug as described above, in order to maximize the action as the antiviral and/or anticancer agent in the body, dispersibility has to be improved, and bioavailability can be increased only by solving the problem of being able to maintain a high concentration in blood.

However, until now, there has been a problem that bioavailability could not be effectively increased in studies to recreate the above drugs. In addition, in the case of a conventional method for increasing dispersibility of poorly soluble drugs, there is a method using a dispersing agent such as a water-soluble polymer carrier, as in Korean Patent Registration No. 10-1897995, but there has been a problem in that solubility and dispersibility of the poorly soluble drug cannot be increased to the extent that dispersibility of the poorly soluble drug can be used in vivo by simply using the dispersing agent as in the method described above.

PATENT LITERATURE

Korean Patent Registration No. 10-1897995

DISCLOSURE OF THE INVENTION

Technical Problem

The present invention aims to provide a metal (hydr)oxide composite which contains a poorly soluble drug and has an excellent bioavailability effect by improving the problem of poor dispersibility and poor blood concentration retention of the poorly soluble drug.

In addition, the present invention aims to provide a method for preparing the metal (hydr)oxide composite.

In addition, the present invention aims to provide a pharmaceutical composition containing the metal (hydr)oxide composite which has excellent bioavailability described above.

Technical Solution

The present invention provides a metal (hydr)oxide composite comprising: a metal (hydr)oxide; and a compound containing at least one or more hydroxyl groups in the compound or a salt thereof, wherein the metal (hydr)oxide is one or more selected from the compounds represented by Chemical Formulas 3 to 5 below.

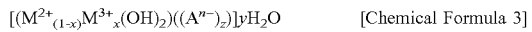
[Chemical Formula 3]

(In Chemical Formula 3, $M^{2+}$ is a divalent metal cation selected from the group consisting of $Mg^{2+}$, $Ni^{2+}$, $Cu^{2+}$, $Co^{2+}$, and $Zn^{2+}$, $M^{3+}$ is a trivalent metal cation selected from the group consisting of $Al^{3+}$, $Fe^{3+}$, $V^{3+}$, $Ti^{3+}$, $Mn^{3+}$, and $Ga^{3+}$, x is a number having a range of greater than 0 and less than or equal to 0.5, A is an anion selected from the group consisting of $CO_3^{2-}$, $NO_3^-$, $Br^-$, $Cl^-$, $SO_4^{2-}$, $HPO_4^{2-}$, and $F^-$, n is a charge number of the anion A, n is a number having a range of 0.5 or more and 2 or less, z is a number having a range of 0 or more and 1 or less, and y is a positive number greater than 0.)

$$[(M^{2+}(OH)_{2-x})((A^{n-})_z)]yH_2O \quad \text{[Chemical Formula 4]}$$

(In Chemical Formula 4, $M^{2+}$ is a divalent metal cation selected from the group consisting of $Mg^{2+}$, $Ni^{2+}$, $Cu^{2+}$, $Co^{2+}$, and $Zn^{2+}$, x is a number having a range of 0 or more and 0.4 or less, A is an anion selected from the group consisting of $CO_3^{2-}$, $NO_3^-$, $Br^-$, $Cl^-$, $SO_4^{2-}$, $HPO_4^{2-}$, and $F^-$, n is a charge number of anion A, n is a number having a range of 0 or more and 2 or less, z is a number having a range of 0 or more and 1 or less, and y is a positive number greater than 0.)

$$[(M^{2+}(O)_{2-x})((A^{n-})_z)]yH_2O \quad \text{[Chemical Formula 5]}$$

(In Chemical Formula 5, $M^{2+}$ is $Mg^{2+}$, $Ni^{2+}$, $Cu^{2+}$, or $Zn^{2+}$, x is a number of 1 or more and less than 2, A is an anion selected from the group consisting of $CO_3^{2-}$, $NO_3^-$, $Br^-$, $Cl^-$, $SO_4^{2-}$, $HPO_4^{2-}$, and $F^-$, n is a charge number of the anion A, n is a number having a range of 0 or more and 2 or less, z is a number having a range of 0 or more and 1 or less, and y is a positive number greater than 0.)

In addition, the present invention provides a pharmaceutical composition comprising: a metal (hydr)oxide; a compound containing at least one or more hydroxyl groups in the compound or a salt thereof; and an additive, wherein the metal (hydr)oxide is one or more among the compounds represented by Chemical Formulas 3 to 5 below.

$$[(M^{2+}_{(1-x)}M^{3+}_x(OH)_2)((A^{n-})_z)]yH_2O \quad \text{[Chemical Formula 3]}$$

(In Chemical Formula 3, $M^{2+}$ is a divalent metal cation selected from the group consisting of $Mg^{2+}$, $Ni^{2+}$, $Cu^{2+}$, $Co^{2+}$, and $Zn^{2+}$, $M^{3+}$ is a trivalent metal cation selected from the group consisting of $Al^{3+}$, $Fe^{3+}$, $V^{3+}$, $Ti^{3+}$, $Mn^{3+}$, and $Ga^{3+}$, x is a number having a range of greater than 0 and less than or equal to 0.5, A is an anion selected from the group consisting of $CO_3^{2-}$, $NO_3^-$, $Br^-$, $Cl^-$, $SO_4^{2-}$, $HPO_4^{2-}$, and $F^-$, n is a charge number of the anion A, n is a number having a range of 0.5 or more and 2 or less, z is a number having a range of 0 or more and 1 or less, and y is a positive number greater than 0.)

$$[(M^{2+}(OH)_{2-x})((A^{n-})_z)]yH_2O \quad \text{[Chemical Formula 4]}$$

(In Chemical Formula 4, $M^{2+}$ is a divalent metal cation selected from the group consisting of $Mg^{2+}$, $Ni^{2+}$, $Cu^{2+}$, $Co^{2+}$, and $Zn^{2+}$, x is a number having a range of 0 or more and 0.4 or less, A is an anion selected from the group consisting of $CO_3^{2-}$, $NO_3$, $Br^-$, $Cl^-$, $SO_4^{2-}$, $HPO_4^{2-}$, and $F^-$, n is a charge number of anion A, n is a number having a range of 0 or more and 2 or less, z is a number having a range of 0 or more and 1 or less, and y is a positive number greater than 0.)

$$[(M^{2+}(O)_{2-x})((A^{n-})_z)]yH_2O \quad \text{[Chemical Formula 5]}$$

(In Chemical Formula 5, $M^{2+}$ is $Mg^{2+}$, $Ni^{2+}$, $Cu^{2+}$, or $Zn^{2+}$, x is a number of 1 or more and less than 2, A is an anion, n is a charge number of the anion A, n is a number having a range of 0 or more and 2 or less, z is a number having a range of 0 or more and 1 or less, and y is a positive number greater than 0.)

Advantageous Effects

The present invention has an effect of capable of providing a metal (hydr)oxide composite which contains a poorly soluble drug or a prodrug thereof and has excellent bioavailability by improving a low blood concentration retention effect and low dispersibility of the poorly soluble drug, which are problems of the poorly soluble drug, by using the metal (hydr)oxide composite.

The present invention has an effect of providing a method for preparing a metal (hydr)oxide composite capable of improving the low dispersibility and low blood dissolution effect of the poorly soluble drug.

In addition, when the calcined metal (hydr)oxide composite of the present invention is used, the present invention can also have an effect of increasing bioavailability by protecting not only a poorly soluble drug but also drugs that are easily decomposed in vivo.

MODE FOR CARRYING OUT THE INVENTION

Figure 1:
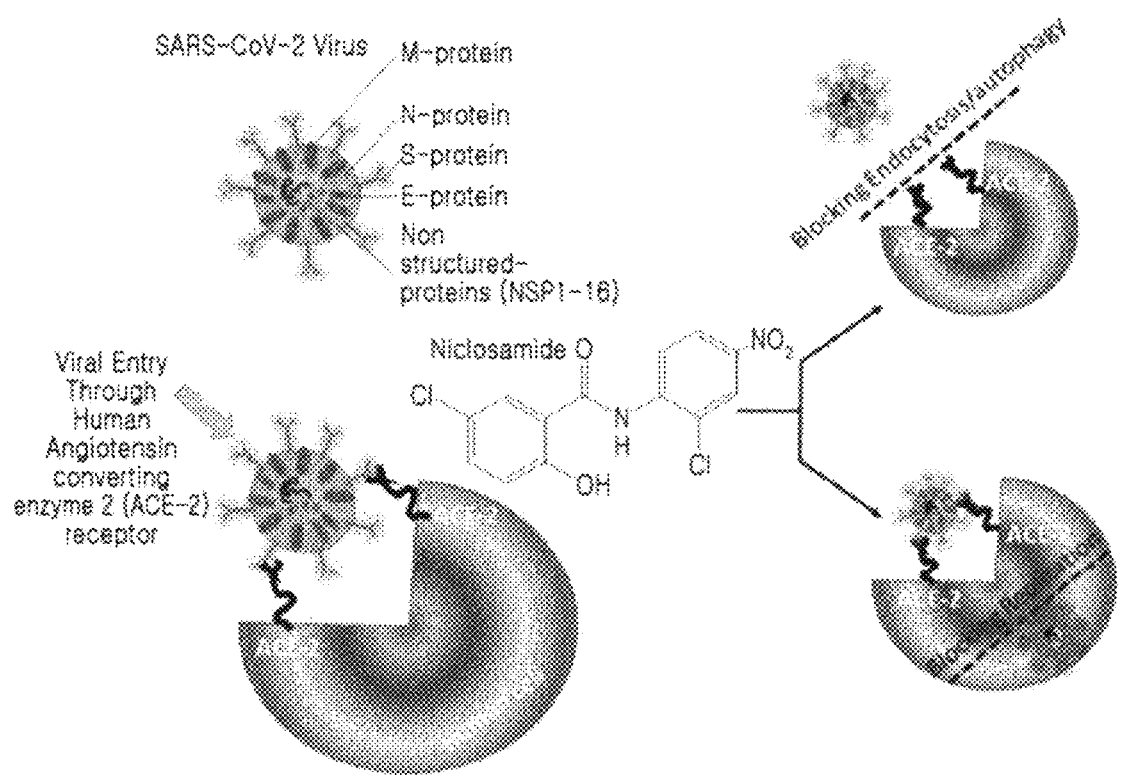
FIG. 1 is a schematic diagram of an antiviral mechanism of niclosamide against a SARS-CoV-2 virus.
Figure 2:
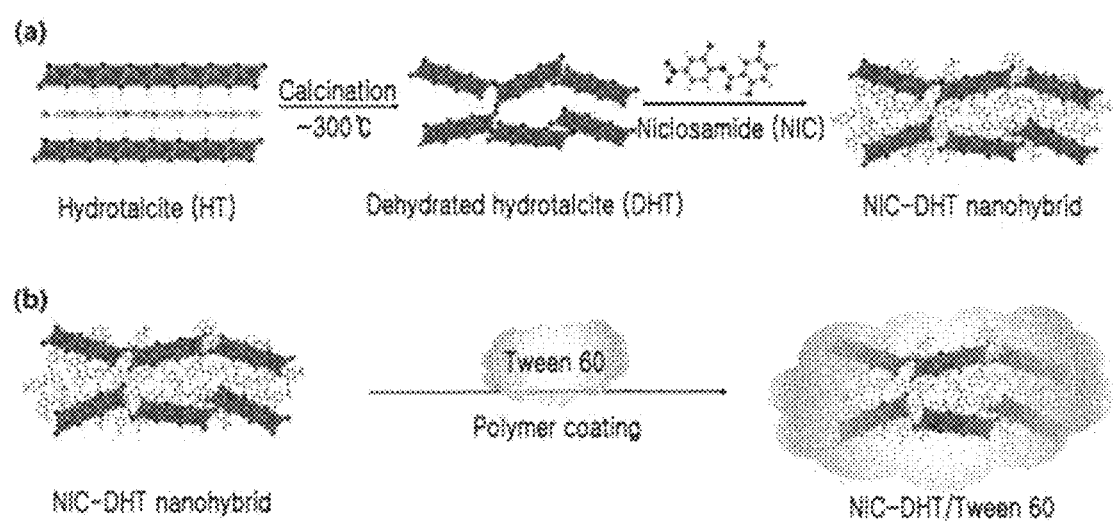
In FIG. 2, (a) is a schematic diagram of a method for preparing a DHT-NIC composite, and (b) is a method for preparing a composition obtained by treating the DHT-NIC composite with a surfactant.

Hereinafter, the present invention will be described more specifically.

The present invention provides a metal (hydr)oxide composite containing a poorly soluble drug with significantly improved dispersibility, solubility, and bioavailability. In the present invention, the poorly soluble drug is a drug having significantly low solubility in water, and means a compound containing at least one or more hydroxyl groups in the compound. The significantly low solubility in water of the compound may mean that the compound has a solubility in water of less than 0.01 mM.

The present invention provides a metal (hydr)oxide composite comprising: a metal (hydr)oxide; and a compound comprising one or more hydroxyl groups in the compound or a salt thereof, wherein the metal (hydr)oxide is one or more selected from the compounds represented by Chemical Formulas 3 to 5 below.

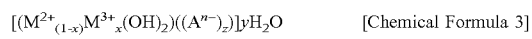

[Chemical Formula 3]

(In Chemical Formula 3, $M^{2+}$ is a divalent metal cation selected from the group consisting of $Mg^{2+}$, $Ni^{2+}$, $Cu^{2+}$, $Co^{2+}$, and $Zn^{2+}$, $M^{3+}$ is a trivalent metal cation selected from the group consisting of $Al^{3+}$, $Fe^{3+}$, $V^{3+}$, $Ti^{3+}$, $Mn^{3+}$, and $Ga^{3+}$, x is a number having a range of greater than 0 and less than or equal to 0.5, A is an anion selected from the group consisting of $CO_3^{2-}$, $NO_3^-$, $Br^-$, $Cl^-$, $SO_4^{2-}$, $HPO_4^{2-}$, and $F^-$, n is a charge number of the anion A, n is a number having a range of 0.5 or more and 2 or less, z is a number having a range of 0 or more and 1 or less, and y is a positive number greater than 0.)

[Chemical Formula 4]

(In Chemical Formula 4, $M^{2+}$ is a divalent metal cation selected from the group consisting of $Mg^{2+}$, $Ni^{2+}$, $Cu^{2+}$, $Co^{2+}$, and $Zn^{2+}$, x is a number having a range of 0 or more and 0.4 or less, A is an anion selected from the group consisting of $CO_3^{2-}$, $NO_3^-$, $Br^-$, $Cl^-$, $SO_4^{2-}$, $HPO_4^{2-}$, and $F^-$, n is a charge number of the anion A,
n is a number having a range of 0 or more and 2 or less,
z is a number having a range of 0 or more and 1 or less, and
y is a positive number greater than 0.)

$$[(M^{2+}(O)_{2-x})((A^{n-})_z)]yH_2O \quad \text{[Chemical Formula 5]}$$

(In Chemical Formula 5,
$M^{2+}$ is $Mg^{2+}$, $Ni^{2+}$, $Cu^{2+}$, or $Zn^{2+}$,
x is a number of 1 or more and less than 2,
A is an anion selected from the group consisting of $CO_3^{2-}$, $NO_3^-$, $Br^-$, $Cl^-$, $SO_4^{2-}$, $HPO_4^{2-}$, and $F^-$,
n is a charge number of the anion A,
n is a number having a range of 0 or more and 2 or less,
z is a number having a range of 0 or more and 1 or less, and
y is a positive number greater than 0.)

In the present invention, the metal (hydr)oxide refers to a metal oxide or a metal hydroxide together, and in Formulas 3 to 5, y that means the number of water molecules, may be a positive number greater than 0, and may be in a range of greater than 0 and less than or equal to 20.

The metal (hydr)oxide composite of the present invention may be represented by Chemical Formulas 6 to 8 below.

$$[(M^{2+}(O)_{2-x})((A^{n-})z)][Q]yH_2O \quad \text{[Chemical Formula 6]}$$

(In Chemical Formula 6,
$M^{2+}$ is a divalent metal cation selected from the group consisting of $Mg^{2+}$, $Ni^{2+}$, $Cu^{2+}$, $Co^{2+}$, and $Zn^{2+}$,
x is a number having a range of 1 or more and 2 or less,
A is an anion selected from the group consisting of $CO_3^{2-}$, $NO_3^-$, $Br^-$, $Cl^-$, $SO_4^{2-}$, $HPO_4^{2-}$, and $F^-$,
Q is a compound containing at least one or more hydroxyl groups in the compound, or a salt thereof,
n is a charge number of the anion A,
n is a number having a range of 0 or more and 2 or less,
z is a number having a range of 0 or more and 1 or less, and
y is a positive number greater than 0.)

$$[(M^{2+}(OH)_x(O)_y)][Q]zH_2O \quad \text{[Chemical Formula 7]}$$

(In Chemical Formula 7,
$M^{2+}$ is a divalent metal cation selected from the group consisting of $Mg^{2+}$, $Ni^{2+}$, $Cu^{2+}$, $Co^{2+}$, and $Zn^{2+}$,
Q is a compound containing at least one or more hydroxyl groups in the compound, or a salt thereof,
x is a number having a range of 0 or more and 2 or less,
y is a number having a range of 0 or more and 1 or less,
x+y is not greater than 3,
x and y do not have a value of 0 at the same time, and
z is a number having a range of 0 or more and 10 or less.)

$$[(M^{2+}(OH)_{2-x})((A^{n-})_z)][Q]yH_2O \quad \text{[Chemical Formula 8]}$$

(In Chemical Formula 8,
$M^{2+}$ is a divalent metal cation selected from the group consisting of $Mg^{2+}$, $Ni^{2+}$, $Cu^{2+}$, $Co^{2+}$, and $Zn^{2+}$,
x is a number having a range of 0 or more and 0.4 or less,
A is an anion selected from the group consisting of $CO_3^{2-}$, $NO_3^-$, $Br^-$, $Cl^-$, $SO_4^{2-}$, $HPO_4^{2-}$, and $F^-$,
Q is a compound containing at least one or more hydroxyl groups in the compound, or a salt thereof,
n is a charge number of the anion A,
n is a number having a range of 0 or more and 2 or less,
z is a number having a range of 0 or more and 1 or less, and
y is a positive number greater than 0.)

In Formulas 6 to 8, y means the number of water molecules, is a positive number greater than 0, and may have a range of greater than 0 and less than or equal to 20.

In the present invention, the compound containing at least one or more hydroxyl groups in the compound and having a solubility in water of less than 0.01 mM may particularly include niclosamide, loperamide, penfluridol, ciclesonide, oxyclozanide, dihydrogambogic acid, osajin, lusutrombopag, isoosajin, ivacaftor, triparanol, droloxifene, lopinavir, Docetaxel, Vitamin A, idebenone, Paclitaxel, Fulvestrant, probucol, doxorubicin, gemcitabine, quercetin, cyanidin, delphinidin, malvidin, pelargonidin, petunidin, curcumin, epigallocatechin-3-gallate, genistein, resveratrol, estradiol, camptothecin, podophyllotoxin, raloxifene, topotecan, bortezomib, netilmicin, branaplam, spiramycin, etc.

The compound containing at least one or more hydroxyl groups in the compound may have a solubility in water of less than 0.01 mM. Specifically, the compound having a solubility in water of less than 0.01 mM among the compounds containing at least one or more hydroxyl groups in the compound may be niclosamide, loperamide, penfluridol, ciclesonide, oxyclozanide, dihydrogambogic acid, osajin, lusutrombopag, isoosajin, ivacaftor, triparanol, droloxifene, lopinavir, Docetaxel, vitamin A, idebenone, Paclitaxel, Fulvestrant, probucol, etc.

The compound having a solubility in water of less than 0.01 mM and containing one or more hydroxyl groups, or a salt thereof may more preferably be one or more selected from the compounds represented by Chemical Formula 1 or Chemical Formula 2 below.

[Chemical Formula 1]

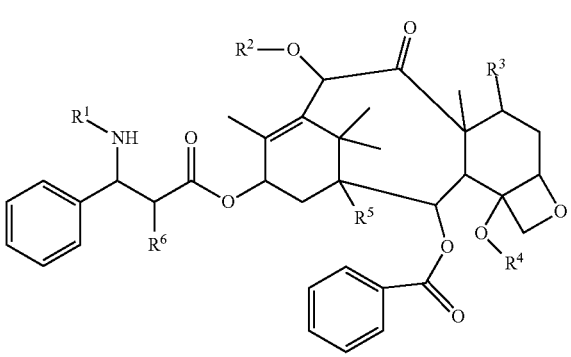

(In Chemical Formula 1,
R1 to R6 are each independently a hydrogen atom, a halogen atom, a hydroxyl group, an alkoxy group, an ester group, an acyl group, an aromatic ring or a nitro group, and
at least one or more among R1 to R6 are hydroxyl groups.)

[Chemical Formula 2]

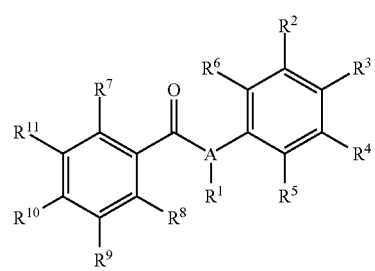

(In Chemical Formula 2,
A is a nitrogen atom or an oxygen atom,
if A is a nitrogen atom, R1 may be a hydrogen atom, a halogen atom, a hydroxyl group, or an alkyl group, and, if A is an oxygen atom, R1 does not have a substituent, R2 to R11 are each independently a hydrogen atom, a halogen atom, a hydroxyl group, an alkoxy group, an ester group, an acyl group, an aromatic ring or a nitro group, and
at least one or more among R1 to R11 are hydroxyl groups.)

In the substituent of Chemical Formula 1 or Chemical Formula 2, the halogen atom means a fluorine atom (F), a chlorine atom (Cl), a bromine atom (Br) or an iodine atom (I), In addition, the alkyl group may be a saturated hydrocarbon of 1 to 10 carbon number or an unsaturated hydrocarbon of 1 to 10 carbon number, and the saturated hydrocarbon of 1 to 10 carbon number may include a methyl group, an ethyl group, a propyl group, an isopropyl group, a butyl group, etc. In the substituent of Chemical Formula 1 or Chemical Formula 2, the alkoxy group may be a methoxy group, an ethoxy group, a propoxy group, a butoxy group, etc., the acyl group may be a formyl group, an acetyl group (ethanoyl group), a benzoyl group, etc., and the aromatic ring may be an aromatic ring of 3 to 20 carbon number.

The compound represented by Chemical Formula 1 may more particularly be one or more compounds selected from Docetaxel, and Paclitaxel.

The compound represented by Chemical Formula 2 may more particularly be niclosamide.

In the present invention, the drug forming a composite with a metal oxide or a metal hydroxide to increase bioavailability may be a compound having a solubility in water of less than 0.01 and containing at least one or more hydroxyl groups (OH) in the structure of the compound. It was confirmed that in the case of a compound having high solubility in water, though forming a composite using a metal oxide or hydroxide, the increasing effect of bioavailability may not always show up, and in the case of a compound having low solubility in water but excluding a hydroxyl group, the reactivity with a metal oxide and/or a metal hydroxide is reduced during the forming process with the metal oxide or metal hydroxide, and the increasing effect of the solubility of the drug is difficult to obtain, and the increasing effect of bioavailability is not shown, either.

Among the metal oxide and metal hydroxide of the present invention, the most preferable for increasing the bioavailability of the compound, the salt thereof and/or the drug, is a composite with a magnesium oxide (MgO) type.

In addition, the present invention may provide a pharmaceutical composition comprising: a metal (hydr)oxide; a compound containing at least one or more hydroxyl groups in the compound or a salt thereof; and an additive, wherein
the metal hydr(oxide) is one or more among the compounds represented by Chemical Formula 3 to Chemical Formula 5 above.

In addition, the present invention provides a preparing method comprising a step of mechanochemically synthesizing a metal (hydr)oxide powder and a poorly soluble drug powder to form a metal (hydr)oxide composite.

Further, the present invention provides a preparing method comprising a step of mechanochemically synthesizing a metal (hydr)oxide powder and a poorly soluble drug powder. The mechanochemically synthesizing step means a method of grinding or milling powders by applying a physical force, and can be used without limitation as long as it is a method commonly used in the field to which the present invention belongs. More specifically, grinding and/or milling synthesis may be used for mechanochemical synthesis for a solid-state reaction. More specifically, milling synthesis method includes Grinding mill, Mortar Grinder, Ball mill, Bead mill, Roller mill, Mix&Heat, and super-fine grinding mill, Attrition mill, etc., and through these methods, a particle size of the powder material can be reduced, and the effect of grinding, dispersing, and mixing can be obtained. When including the step of mechanochemically synthesizing as described above, it is preferable in that it has the advantages of the low preparation cost and less waste after preparing, as well as minimizing recovery of the metal (hydr)oxide calcined by the solvent-free preparation method to the metal (hydr)oxide state before calcination.

In addition, the present invention can provide a pharmaceutical composition prepared by physically grinding a metal (hydr)oxide powder, a poorly soluble drug powder, and a surfactant powder.

If the metal (hydr)oxide is calcined, the temperature conditions for calcining the metal (hydr)oxide in the present invention can be in the range of 200 to 850° C. More specifically, when the material to be calcined is hydrotalcite, it can be calcined in the range of 200 to 800° C. When a material to be calcined is a metal hydroxide, for example, $Mg(OH)_2$, it may be preferable to perform calcination in the temperature range of 200 to 300° C.

Meanwhile, in the case of a metal oxide, for example, MgO, the solubility or bioavailability may be effectively increased by forming a composite with a compound containing at least one or more hydroxyl groups in the compound and/or a drug.

An embodiment of the present invention is characterized by making the poorly soluble drug to be contained in the form of calcined metal (hydr)oxide. Since the structure (e.g., DHT) of the calcined metal (hydr)oxide has a wider surface area capable of containing the poorly soluble drug niclosamide than the structure (e.g., HT) of the uncalcined metal (hydr)oxide, the solubility and dispersibility of the poorly soluble drug can be further improved.

In the present invention, the anhydrous organic solvent may be used without limitation as long as it is an organic solvent that does not contain water, but more specifically, may be anhydrous alcohol, acetone, acetonitrile, dichloromethane, tetrahydrofuran, chloroform, etc. In addition, the anhydrous alcohol may be anhydrous ethanol, anhydrous methanol, anhydrous butanol, etc.

In addition, the present invention provides a metal (hydr)oxide composite which contains a poorly soluble drug or a prodrug thereof and is prepared by a preparing method including a step of preparing a calcined metal (hydr)oxide by calcining the metal (hydr)oxide) and a step of reacting the calcined metal (hydroxide) oxide with the poorly soluble drug or the prodrug thereof in an anhydrous organic solvent.

The step of the reacting is characterized in that the hydration reaction is minimized to minimize the recovery of the calcined metal (hydroxide) oxide to the form before the calcination.

When the metal (hydr)oxide composite is prepared by the method described above, the metal (hydr)oxide composite may contain a metal (hydr)oxide in a calcined form. Specifically, when the poorly soluble drug is contained in the metal (hydr)oxide in the calcined form, and the poorly soluble drug reacts with the metal (hydr)oxide in the calcined form to form a metal (hydr)oxide composite, it is preferable in that it can excellently increase the dispersibility and solubility of the poorly soluble drug, thereby capable of having the effect of increasing the bioavailability of the poorly soluble drug.

In addition, the present invention may provide a pharmaceutical composition prepared by physically grinding a metal (hydr)oxide powder, a poorly soluble drug powder and a surfactant powder.

In the present invention, the anhydrous organic solvent may be used without limitation as long as it is an organic solvent that does not contain water, but more specifically, may be anhydrous alcohol, acetone, acetonitrile, dichloromethane, tetrahydrofuran, chloroform, etc. In addition, the anhydrous alcohol may be anhydrous ethanol, anhydrous methanol, anhydrous butanol, etc.

In addition, the present invention provides a metal (hydr)oxide composite containing a poorly soluble drug or a prodrug thereof, by the preparing method including a step of reacting a metal (hydr)oxide and a poorly soluble drug or a prodrug thereof in an anhydrous organic solvent.

In the reacting step, it is characterized in that hydration reaction is minimized, and the recovery of the calcined type metal (hydr)oxide to a type before the calcination is minimized.

If prepared by the above-described method, the metal (hydr)oxide composite may include a metal (hydr)oxide in a calcined form. Specifically, if a poorly soluble drug is included in the metal (hydr)oxide in a calcined form, and the poorly soluble drug reacts with the metal (hydr)oxide in a calcined form to form a metal (hydr)oxide composite afterward, it is preferable in that the dispersibility and solubility of the poorly soluble drug may increase excellently, and accordingly, increasing effect of the bioavailability of the poorly soluble drug may be achieved.

Also, the present invention provides a pharmaceutical composition comprising a metal (hydr)oxide composite comprising a metal (hydr)oxide and a compound containing at least one or more hydroxyl groups in the compound or a salt thereof; and an additive.

The pharmaceutical composition may include 10 to 60 wt % of the metal (hydr)oxide, 0.1 to 60 wt % of the compound or a salt thereof, and 10 to 85 wt % of the additive, and more preferably, include 10 to 40 wt % of the compound or a salt thereof, 10 to 45 wt % of the metal (hydr)oxide, and 10 to 80 wt % of the additive, based on total 100 wt % of the pharmaceutical composition.

In addition to the above-description, the metal (hydr)oxide and the compound containing at least one or more hydroxyl groups in the compound or a salt thereof may be included in a ratio of 1:0.1 to 10.

The metal (hydr)oxide composite contained in the pharmaceutical composition may be represented by one or more selected from Chemical Formulas 6 to 8 below.

  [Chemical Formula 6]

(In Chemical Formula 6, $M^{2+}$ is a divalent metal cation selected from the group consisting of $Mg^{2+}$, $Ni^{2+}$, $Cu^{2+}$, $Co^{2+}$, and $Zn^{2+}$, x is a number having a range of 1 or more and 2 or less, A is an anion selected from the group consisting of $CO_3^{2-}$, $NO_3^-$, $Br^-$, $Cl^-$, $SO_4^{2-}$, $HPO_4^{2-}$, and $F^-$, Q is a compound containing at least one or more hydroxyl groups in the compound, n is a charge number of the anion A, n is a number having a range of 0 or more and 2 or less, z is a number having a range of 0 or more and 1 or less, and y is a positive number greater than 0.)

  [Chemical Formula 7]

(In Chemical Formula 7, $M^{2+}$ is a divalent metal cation selected from the group consisting of $Mg^{2+}$, $Ni^{2+}$, $Cu^{2+}$, $Co^{2+}$, and $Zn^{2+}$, Q is a compound containing at least one or more hydroxyl groups in the compound, x is a number having a range of 0 or more and 2 or less, y is a number having a range of 0 or more and 1 or less, x+y is not greater than 3, x and y do not have a value of 0 at the same time, and z is a number having a range of 0 or more and 10 or less.)

  [Chemical Formula 8]

(In Chemical Formula 8, $M^{2+}$ is a divalent metal cation selected from the group consisting of $Mg^{2+}$, $Ni^{2+}$, $Cu^{2+}$, $Co^{2+}$, and $Zn^{2+}$, x is a number having a range of 0 or more and 0.4 or less, A is an anion selected from the group consisting of $CO_3^{2-}$, $NO_3^-$, $Br^-$, $Cl^-$, $SO_4^{2-}$, $HPO_4^{2-}$, and $F^-$, Q is a compound containing at least one or more hydroxyl groups in the compound, n is a charge number of the anion A, n is a number having a range of 0 or more and 2 or less, z is a number having a range of 0 or more and 1 or less, and y is a positive number greater than 0.)

In addition, the pharmaceutical composition may be administered at 0.1 to 500 mg/Kg.

In the present invention, the additive may be most preferably a surfactant, and the surfactant may be a cellulose-based surfactant, polyoxyethylene sorbitan fatty acid ester-based surfactant, poloxamer-based surfactant, lecithin-based surfactant, glycerol fatty acid ester-based surfactant, sorbitan fatty acid ester-based surfactant, PEG-based surfactant, Long chain of sugar, Gum-based surfactant, Gelling agent-based surfactant, thickening polysaccharide-based surfactant, sodium dodecyl sulfate, etc. Specifically, the cellulose-based surfactant may be hydroxypropyl methylcellulose (HPMC), hydroxyethyl cellulose, hydroxypropyl cellulose (HPC), carboxymethyl cellulose (CMC), ethyl cellulose (EC), cellulose acetate (CA), etc., but HPMC may be most preferred. In the case of the polyoxyethylene sorbitan fatty acid ester-based surfactant, commercially available Tween-based surfactants are the most representative, and it takes a form in which fatty acid and ethylene oxide are ester-bonded. The polyoxyethylene sorbitan fatty acid ester-based surfactant may be polyoxyethylene sorbitan monolaurate (Tween 20), polyoxyethylene sorbitan monopalmitate (Tween 40), polyoxyethylene glycol sorbitan monostearate (Tween 60), Tween 65, polyoxyethylene sorbitan monooleate (Tween 80), polyoxyethylene sorbitan trioleate (Tween 85), etc. The lecithin-based surfactant is a substance for lecithin and its derivatives, and may be phospholipids, phosphatidyl choline, mixed phospholipids, sodium cholate, hydroxylated phospholipids, hydroxylated lecithin, etc. The glycerol fatty acid ester-based surfactant may be polyglycerol fatty acid esters, polyglycerol polyricinoleate, polyoxyethyleneglycerol triricinoleate, cremophor EL, etc. The sorbitan fatty acid ester-based surfactant may be sorbitan monolaurate (Span 20), sorbitan monooleate (Span 80), etc. The PEG-based surfactant may be PEG 200, PEG 300, PEG 400, PEG 500, PEG 1000, PEG 1500, mPEG 550, etc. The poloxamer-based surfactant may be poloxamer 101, poloxamer 105, poloxamer 108, poloxamer 122, poloxamer 123, poloxamer 124, poloxamer 181, poloxamer 182, poloxamer 183, poloxamer 184, poloxamer 185, poloxamer 188, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, poloxamer 334, poloxamer 335, poloxamer 338, poloxamer 401, poloxamer 402, poloxamer 403, poloxamer 407, etc. The Long chain of sugar, Gum-based surfactant, Gelling agent-based surfactant and thickening polysaccharide-based surfactant may specifically be Microfibrous cellulose, carboxy methyl cellulose (CMC), nitrocellulose, Hydroxypropyl guar, Modified starches, Xanthan Gum, gelatin, Guar Gum, Gum Arabic, Cellulose Gum, Locust Bean Gum, Tamarind Gum, Tara Gum, glucomannan, Polyquart, Carbopol pre-gel, Hycel, polystearate, alginate, carrageenan, agar, Furcellaran, Gum tracanth, Karaya gum, Gellan gum, Rhamsan gum, Welan gum, Quince seed Gum, Dextran, hyaluronic acid, Carbopol 941, Carbopol 934, Carbopol 940, cationic polymer (Polyquaternium-10), Polyvinyl alcohol, medium-chain fatty acid, and fumaric stearate. If such surfactants are used, the solubility and dispersibility of a metal (hydr)oxide composite containing a poorly soluble drug may be improved, and accordingly, it could be preferable in that the bioavailability of the poorly soluble drug may be increased.

In addition, the pharmaceutical composition according to the present invention may further include without limitation any additives commonly used in the field to which the present invention belongs, in addition to the additives described above, and the type thereof is not limited. More specifically, the additive may be a plasticizer added to the resin to impart flexibility and workability, a pH adjuster for adjusting the pharmaceutical composition to an appropriate acidity level for use as a formulation, an excipient, a solubilizing agent to increase the solubility of substances in semi-solid and solid phases, a sweetener agent, a gelling agent, a bonding agent to adsorb, solidify, and impart consistency to the mixture (moisture absorption at high temperatures), a hard capsule base, a hardener, a surfactant other than cellulose-based and Tween-based surfactants described above, an anticaking agent used to absorb moisture or prevent solidification, a brightener, a flavors enhancer for maximizing or tuning the original taste and aroma, a base of an inactive ingredient that can be used as a vehicle for an active drug, a porous agent that forms a structure with many small gaps through rapid evaporation by rapid heating, a sugar coating agent, a bulking agent for freeze-drying, an isotonic agent, a liner, a hair softener, a matting agent, a pain relieving component, a semi-permeable film that protects the adhesive side of the adhesive tape and serves as paper that can be easily peeled off during use, an effervescent agent, an antiseptic, a radioprotective agent, a desiccant, a release-modifying agent, a culture medium, a denaturant, an antimicrobial preservative, an anti-adherent, an aerosol propellant that is gas liquefied at 40.6° C. with a vapor pressure greater than 14.7 lb/sq, a dispersing agent, an opacifying agent, a disintegrant, an acidifying agent which is a substance that removes electrons, an oxidizer, an osmotic regulator that controls the release rate of a drug using the principle of osmotic pressure, a sustained release modifying agent, a cleanser, an antifoaming agent, a humectant, a stabilizing agent, an alkalizing agent, a mattress for storing drug storage layer drugs, a soft capsule base, an emollient which is a cream-like substance that softens the skin, a buffering agent that prevents large changes in the hydrogen ion index, a solvent, an emulsifying agent, a carrying agent used for the binding or application of active medicinal products, a plasticizer, a softener, an emulsifier, a blood coagulation inhibitor, an anti-allergenic, an enteric coating agent, a viscosity-increasing agent, a complexing agent, an adhesive support adhesive/support, a removal film, a support, a UV protector, a masking agent capable of removing the unpleasant taste or odor of pharmaceuticals, a colorant, flavors and perfumes, an attaching substance that can be used as a supplement when administering drugs while being contained in the drug container, an attaching solvent used to help dissolve a solute into a solution and to use when administering drugs, a refreshing agent, a filler (air displacement) added to other materials to increase capacity or weight, a penetration enhancer used to facilitate penetration of the drug solution, a coating agent, a chelating agent, a decoloring agent, a degreasing agent, a labelling agent, a covering agent, an antioxidant, a suspending agent, an extenders for addition to products in the same dosage as a diluent or emollient, a reducing agent, a pill clothing agent, which is powder for the purpose of preventing mutual adhesion of pills, the occurrence of mold, and moisture evaporation, a lubricant agent to reduce friction when applied to the skin or to make it easier to swallow, a volatile restrainer, a volatilization accelerator, an absorbent that absorbs gas and liquid, an adsorbent for adsorbing gas, liquid or solute on surface, a humectant, a suspension product, a warming agent which is a substance that gives a feeling of warmth, an enteric coating agent capable of controlling pH-dependent and swelling behavior such as Eudragit, etc.

In the present invention, the pharmaceutical composition may be for preventing or treating any one or more of bacterial or viral infectious diseases, inflammatory diseases, and malignant tumor diseases. More specifically, the pharmaceutical composition of the present invention may be for corona virus prevention or treatment, and may be for anticancer.

The bacterial or viral infectious disease may be diseases such as malaria infection or viral diseases including Epstein Barr Virus (EBV), Hepatitis B Virus, Hepatitis C Virus, HIV, HTLV 1, Varicella-Zoster Virus (VZV), and Human Papilloma Virus (HPV), virus infection caused by corona virus such as SARS-CoV and/or SARS-CoV2, and other retrovirus infection, and the like.

The inflammatory diseases may be a disease such as vascular restenosis, inflammatory diseases including autoimmune diseases, pancreatitis, glomerulonephritis, myocardial infarction, and psoriasis; atopic diseases (Atopy) including allergic asthma, atopic dermatitis (eczema), and allergic rhinitis, Cell Mediated Hypersensitivity including Allergic Contact Dermatitis and Hypersensitivity Pneumonitis, rheumatic diseases including Systemic Lupus Erythematosus (SLE), Rheumatoid Arthritis, Juvenile Arthritis, Sjogren's Syndrome, Scleroderma, Polymyositis and Polymyositis, Ankylosing Spondylitis, and Psoriatic Arthritis, diabetes, autoimmune thyroid disease, brain diseases including dementia, Parkinson's disease, Alzheimer's disease, Other autoimmune diseases, degenerative diseases including arthritis, etc.

The malignant tumor disease may be a neoplastic disease appearing in cancer including cancer and carcinomas generated in breast, prostate, kidney, bladder, or colon tissue fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilms tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma; and adipocyte tumors such as lipoma, fibrolipoma, lipoblastoma, lipomatosis, hibemoma, hemangioma, and/or liposarcoma, neoplastic disease appearing in adipose tissue.

The pharmaceutical composition according to the present invention may be in the form of oral preparations, injections, mucosal preparations, inhalants, external preparations, transdermal absorption preparations (ointment, cream, etc.), etc., but is not limited thereto, and oral preparations may be preferable.

In the present invention, the pH adjuster may be a pH adjuster commonly used in the field to which the present invention belongs, preferably citric acid, malic acid, lactic acid, humic acid, glycolic acid, acetic acid, hydrochloric acid, hydrobromic acid, sulfuric acid, etc. may be used.

In the present invention, one or more excipients that can be used in pharmaceuticals such as monosaccharides, disaccharides, and trisaccharides, etc. including polyvinylpyrrolidone, glucose, phosphatide, polyhydric alcohol, and sucrose, trehalose, mannitol, lactose, citric acid, mannitol, and dextrose may be used.

The present invention provides a method for preparing a metal (hydr)oxide composite containing a metal (hydr)oxide and a poorly soluble drug and a prodrug thereof, the method including a step of preparing a calcined metal (hydr)oxide by calcining the metal (hydr)oxide; and a step of reacting the calcined metal (hydr)oxide and the poorly soluble drug or the prodrug thereof in an anhydrous organic solvent.

In the step of the reacting in the anhydrous organic solvent, the hydration reaction may not occur.

More specifically, the calcination in the step of preparing the calcined metal (hydr)oxide may be performed at a temperature of 250° C. or higher and 2000° C. or lower.

In addition, the present invention may provide a method for preparing a pharmaceutical composition, the method further comprising a step of performing a surfactant treatment on the metal (hydr)oxide composite described above to coat the metal (hydr)oxide composite.

The step of performing the surfactant treatment may include a step of preparing a surfactant solvent by dissolving a surfactant in an organic solvent, a step of forming a mixture by mixing and stirring the metal (hydr)oxide composite described above with the surfactant solvent, and a step of evaporating the solvent from the mixture.

Reference Example 1. Synthesis of Uncalcined Metal (Hydr) Oxide-Niclosamide Composite (HT)

In a nitrogen environment, 6.9 g of hydrotalcite (Sigma Aldrich or Kwoya Chemical Industry CO., LTD) is suspended in 700 ml of purified water and then stirred for 30 minutes. In the suspension, 3.4 g of niclosamide and NaOH (0.1 M aqueous solution) are mixed to prepare an aqueous solution of niclosamide sodium salt substituted with sodium salt, and then the aqueous sodium salt solution is slowly added dropwise to the hydrotalcite suspension for 30 minutes. In this case, the pH of the solution is maintained at 8.5 using NaOH. After titration, the solution is stirred for 18 hours under a nitrogen environment at room temperature, and the suspension is filtered using a filtered glass (membrane filter), and then washed 3 times using an aqueous solution with pH adjusted. Finally, after additional washing twice with ethanol, the suspension was dried for one day using a vacuum dryer (1 mbar, 40° C.) to obtain a white final composite with a yield of 70% (drug base).

Reference Example 2. Synthesis of Uncalcined Metal (Hydr) Oxide-Niclosamide Composite (HT)

After dissolving a solution, in which niclosamide was dissolved in tertiary distilled water from which carbonate ions $CO_3^{2-}$ were removed, in a solution, in which $Zn(NO_3)_2 \cdot H_2O$ is dissolved in tertiary distilled water from which carbonate ions $CO_3^{2-}$ were removed, the solution was titrated by maintaining the pH at about 6-7 using 0.2 M NaOH to obtain a zinc basic salt precipitate. The titrated solution was separated by a centrifuge, and unreacted salt was removed through a washing process. Thereafter, the prepared zinc basic salt precipitate was obtained, and then it was again subjected to centrifugation and washing, and then vacuum dried to obtain a yellowish powder.

Reference Example 3: HT($Mg_6Al_2(OH)_{16}CO_3 \cdot 4H_2O$)

Reference Example 4: DHT (350° C.)

In a nitrogen environment, 3 g each of hydrotalcite (Sigma Aldrich and Kwoya Chemical Industry CO., LTD) powder is taken and put it in each reaction vessel, and calcination is proceeded under the condition of 350° C. for 8 hours to obtain DHT.

Reference Example 5: DHT(350° C.):NIC=1:0.4—Grinding

Reference Example 5 was obtained by grinding DHT 0.6 g and Niclosamide 0.4 g of Reference Example 4 by taking a weight ratio of DHT to Niclosamide as 0.6:0.4.

Reference Example 6: DHT(350° C.):NIC=0.8:0.2—Grinding

Reference Example 6 was obtained by grinding DHT 0.8 g and Niclosamide 0.2 g of Reference Example 4 by taking a weight ratio of DHT to Niclosamide as 0.8:0.2.

Reference Example 7: $MgO:Al_2O_3$=2:1—Grinding

Reference Example 7 was obtained by grinding MgO powder 2 g and $Al_2O_3$ powder 1 g by taking a weight ratio of MgO and $Al_2O_3$ samples as 2:1.

Reference Example 8: $MgO:Al_2O_3$:NIC=2:1:1—Grinding

Reference Example 8 was obtained by grinding MgO powder 2 g and $Al_2O_3$ powder 1 g, and Niclosamide 1 g by taking a weight ratio of MgO, $Al_2O_3$, and Niclosamide samples as 2:1:1.

Figure 8:
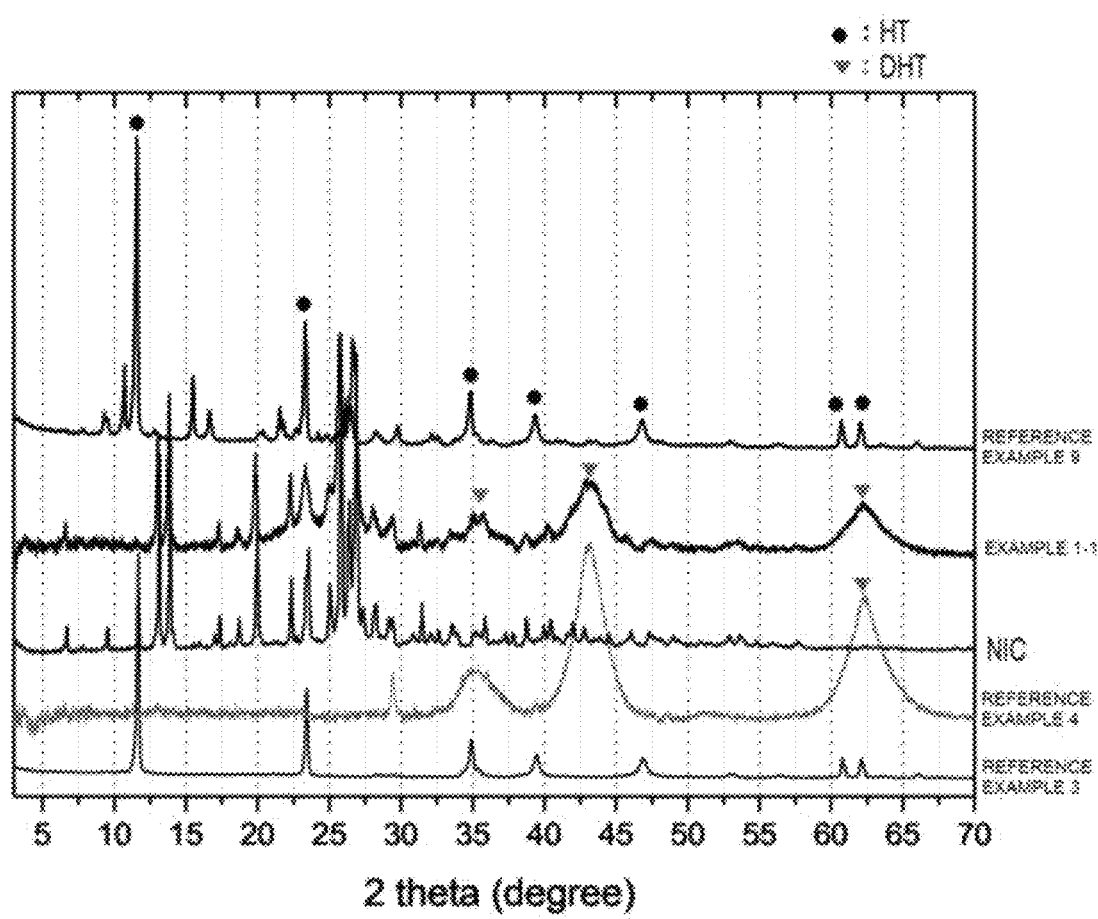
FIG. 8 illustrates an XRD graph for Example 1-1, Reference Example 3, Reference Example 4, Reference Example 9, and NIC.
Figure 9:
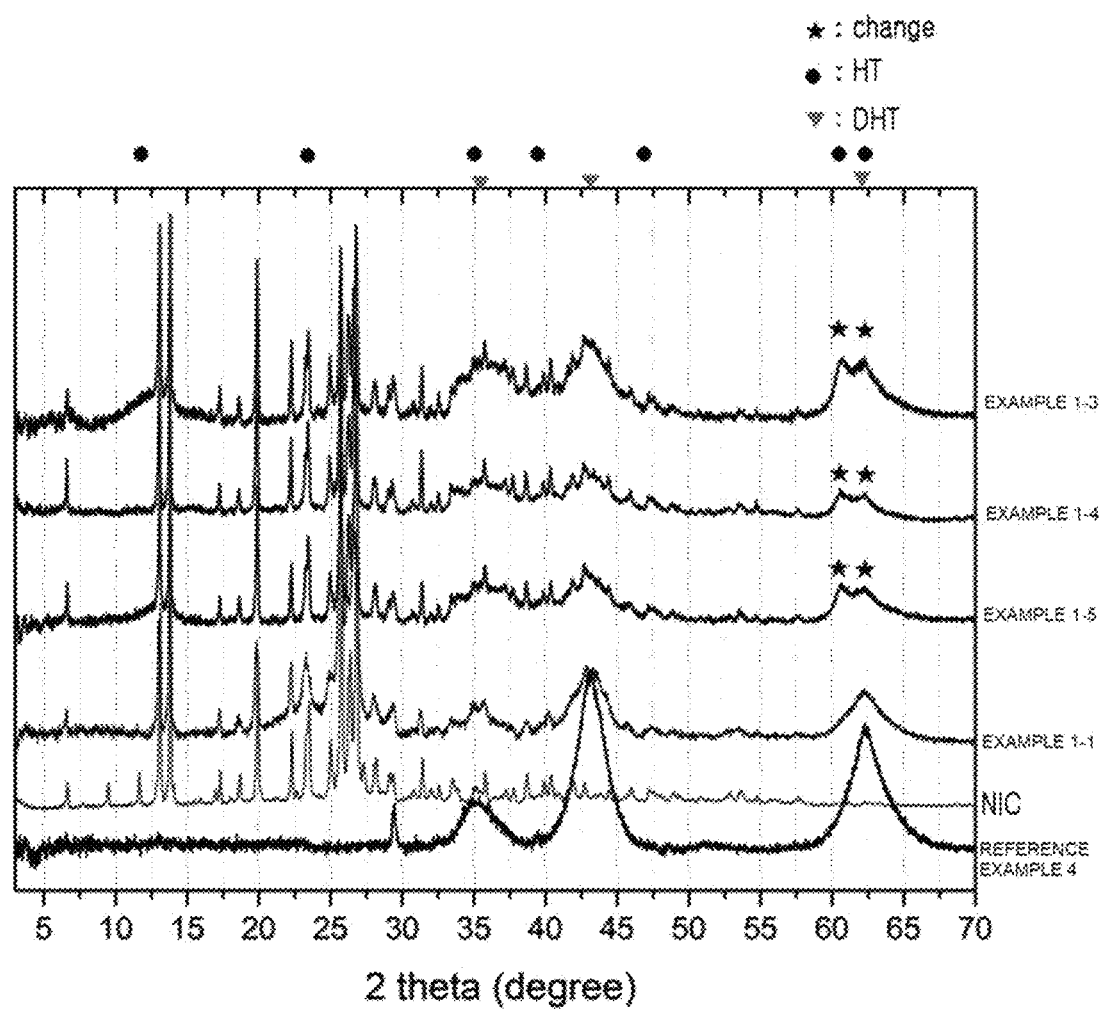
FIG. 9 illustrates an XRD graph for Example 1-1, Example 1-3, Example 1-4, Example 1-5, Reference Example 4, and NIC.
Figure 10:
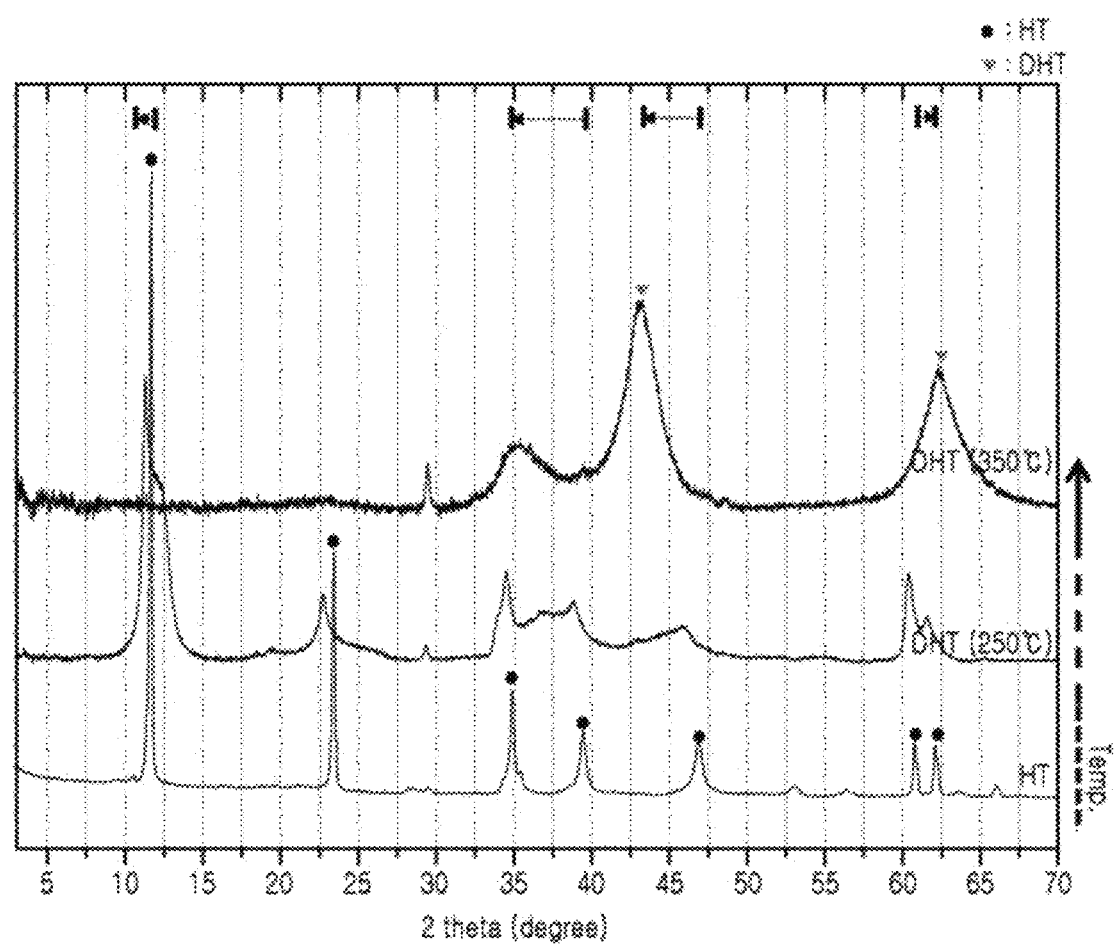
FIG. 10 illustrates an XRD graph for Reference Example 3 (HT), Reference Example 10 (DHT 250° C.), and Reference Example 4 (DHT 350° C.).

Reference Example 9: HT-NIC(36%)/EtOH 3 g of hydrotalcite (Sigma Aldrich or Kwoya Chemical Industry CO., LTD) powder and 50 ml of absolute ethanol are put in a flask, and the powder is dispersed well by sonication for 10 minutes. While stirring the solution at rpm 700 or higher, 3 g of niclosamide is added and then stirred for 6 hours. For purification, the filtrate was removed through a filter membrane, and the solution was washed 4-5 times with absolute ethanol and then vacuum dried to obtain yellowish DHT-NIC compound powder (content 36%). 0.356 g of HPMC is dissolved in a flask in a 1:1 ratio solution of absolute ethanol and dichloromethane. 2.0 g of the HT-NIC was put in each of the two main tanks and stirred rapidly for 30 minutes. After evaporating the solvent using a rotary evaporator, the obtained pharmaceutical composition (yellow powder) was dried to obtain the pharmaceutical composition of FIG. 8 (blue).

Reference Example 10: DHT(250° C.)

In a nitrogen environment, 3 g each of hydrotalcite (Sigma Aldrich and Kwoya Chemical Industry CO., LTD) powder is taken and put it in each reaction vessel, and calcination is proceeded under the condition of 250° C. for 8 hours to obtain DHT of Reference Example 10.

Reference Example 11: DHT(350° C.)-NIC/EtOH+$H_2O$

Dehydrotalcite and Niclosamide calcined at 350° C. were synthesized in anhydrous ethanol (NIC content 44%), and water was added (4%) to CHT-NIC and an anhydrous ethanol solution, followed by stirring for 48 hours.

Reference Example 12: DHT (350° C.)/EtOH+$H_2O$

To Dehydrotalcite calcined at 350° C. and anhydrous ethanol solution, water was added (4%) and stirred for 48 hours.

Reference Example 13: HT-NIC/HMPC

HT-NIC(NIC content 35%) obtained after synthesizing hydrotalcite (Sigma Aldrich or Kwoya Chemical Industry CO., LTD.) and Niclosamide in anhydrous ethanol, filtering, and washing, was reacted with HPMC in anhydrous ethanol and dichloromethane solution to obtain the product.

Reference Example 14: DHT(350° C.)/EtOH

Dehydrotalcite calcined at 350° C. was stirred in anhydrous ethanol solution for 48 hours.

Synthesis in Examples 1-1 and 1-2: Synthesis of Calcined Metal (Hydr)Oxide-Niclosamide Composite (DHT-NIC Composite)

<STEP 1>
3 g each of hydrotalcite (Sigma Aldrich and Kwoya Chemical Industry CO., LTD) powder is taken and put it in each reaction vessel, and calcination is proceeded under the condition of 350° C. for 8 hours.
<STEP 2>
200 ml of anhydrous methanol is put in each vessel and the powder is dispersed well by sonication for 10 minutes. While stirring each solution at rpm 700 or higher, 3 g (Example 1-1) and 1.5 g (Example 1-2) of niclosamide are added and then stirred for 6 hours. For purification, the filtrate was removed through a filter membrane, and the solution was washed 4-5 times with absolute ethanol and then vacuum dried to obtain a yellowish powder. The final niclosamide content was 44% for Example 1-1 and 22% for Example 1-2.

Synthesis in Examples 1-3 to 1-5: Synthesis of Calcined Metal (Hydr)Oxide-Niclosamide Composite (DHT-NIC Composite)

<STEP 1>
3 g each of hydrotalcite (Sigma Aldrich and Kwoya Chemical Industry CO., LTD) powder is taken and put in three reaction vessels (Example 1-3, Example 1-4, Example 1-5), and calcination is proceeded under the condition of 350° C. for 8 hours.
<STEP 2>
100 ml, 50 ml, and 25 ml of absolute ethanol are put in the vessels, respectively, and the powder is dispersed well by sonication for 10 minutes. While stirring each solution at rpm 700 or higher, 3 g of niclosamide is added and then stirred for 6 hours. For purification, the filtrate was removed through a filter membrane, and the solution was washed 4-5 times with absolute ethanol and then vacuum dried to obtain a yellowish powder. The final niclosamide content was 32% for Example 1-3, 46% for Example 1-4, and 31% for Example 1-5.

Example 2: Synthesis of Calcined Metal (Hydr)Oxide-Niclosamide Composite (DHT-NIC Composite)

3 g each of hydrotalcite (Sigma Aldrich and Kwoya Chemical Industry CO., LTD) powder is taken and put in each reaction vessel at 50° C. intervals under the condition of 250° C. or more and 800° C. or less, and calcination was performed for 8 hours. 50 ml of absolute ethanol is put in each vessel and the powder is dispersed well by sonication for 30 minutes. While stirring each solution at rpm 700 or higher, 50 ml of absolute ethanol and 3 g of niclosamide are added and then stirred for 24 hours. For purification, the filtrate was removed through a filter membrane, and the solution was washed 4-5 times with absolute ethanol and then vacuum dried to obtain a yellowish powder.

Example 3: Synthesis of Calcined Metal (Hydr)Oxide-Niclosamide Composite (DHT-NIC Composite)

In a nitrogen environment, 6.9 g of pristine ZnAl-LDH is suspended in 700 ml of purified water and then stirred for 30 minutes. In the suspension, 3.4 g of niclosamide and NaOH (0.1 M aqueous solution) are mixed to prepare an aqueous solution of niclosamide sodium salt substituted with sodium salt, and then the aqueous sodium salt solution is slowly added dropwise to the LDH pristine suspension for 30 minutes. In this case, the pH of the solution is maintained at 8.5 using NaOH. After titration, the solution is stirred for 18 hours under a nitrogen environment at room temperature, and the suspension is filtered using a filtered glass (membrane filter), and then washed 3 times using an aqueous solution with pH adjusted. Finally, after additional washing twice with ethanol, the suspension was dried for one day using a vacuum dryer (1 mbar, 40° C.) to obtain a white final composite with a yield of 70% (drug base). Next, 3 g each of powder was taken at an interval of 50° C. under the conditions of 250° C. or higher and 800° C. or less, each powder is put in each reaction vessel, and calcination is proceeded for 8 hours. 50 ml of absolute ethanol is put in each container and the powder is dispersed well by sonication for 30 minutes. While stirring each solution at rpm 700 or higher, 50 ml of absolute ethanol and 3 g of niclosamide are added and then stirred for 24 hours. For purification, the filtrate was removed through a filter membrane, and the solution was washed 4-5 times with acetone and absolute ethanol and then vacuum dried to obtain a yellowish powder.

Examples 4 and 5. Preparation of Pharmaceutical Composition Containing Calcined Metal (Hydr)Oxide-Niclosamide Composite

<STEP 1>

3 g of hydrotalcite (Sigma Aldrich or Kwoya Chemical Industry CO., LTD) powder is taken, the powder is put in an alumina container, and calcination is proceeded in a furnace at 350° C. for 8 hours.

<STEP 2>

Figure 19:
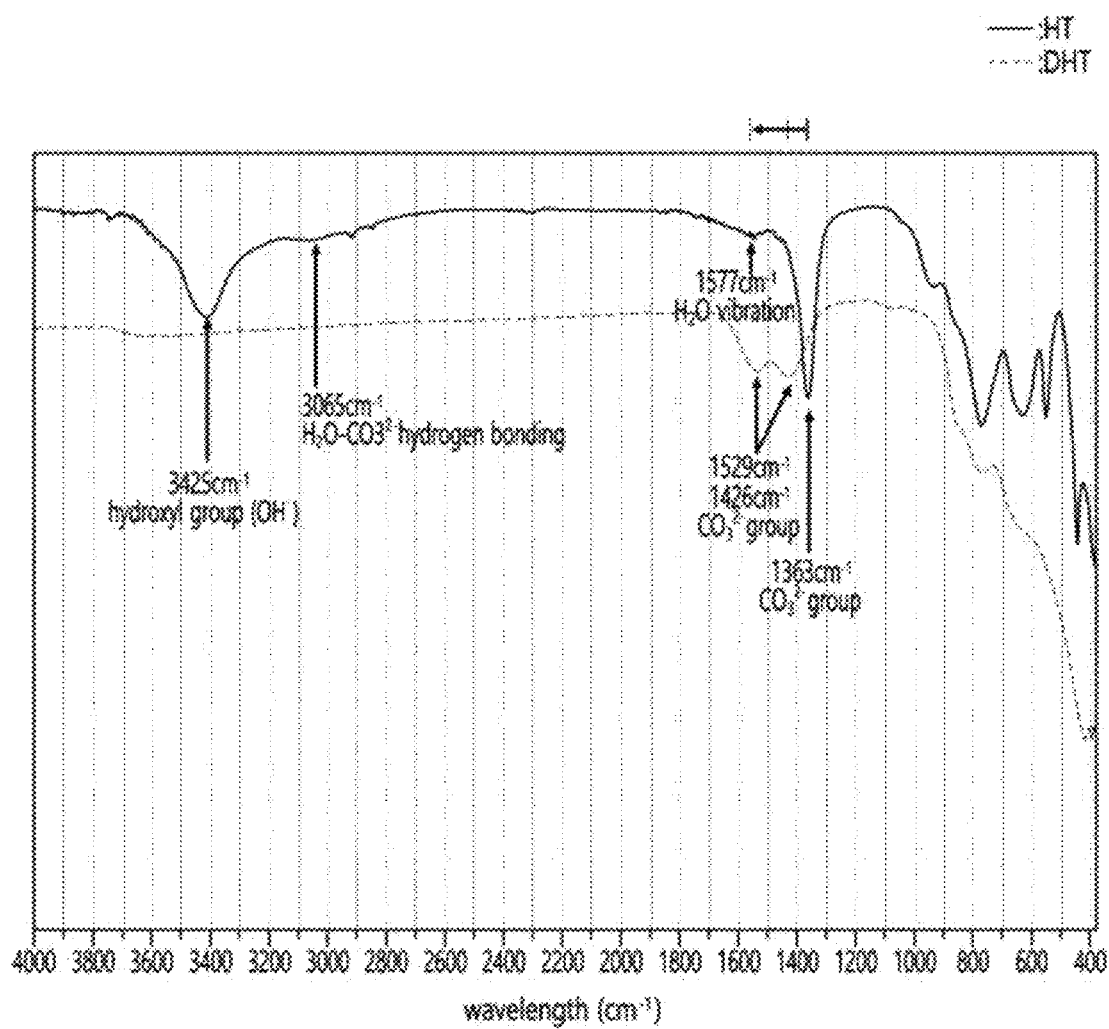
FIG. 19 illustrates a Fourier transform infrared (FT-IR) spectrum graph of HT (Reference Example 3) and DHT (Reference Example 4).
Figure 20:
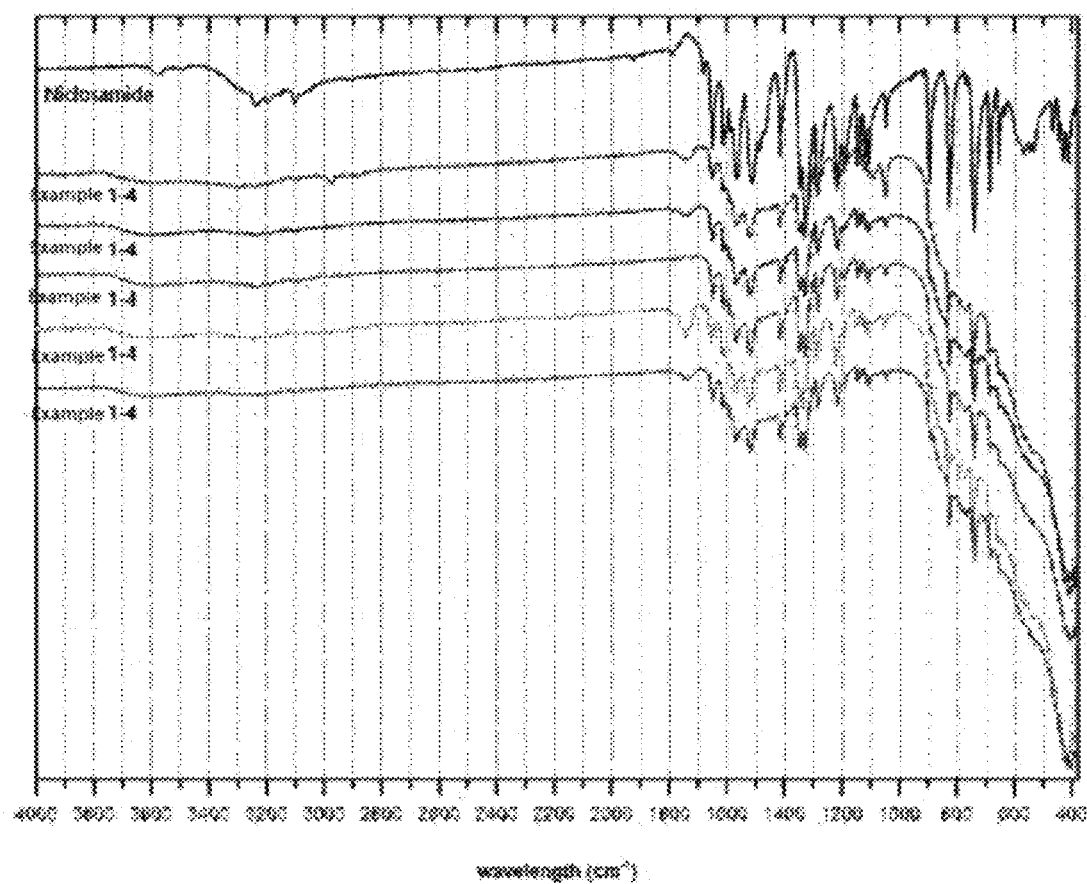
FIG. 20 illustrates a Fourier transform infrared (FT-IR) spectrum graph obtained by repeated measurements of NIC and Example 1-4.

Each powder is put in a flask, 50 ml of absolute ethanol is put in a flask, and the powder is dispersed well by sonication for 10 minutes. While stirring each solution at rpm 700 or higher, 3 g of niclosamide is added and then stirred for 6 hours. For purification, the filtrate was removed through a filter membrane, and the solution was washed 4-5 times with absolute methanol and then vacuum dried to obtain a yellowish DHT-NIC compound powder which exhibited a niclosamide content of 43.3%. The FT-IR graph of the composite is illustrated in FIG. 19.

<STEP 3>

In two main tanks, 0.270 g of HPMC or 0.540 g of Tween 60 in is dissolved in 1:1 ratio solution of absolute ethanol and dichloromethane or absolute ethanol. 1.350 g of the DHT-NIC is put in each of the two main tanks and stirred rapidly for 30 minutes. After evaporating the solvent using a rotary evaporator, the obtained pharmaceutical composition (yellow powder) is dried to obtain the pharmaceutical compositions of Examples 4 and 5, respectively.

Examples 6 to 11. Preparation of Pharmaceutical Composition Containing Calcined Metal (Hydr)Oxide-Niclosamide Composite

<STEP 1>

3 g each of hydrotalcite (Sigma Aldrich and Kwoya Chemical Industry CO., LTD) powder is taken and put in each reaction vessel in three reaction vessels, and calcination is proceeded under the condition of 350° C. for 8 hours.

<STEP 2>

50 ml of absolute ethanol is put in each reaction container and the powder is dispersed well by sonication for 10 minutes. While stirring the solution at rpm 700 or higher, 3 g of niclosamide is added and then stirred for 6 hours. For purification, the filtrate was removed through a filter membrane, and the solution was washed 4-5 times with absolute ethanol and then vacuum dried to obtain a yellowish powder. The final niclosamide content was 46%.

<STEP 3>

A solution in which niclosamide and HPMC were dissolved in absolute ethanol and dichloromethane was put in to the DHT-NIC composite prepared in Steps 1 and 2, stirred, and then evaporated (or spray dried) to prepare the pharmaceutical compositions of Examples 6 to 11.

An implementation method of STEP 3 of each of Examples 6 to 11 is as follows.

Example 6 STEP 3

In the main tank, 0.546 g of HPMC is dissolved in 1:1 ratio solution of absolute ethanol and dichloromethane. 2.728 g of the DHT-NIC is put in the main tank and stirred rapidly for 30 minutes. After evaporating the solvent using a rotary evaporator, the obtained pharmaceutical composition (yellow powder) is dried to obtain the pharmaceutical composition.

Example 7 STEP 3

In the main tank, 0.390 g of HPMC is dissolved in 1:1 ratio solution of absolute ethanol and dichloromethane. After dissolving 0.61 g of niclosamide in this solution, 1.34 g of DHT-NIC is put in the main tank and stirred rapidly for 30 minutes. After evaporating the solvent using a rotary evaporator, the obtained pharmaceutical composition (yellow powder) is dried to obtain the pharmaceutical composition.

Example 8 STEP 3

In the main tank, 0.316 g of HPMC is dissolved in 1:1 ratio solution of absolute ethanol and dichloromethane. After dissolving 0.906 g of niclosamide in this solution, 1.34 g of DHT-NIC is put in the main tank and stirred rapidly for 30 minutes. After evaporating the solvent using a rotary evaporator, the obtained pharmaceutical composition (yellow powder) is dried to obtain the pharmaceutical composition.

Pharmaceutical compositions of Examples 9 to 11 were prepared in the same manner as in the method described above, except that niclosamide and Tween 60 were additionally dissolved in the DHT-NIC in STEP 3 described above. The specific preparation methods of STEPs 3 of Examples 9 to 11 are as follows, respectively.

Example 9 STEP 3

1.092 g of Tween 60 is dissolved in anhydrous ethanol solution in the main tank. 2.728 g of DHT-NIC is put in the main tank and stirred rapidly for 30 minutes. After evaporating the solvent using a rotary evaporator, the obtained pharmaceutical composition (yellow powder) is dried to obtain the pharmaceutical composition.

Example 10 STEP 3

0.78 g of Tween 60 is dissolved in anhydrous ethanol solution in the main tank. After dissolving 0.61 g of niclosamide in this solution, 1.34 g of DHT-NIC is put in the main tank and stirred rapidly for 30 minutes. After evaporating the solvent using a rotary evaporator, the obtained pharmaceutical composition (yellow powder) is dried to obtain the pharmaceutical composition.

Example 11 STEP 3

0.632 g of Tween 60 is dissolved in anhydrous ethanol solution in the main tank. After dissolving 0.906 g of niclosamide in this solution, 1.34 g of DHT-NIC is put in the main tank and stirred rapidly for 30 minutes. After evaporating the solvent using a rotary evaporator, the obtained pharmaceutical composition (yellow powder) is dried to obtain the pharmaceutical composition.

Specific contents of the pharmaceutical compositions of Examples 6 to 11 prepared by the methods described above are illustrated in Tables 1 and 2 below.

TABLE 1

| Classification | | Ingredient ratio | | Manufacturing ingredients | | |
|---|---|---|---|---|---|---|
| | | DHT/ (DHT + NIC) (%) | HPMC (%) | NIC/ DHT (mg) | Additional NIC (mg) | HPMC (6 mPas) (mg) |
| Example 6 | DHT-D56H | 56 | 16.7 | 2728 | 0 | 546 |
| Example 7 | DHT-D38H | 38 | 16.7 | 1340 | 610 | 546 |
| Example 8 | DHT-D24H | 24 | 16.7 | 668 | 906 | 546 |

TABLE 2

| Classification | | Ingredient ratio | | Manufacturing ingredients | | |
|---|---|---|---|---|---|---|
| | | DHT/ (DHT + NIC) (%) | Tween 60 (%) | NIC/ DHT (mg) | Additional NIC (mg) | Tween 60 (mg) |
| Example 9 | DHT-D56T | 56 | 33.4 | 2728 | 0 | 1092 |
| Example 10 | DHT-D38T | 38 | 33.4 | 1340 | 610 | 1092 |
| Example 11 | DHT-D24T | 24 | 33.4 | 668 | 906 | 1092 |

Examples 12-1 to 12-4: Preparation of Calcined Metal (Hydr) Oxide-Niclosamide Composite and Pharmaceutical Composition Containing Same <Step 1>

3 g each of Mg(OH)$_2$ powder is taken, this powder is put in two reaction vessels, and calcination is proceeded for 6 hours under the conditions of 200° C. (Example 12-1) and 300° C. (Example 12-2).

<Step 2>

50 ml of absolute ethanol is put in each reaction container and the powder is dispersed well by sonication for 30 minutes. While stirring the solution at rpm 700 or higher, 3 g of niclosamide is added and then stirred for 4 hours. For purification, the filtrate was removed through a filter membrane, and the solution was washed 4-5 times with absolute ethanol and then vacuum dried to obtain a yellowish powder. The final niclosamide content was 35.2% (metal hydroxide-NIC composite of Example 12-1) for the synthetic compound calcined at 200° C. and 14.5% (metal hydroxide-NIC composite of Example 12-2) for the synthetic compound calcined at 300° C.

<Step 3>

2 g of each metal hydroxide-NIC composite prepared in Steps 1 and 2 was put in a 1:1 ratio solution of anhydrous ethanol and dichloromethane in which HPMC was dissolved, stirred, and evaporated (or spray dried) to prepare a pharmaceutical composition.

Specific contents of the pharmaceutical compositions of Examples 12-3 and 12-4 prepared by the method described above are illustrated in Table 3 below.

TABLE 3

| Classification | | Ingredient ratio | | Manufacturing ingredients | | |
|---|---|---|---|---|---|---|
| | | Mg (OH)$_2$/ (Mg (OH)$_2$ + NIC) (%) | HPMC (%) | NIC/Mg (OH)$_2$ (mg) | Additional NIC (mg) | HPMC (mg) |
| Example 12-3 | Mg (OH)$_2$ 200° C. | 65 | 13.6 | 2000 | 0 | 314 |
| Example 12-3 | Mg (OH)$_2$ 300° C. | 85.5 | 13.6 | 1340 | 0 | 131 |

Examples 13-1 and 13-2: Preparation of Calcined Metal Oxide-Niclosamide Composite and Pharmaceutical Composition Containing Same <Step 1>

3 g of MgO powder is taken, this powder is put in the reaction vessel, and calcination is proceeded for 6 hours under the condition of 800° C.

<STEP 2>

50 ml of absolute ethanol is put in each reaction container and the powder is dispersed well by sonication for 10 minutes. While stirring the solution at rpm 700 or higher, 3 g of niclosamide is added and then stirred for 4 hours. For purification, the filtrate was removed through a filter membrane, and the solution was washed 4-5 times with absolute ethanol and then vacuum dried to obtain a yellowish powder. The final niclosamide content was 34.6% (Example 13-1).

<STEP 3>

2 g of DHT-NIC composite prepared in Steps 1 and 2 was put in a 1:1 ratio solution of anhydrous ethanol and dichloromethane in which 0.306 g of HPMC was dissolved, stirred, and evaporated (or spray dried) to prepare a pharmaceutical composition of Example 13-2.

Specific contents of the pharmaceutical composition of Example 13-2 prepared by the method described above is illustrated in Table 4 below.

TABLE 4

| Classification | | Ingredient ratio | | Manufacturing ingredients | | |
|---|---|---|---|---|---|---|
| | | MgO/ (MgO + NIC) (%) | HPMC (%) | NIC/ MgO (mg) | Additional NIC (mg) | HPMC (mg) |
| Example 13-2 | MgO 800° C. | 65.4 | 13.6 | 2000 | 0 | 306 |

Examples 14-1 and 14-2: Preparation of Calcined Metal (Hydr)Oxide-Docetaxel Composite and Pharmaceutical Composition Containing Same

<STEP 1>

3 g of hydrotalcite (Sigma Aldrich or Kwoya Chemical Industry CO., LTD) powder is taken and put in a reaction vessel, and calcination is proceeded under the condition of 350° C. for 8 hours.

<STEP 2>

50 ml of anhydrous acetonitrile is put in each reaction container and the powder is dispersed well by sonication for 10 minutes. While stirring the solution at rpm 700 or higher, 3 g of docetaxel is added and then stirred at 0° C. for 1 hour. The synthetic compound was vacuum dried to obtain a white powder (DHT-DTX composite; Example 14-1).

<STEP 3>

1 g of DHT-DTX composite prepared in Steps 1 and 2 was put in a 1:1 ratio solution of anhydrous ethanol and dichloromethane in which 0.221 g of HPMC was dissolved, stirred, and evaporated (or spray dried) to prepare a pharmaceutical composition of Example 14-2.

Examples 15-1 and 15-2: Preparation of Calcined Metal (Hydr)Oxide-Docetaxel Composite and Pharmaceutical Composition Containing Same

<STEP 1>

3 g of hydrotalcite (Sigma Aldrich or Kwoya Chemical Industry CO., LTD) powder is taken and put in a reaction vessel, and calcination is proceeded under the condition of 350° C. for 8 hours.

<STEP 2>

50 ml of anhydrous acetonitrile is put in in each reaction container and the powder is dispersed well by sonication for 10 minutes. While stirring the solution at rpm 700 or higher, 3 g of docetaxel is added and then stirred at room temperature for 1 hour. For purification, the filtrate was removed through a filter membrane, and the solution was washed 4-5 times with absolute ethanol and then vacuum dried to obtain a white powder (DHT-DTX composite; Example 15-1).

<STEP 3>

1 g of DHT-DTX composite of Example 15-1 prepared in Steps 1 and 2 was put in a 1:1 ratio solution of anhydrous ethanol and dichloromethane in which 0.221 g of HPMC was dissolved, stirred, and evaporated (or spray dried) to prepare a pharmaceutical composition of Example 15-2.

Examples 16-1 and 16-2: Preparation of Calcined Metal Oxide-Niclosamide Composite and Pharmaceutical Composition Containing Same

<STEP 1>

3 g of MgO powder is taken, this powder is put in the reaction vessel, and calcination is proceeded for 6 hours under the condition of 800° C.

<STEP 2>

50 ml of anhydrous acetonitrile is put in each reaction container and the powder is dispersed well by sonication for 10 minutes. While stirring the solution at rpm 700 or higher, 3 g of docetaxel is added and then stirred at 0° C. for 1 hour. The synthetic compound was vacuum dried to obtain a white powder (MgO-DTX composite; Example 16-1).

<STEP 3>

1 g of MgO-DTX composite prepared in Steps 1 and 2 was put in a 1:1 ratio solution of anhydrous ethanol and dichloromethane in which 0.221 g of HPMC was dissolved, stirred, and evaporated (or spray dried) to prepare a pharmaceutical composition of Example 16-2.

Examples 17-1 and 17-2: Preparation of Calcined Metal Oxide-Niclosamide Composite and Pharmaceutical Composition Containing Same

<STEP 1>

3 g of MgO powder is taken, this powder is put in the reaction vessel, and perform calcination for 6 hours under the condition of 800° C.

<STEP 2>

50 ml of anhydrous acetonitrile is put in each reaction container and the powder is dispersed well by sonication for 10 minutes. While stirring the solution at rpm 700 or higher, 3 g of docetaxel is added and then stirred at room temperature for 1 hour. For purification, the filtrate was removed through a filter membrane, and the solution was washed 4-5 times with absolute ethanol and then vacuum dried to obtain a white powder (MgO-DTX composite; Example 17-1).

<STEP 3>

1 g of MgO-DTX composite of Example 17-1 prepared in Steps 1 and 2 was put in a 1:1 ratio solution of anhydrous ethanol and dichloromethane in which 0.221 g of HPMC was dissolved, stirred, and evaporated (or spray dried) to prepare a pharmaceutical composition.

Example 18: Preparation of a Pharmaceutical Composition Containing Calcined Metal (Hydr)Oxide-Niclosamide Composite (Preparation by Physical Grinding Method)

In this example, a pharmaceutical composition containing a calcined metal (hydr)oxide composite was prepared by mixing the components through a simple method of physical grinding or milling without a solvent to increase homogeneity and dispersion.

<STEP 1>

3 g each of hydrotalcite (Sigma Aldrich and Kwoya Chemical Industry CO., LTD) powder is taken and put in the reaction vessel, and calcination is proceeded under the condition of 350° C. for 8 hours.

<STEP 2>

0.5 g of DHT, 0.5 g of niclosamide, and 0.225 g of HPMC were added to each container of a Mortar Grinder or bead mill machine and mixed to obtain a yellowish powder, which is the pharmaceutical composition of Example 18. The final niclosamide content was 40%.

Specific contents of the pharmaceutical composition of Example 18 prepared by the method described above are illustrated in Table 5 below.

TABLE 5

| | Ingredient ratio | | Manufacturing ingredients | | |
|---|---|---|---|---|---|
| Classification | DHT/ (DHT + NIC) (%) | HPMC (%) | NIC/DHT (mg) | Additional NIC (mg) | HPMC (mg) |
| Example 18 (AB40hg) | 50 | 18.37 | 1000 | 0 | 225 |

Example 19: Preparation of a Pharmaceutical Composition Containing Calcined Metal (Hydr)Oxide-Niclosamide Composite

<STEP 1>

3 g each of hydrotalcite (Sigma Aldrich and Kwoya Chemical Industry CO., LTD) powder is taken and put in the reaction vessel, and calcination is proceeded under the condition of 350° C. for 8 hours.

<STEP 2>

50 ml of absolute ethanol is put in each reaction container and the powder is dispersed well by sonication for 10 minutes. While stirring the solution at rpm 700 or higher, 3 g of niclosamide was added and then was stirred for 6 hours and then vacuum dried to obtain a yellowish powder. The final niclosamide content was 49%.

<STEP 3>

In the main tank, 0.394 g of HPMC is dissolved in a 1:1 ratio solution of absolute ethanol and dichloromethane. 2.025 g of the DHT-NIC is put in the main tank and the DHT-NIC is stirred rapidly for 30 minutes. After evaporating the solvent using a rotary evaporator, the obtained pharmaceutical composition (yellow powder) is dried to obtain a pharmaceutical composition of Example 19.

Example 20: Preparation of a Pharmaceutical Composition Containing Metal Oxide-Niclosamide Composite (NIC-MgO-HPMC-Poloxamer: 1:0.5:1:1)

To a vessel of Mortar grinder or bead mill machine, 0.5 g of niclosamide, 0.225 g of MgO (room temperature), 0.5 g of HPMC and 0.5 g of poloxamer were injected, and blending was performed to obtain a powder of a pharmaceutical composition of Example 20.

Example 21: Preparation of a Pharmaceutical Composition Containing Metal Oxide-Niclosamide Composite (NIC-MgO-HPMC-Poloxamer: 1:1:1:1)

To a vessel of Mortar grinder or bead mill machine, 0.5 g of niclosamide, 0.5 g of MgO, 0.5 g of HPMC and 0.5 g of poloxamer were injected, and blending was performed to obtain a powder of a pharmaceutical composition of Example 21.

Example 22: Preparation of a Pharmaceutical Composition Containing Metal Oxide-Niclosamide Composite (NIC-MgO-HPMC-Poloxamer: 1:2:1:1)

To a vessel of Mortar grinder or bead mill machine, 0.5 g of niclosamide, 1 g of MgO, 0.5 g of HPMC and 0.5 g of poloxamer were injected, and blending was performed to obtain a powder of a pharmaceutical composition of Example 22.

Examples 23-1 to 23-3: Preparation of Pharmaceutical Compositions Containing Metal Oxide-Niclosamide Composites (NIC-MgO-HPMC-Poloxamer: 1:2:1:1)

To a vessel of Mortar grinder or bead mill machine, niclosamide, MgO, HPMC and poloxamer were injected in the contents of Table 6, and blending was performed to obtain powders of pharmaceutical compositions of Example 23-1 to Example 23-3.

TABLE 6

| Content (g) | Niclosamide | MgO | Surfactant HPMC | poloxamer | MgO content (%) in composition |
|---|---|---|---|---|---|
| Example 23-1 | 1 | 0.5 | 1 | 1 | 15 |
| Example 23-2 | 1 | 1 | 1 | 1 | 25 |
| Example 23-3 | 1 | 2 | 1 | 1 | 40 |

Example 24: Preparation of a Pharmaceutical Composition Containing Metal Oxide-Niclosamide Composite To a vessel, Niclosamide, MgO (room temperature), HPMC and poloxamer were injected in a weight ratio of 1:2:1:1 and uniformly dispersed in ethanol, and ethanol was vacuum dried to obtain a powder of a pharmaceutical composition of Example 24.

Example 25: Preparation of a Pharmaceutical Composition Containing Metal Oxide-Niclosamide Composite 400 mg of Niclosamide and 280 mg of MgO (room temperature) were mixed and stirred in a EtOH solvent for 6 hours, and EtOH was removed though a vacuum drier to obtain a powder. This was mixed with 100 mg of HPMC (6 maps), and ground to obtain a powder.

Comparative Example 1: Yomesan

Yomesan, which is a commercially available niclosamide drug, was used as a comparative example after adjusting only the content.

Comparative Example 2: Preparation of a Metal (Hydr) Oxide-Composite of a Compound Having a Solubility in Water of 0.01 or Higher and/or not Including an OH Group, and a Pharmaceutical Composition Thereof To a vessel of Mortar grinder or bead mill machine, 0.5 g of MgO and 0.5 g of 5-FU (solubility in water of 12.2 mg/mL) and 0.225 g of HPMC were injected and mixed to obtain a powder of a pharmaceutical composition of Comparative Example 2.

Comparative Example 3: Preparation of a Metal Hydr(Oxide)-Composite of a Compound Having a Solubility in Water of 0.01 or Higher and/or not Including an OH Group, and a Pharmaceutical Composition Thereof To a vessel of Mortar grinder or bead mill machine, 0.5 g of MgO, 0.5 g of lipoic acid (solubility in water of 0.24 mg/mL) and 0.225 g of HPMC were injected and mixed to obtain a powder of a pharmaceutical composition of Comparative Example 3.

Comparative Example 4: Preparation of a Metal Hydr(Oxide)-Composite of a Compound Having a Solubility in Water of 0.01 or Higher and/or not Including an OH Group, and a Pharmaceutical Composition Thereof To a vessel of Mortar grinder or bead mill machine, 0.5 g of MgO, 0.5 g of artesunate (solubility in water of 0.5/mL) and 0.225 g of HPMC were injected and mixed to obtain a powder of a pharmaceutical composition of Comparative Example 4.

Comparative Example 5: Preparation of a Pharmaceutical Composition of Niclosamide To a vessel of Mortar grinder or bead mill machine, 0.5 g of Niclosamide, 0.5 g of HPMC and 0.5 g of poloxamer were injected and mixed to obtain a powder of a pharmaceutical composition of Comparative Example 5.

Experimental Example 1: HPLC Analysis

<Experiment Method and Conditions>
☐ Niclosamide HPLC analysis method
final update: 2021.04.14
wavelength: UV 330 nm
column: Poroshell 120 C18 2.7 um (21×100 mm)
Mobile Phase→A: 10 mM Ammonium acetate (0.1% Formic acid), B: ACN Gradient method

| Time (min) | A (%) | B (%) | Flow (ml/min) | Max. Pressure Limit (bar) |
|---|---|---|---|---|
| 0.0 | 80.0 | 20.0 | 0.400 | 400.00 |
| 0.5 | 80.0 | 20.0 | 0.400 | — |
| 5.0 | 10.0 | 90.0 | 0.400 | — |
| 5.5 | 10.0 | 90.0 | 0.400 | — |
| 5.6 | 70.0 | 30.0 | 0.400 | — |
| 10.0 | 80.0 | 20.0 | 0.400 | — |
| 15.0 | 80.0 | 20.0 | 0.400 | — | column temperature: 40° C.
injection: 5 μl
Runtime: 15 min
Bar(pressure): 280-300 bar 1) Standard Curve Sample Pretreatment Method After measuring the weight of niclosamide (powder), a solution with a concentration of 70-75 ppm of the powder is made in MeOH (0.25% TFA), sonication is proceeded for 10 minutes, and diluted solutions are made one after the other (at least 7 points) and the diluted solutions are analyzed after stirring for 10 minutes (measurement of niclosamide concentration is possible from 1 to 70 ppm with a standard curve)

2) Powder for Analysis Sampling

The weight of sample (granule) of the dosage form of the niclosamide is measured, a solution with a concentration of 100 ppm of the sample is made in MeOH (0.25% TFA), sonication is proceeded for 10 minutes, and then the sample is analyzed by performing filtration with a 0.2 um PTFE filter after stirring for 10 minutes (sample concentration is measured at 30-50 ppm).

3) Raw Material Content Measurement and Comparative Analysis

After HPLC analysis (15 minutes of analysis), it is checked whether there is a peak detected in the vicinity of integration and other RT. An area of Report is checked and the content is obtained by substituting it into the existing standard curve.

Experimental Example 2: Powder X-Ray Diffraction (PXRD) Analysis

Instrument: Powder X-ray Diffraction (PXRD)
X-ray diffractometer (D/MAXPRINT 2200-Ultima, Rigaku, Japan)
Cu-Kα radiation ($\lambda=1.5418$ Å)
tube voltage 40 kV, current 30 mA The measurement was performed using a D/MAXPRINT 2200-Ultima manufactured by Rigaku (Japan) as an X-ray diffractometer. The measurement was performed by using Cu metal as a cathode for generating X-rays, using Kα ray ($\lambda=1.5418$ Å) having a measurement range of $2\theta=3$ to $70°$, taking scanning speed of $0.02°/0.2$ sec, and respectively setting divergence slit, scattering slit, and receiving slit to 0.1, 1, and 1 mm. A tube voltage of 40 kV and a current of 30 mA were applied.

Evaluation Criteria

The one-dimensional (1D) electron density along the z-axis is calculated by the equation below.

$$\rho(z) = \sum_{l=0}^{\infty} F_{00l} \cos\frac{2\pi l z}{c}$$

The powder obtained through the synthesis was comparatively analyzed through an XRD diffraction pattern, and a resulting interlayer distance was calculated through Bragg's equation (Equation 2 below). In the case of the peak located at the front, it indicates an interlayer distance including a distance between the layer of the synthesized metal compound and the layer where the anion exists, and it can be regarded as a main interlayer distance.

$$n\lambda = 2d \sin\theta \quad \text{[Equation 2]}$$

($\lambda$=wavelength of X-rays, d=lattice spacing of crystals, $\theta$=angle of incidence)

The measured XRD patterns are illustrated in FIGS. 3 to 12.

Figure 3:
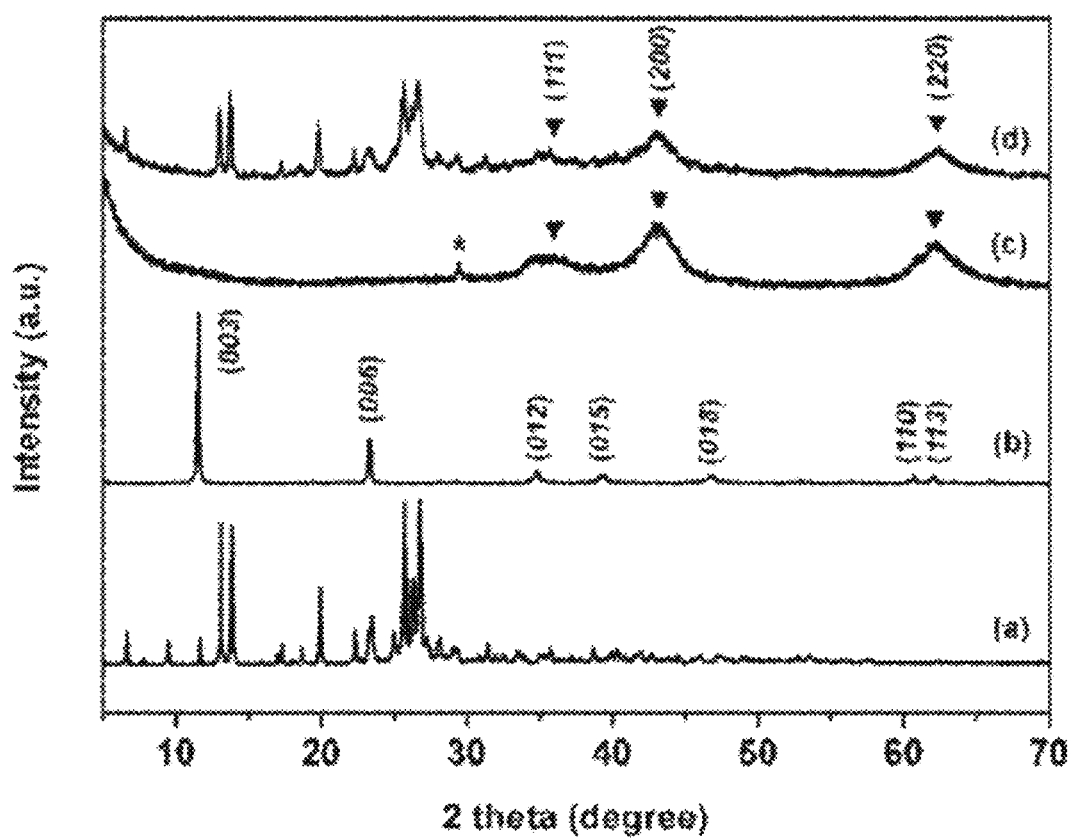
FIG. 3 illustrates an XRD graph, in which (a) is for NIC, (b) is for HT, (c) is for DHT, and (d) is for DHT-NIC composite.
Figure 4:
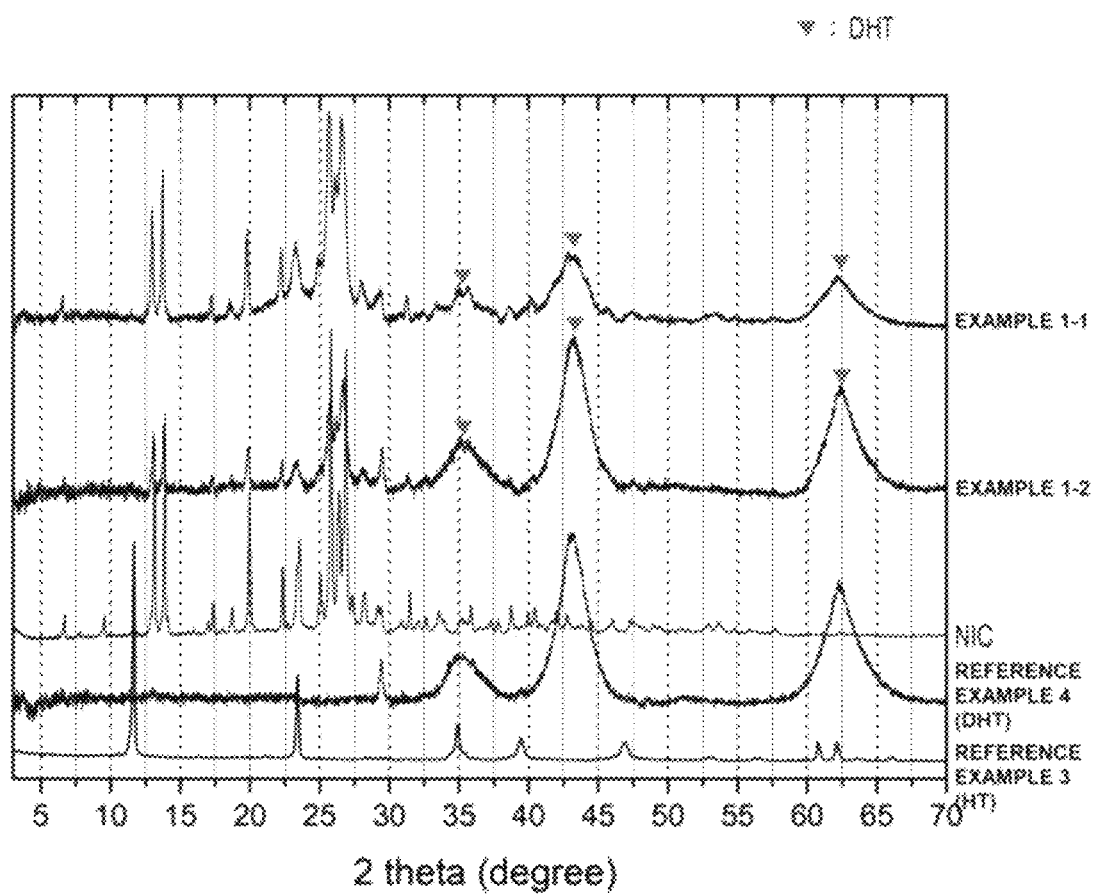
FIG. 4 illustrates an XRD graph for Example 1-1, Example 1-2, Reference Example 3, Reference Example 4, and NIC.
Figure 5:
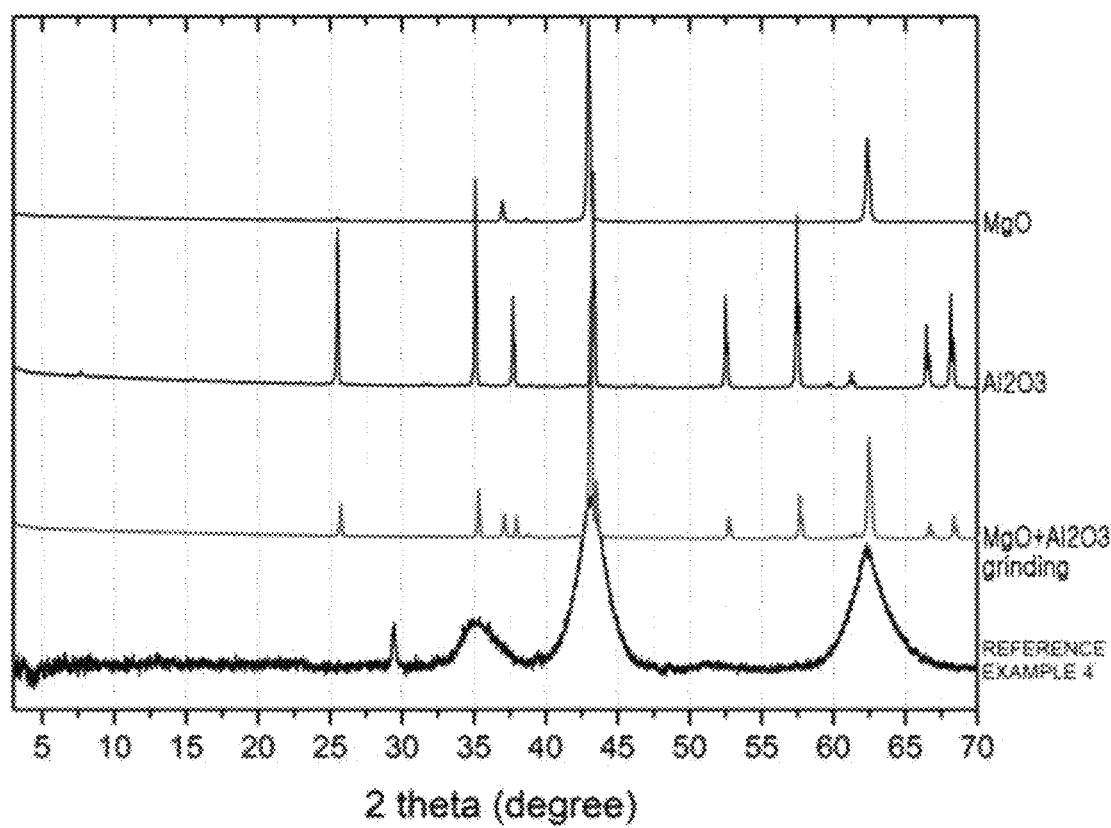
FIG. 5 illustrates an XRD graph for MgO, $Al_2O_3$, MgO+$Al_2O_3$ grinding, and Reference Example 4.
Figure 6:
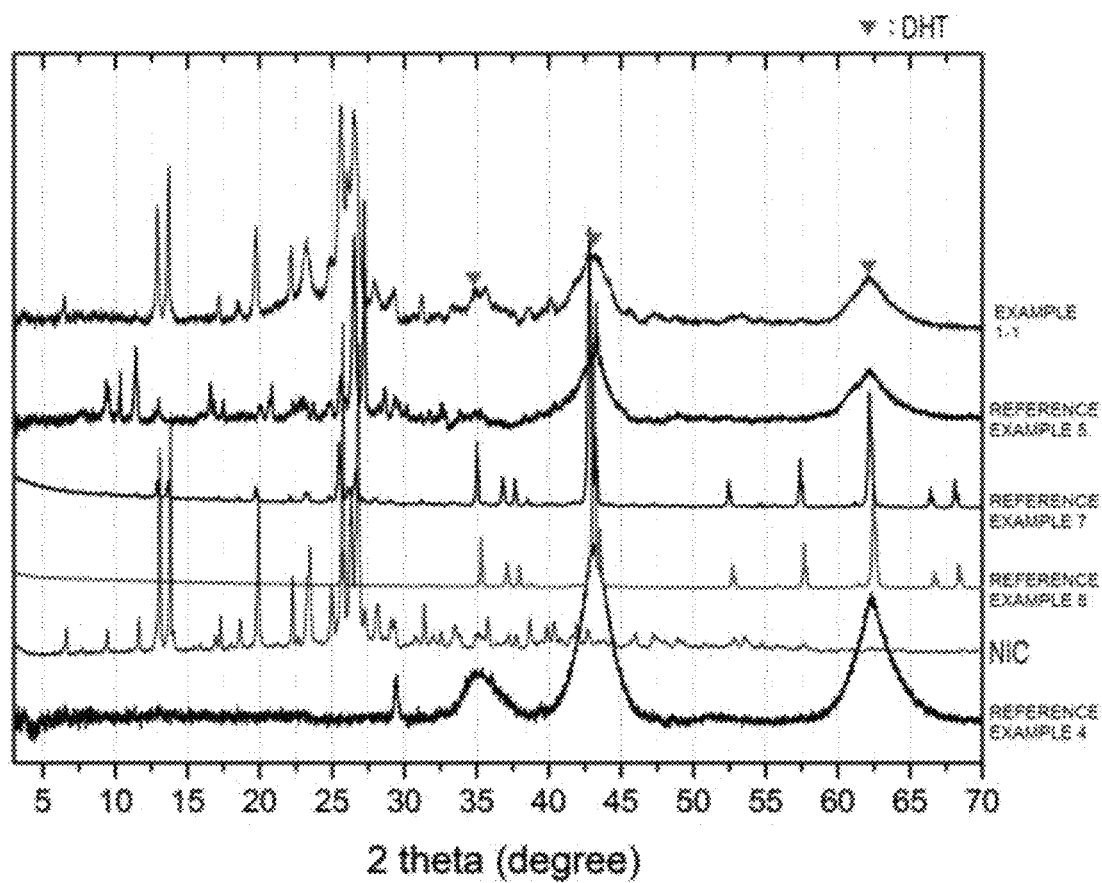
FIG. 6 illustrates an XRD graph for Example 1-1, Reference Example 4, Reference Example 5, Reference Example 7 and Reference Example 8, and NIC.
Figure 7:
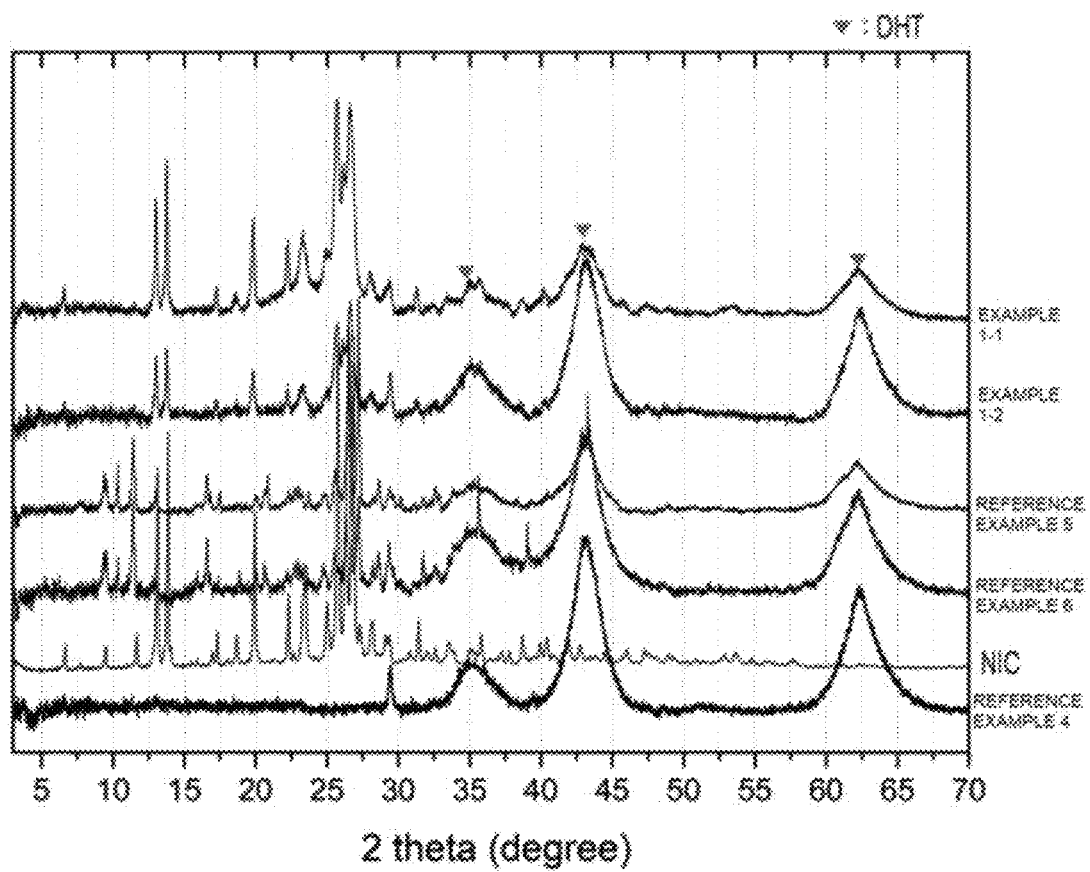
FIG. 7 illustrates an XRD graph for Example 1-1, Example 1-2, Reference Example, Reference Example 5, Reference Example 6, and NIC.

In FIG. 3, (a) is an XRD graph for NIC, (b) is for HT, (c) is for DHT, (d) is for DHT-NIC composite (* denotes impurity, ▼ denotes periclase (MgO)). Specifically, in FIG. 3, the peaks (001) having the two-dimensional characteristics of HT appeared at 11.6° (003) and 23.3° (006), respectively. These characteristic peaks are converted into broad peaks, which are pseudo-3D peaks, after being subjected to calcination at about 300° C. This conversion appears by formation of nonstoichiometric periclase of MgO containing $Al^{3+}$ ions. When looking at the XRD peak of the DHT-NIC composite after hybridizing DHT and NIC, it could be confirmed that the characteristic XRD peak values of DHT and NIC were shown.

Obvious changes such as amorphous and pseudo-3D structures could be clearly confirmed from the PXRD analysis as described above, and it can be confirmed that NIC molecules can be efficiently accommodated and protected by DHT in order to provide better solubility from these changes in XRD values. These results can be usefully used to improve antiviral efficacy in-vitro/in-vivo in future studies.

Figure 11:
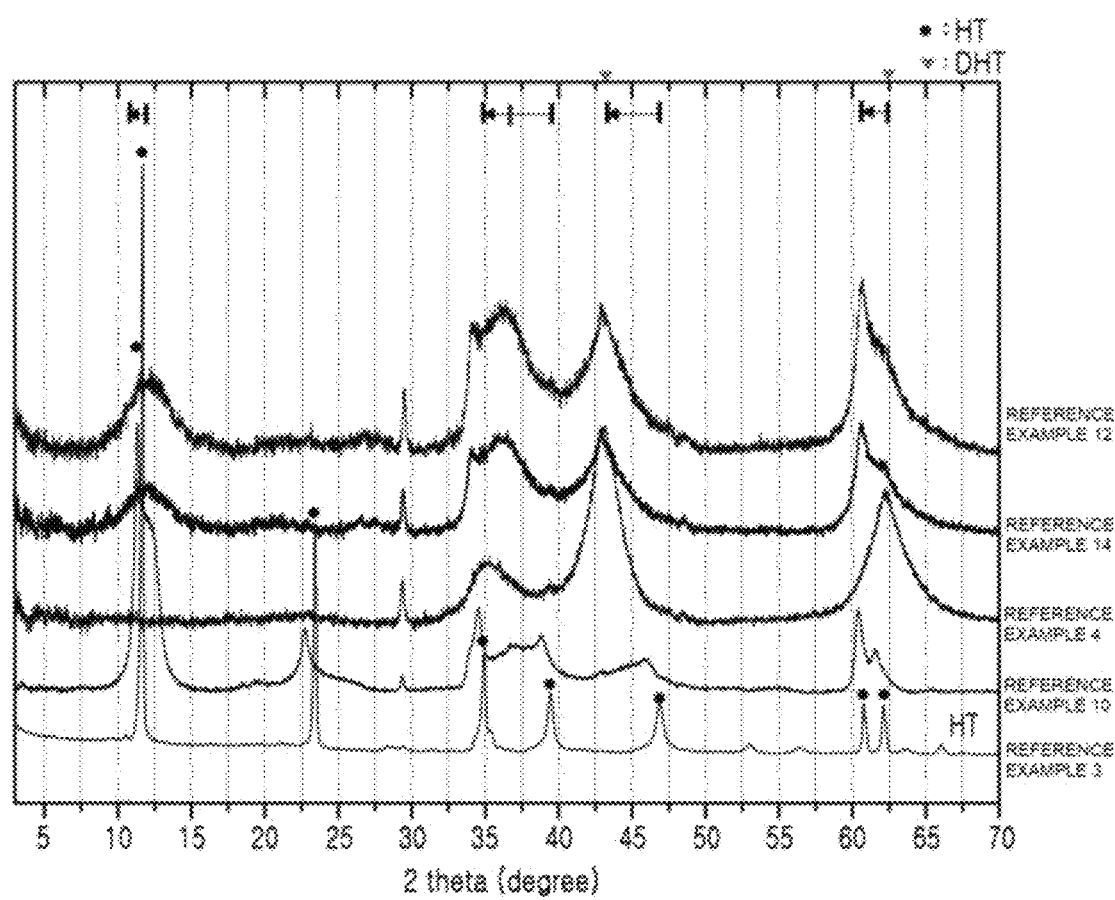
FIG. 11 illustrates an XRD graph for Reference Example 12, Reference Example 14, Reference Example 4, Reference Example 10 and Reference Example 3 (HT).

In addition, in FIG. 11, analysis of changes in the XRD graphs of Reference Example 3, Reference Example 4 and Reference Examples 12 and 14 is illustrated.

It can be confirmed that crystal structures of DHT and HT calcined at 350° C. are completely different through Reference Examples 12 and 5 and Reference Example 3 of FIG. 11. That is, HT of Reference Example 3 has very good crystallinity, peaks at 11°, 23°, 35°, 38°, 46°, 60°, and 62° representing HT appear very well, and in the case of Reference Example 4, MgO crystals are created during calcination at 350° C. and Al exists as if it being mixed between these structures, and thus have the characteristics of broad peaks at 35°, 43°, and 62° (see FIG. 10). This means that crystallinity is very low, which means that crystallinity in the c-axis direction is reduced crystallographically, and a feature that a laminated structure of HT is reduced and the specific surface area is increased, is obtained, which can be confirmed from the results of Experimental Example 4.

When water is added to the DHT (Reference Example 4) calcined at 350° C. of FIG. 11, a crystal structure reconstruction process back to the HT (Reference Example 3) structure proceeds, and as can be seen in Reference Example 12 in which water was added and reacted, the structural characteristics of DHT having broad peaks at 35°, 43°, and 62° are changed, and accordingly, phase change in the vicinity 11°, 35°, and 65° appears.

Figure 12:
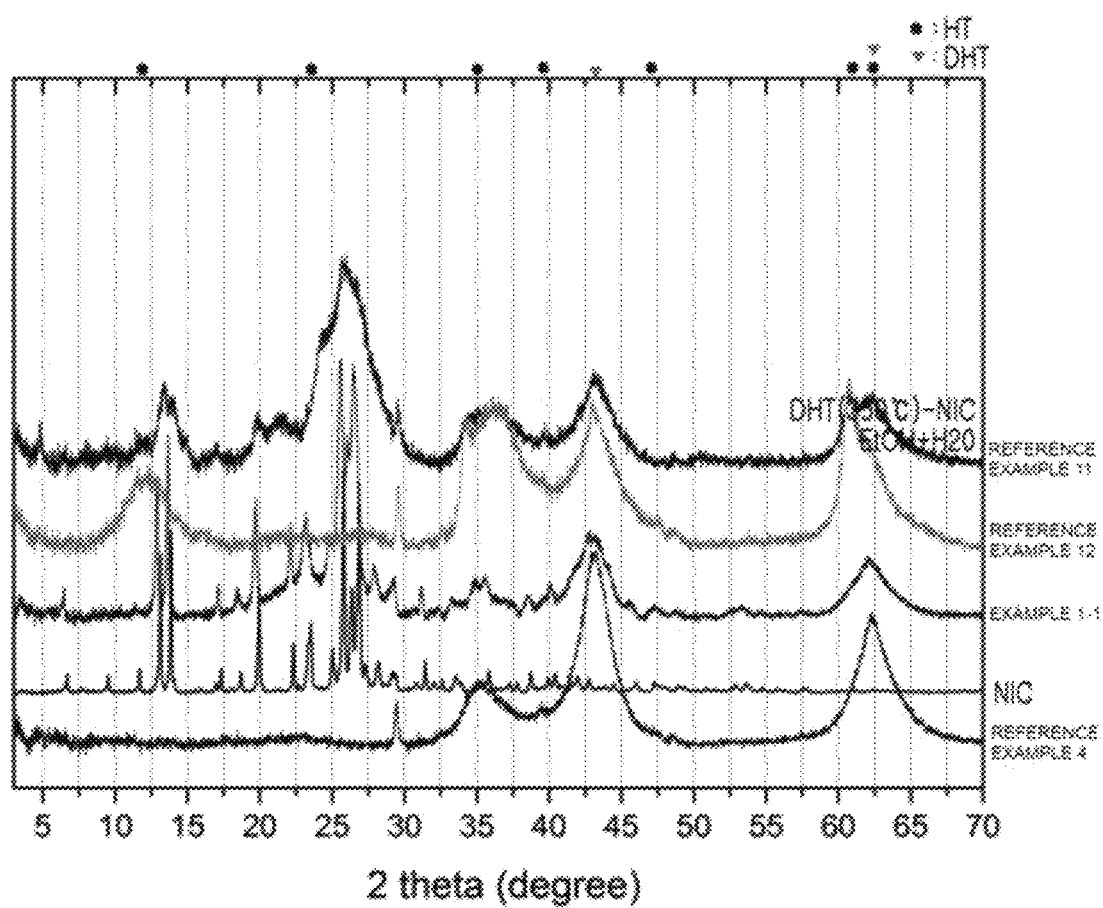
FIG. 12 illustrates an XRD graph for Reference Example 11, Reference Example 12, Example 1-1, Reference Example 4, and NIC.

This phenomenon can be confirmed through Reference Example 11 in which water was added from Example 1-1 of FIG. 12, and when looking at the peak of Example 1-1 of FIG. 12, since it takes the form of a composite in which niclosamide is reacted with the DHT structure, characteristic peaks of DHT, which has broad peaks at 35°, 43°, and 62° and niclosamide, which is an olive-colored graph, appear together. When water is added to the DHT-NIC composite of Reference Example 4, the crystal structure reconstruction process back to HT proceeds again, and in the peaks of niclosamide and DHT of Example 1-1, the crystal structure reconstruction process to HT due to the phase transition is reflected in the peaks, and as a result, it has a characteristic of changing to broad peaks, such as the phase change in the vicinity of 11°, 35°, and 65° and a peak at 20-30° of Comparative Example 2.

Experimental Example 3: TEM Analysis

Through TEM analysis, it was confirmed that the structures of the metal (hydr)oxide and the calcined metal (hydr) oxide were different. In addition, it was confirmed, through TEM analysis, that poorly soluble drugs were effectively loaded into the calcined metal (hydr)oxide.

Figure 17:
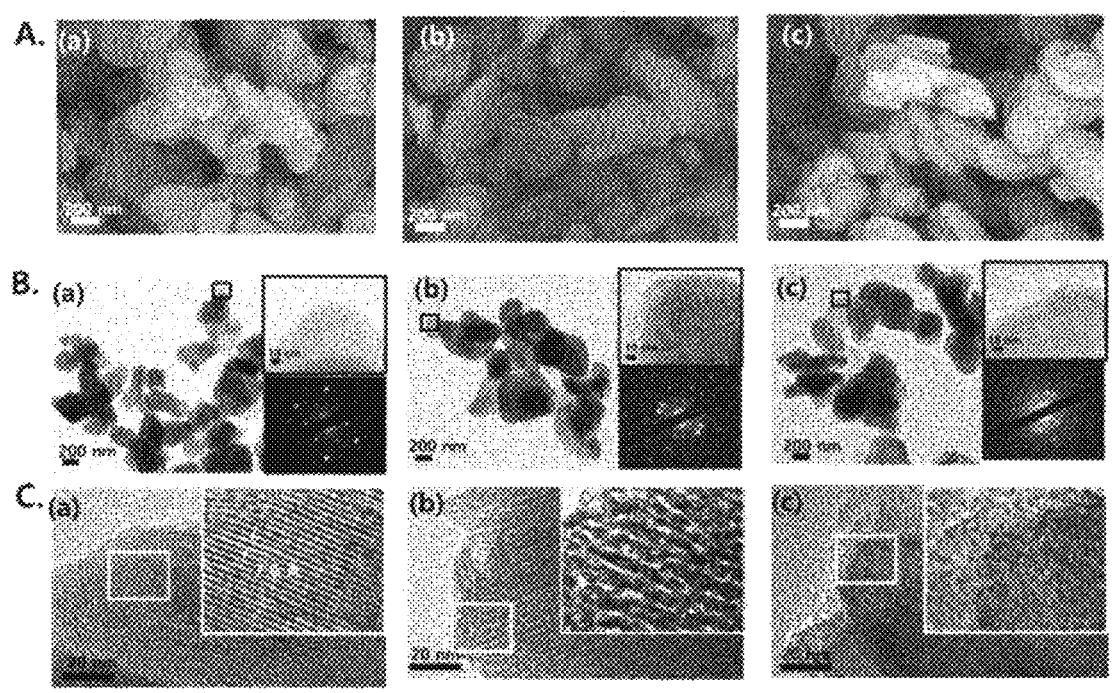
In FIG. 17, A shows field emission scanning electron microscope (FE-SEM) images, B shows TEM images, C shows TEM cross-sectional images, and (a) shows images for Reference Example 3, (b) shows images for Reference Example 4, and (c) shows images for Example 1-1.

Specifically, A of FIG. 17 illustrates FE-SEM images, and B and C illustrate TEM images. (a) of A and (a) of B of FIG. 17 are images of HT of Reference Example 3, and the structure of hydrotalcite before calcination can be confirmed. HT of Reference Example 3 has a uniform thin lamellar structure having a hexagonal single crystal diffraction pattern (selected-area electron diffraction; SAED). In (a) of C of FIG. 17, it can be confirmed the HT structure has an interlayer distance of 7.6 Å, and has a regular lattice pattern in the (001) plane (where (001) indicates crystallographically high crystallinity in the c-axis direction). This structure corresponds to the result of XRD data analysis of Reference Example 3 of FIG. 11.

On the other hand, in the case of DHT of Reference Example 4, the DHT does not have an aligned thin layer structure like HT, but adopts a chain-like or channel-like structure. This shows that HT as in Reference Example 3 was converted to magnesium and aluminum oxides after calcination. As can be confirmed from (b) of B and (c) of C of FIG. 17, the surface of DHT has a discrete structure with reduced regularity compared to HT. This seems to be due to the partial loss of carbonate and water molecules in the HT layer after calcination. The DHT of Reference Example 4 is structurally formed through a block and tunnel structure formed by being replaced along the crystallographic c-axis, and shows a SAED pattern with an intracrystalline spotty-ring as can be confirmed in the red box of (b) of B of FIG. 17, and shows a porous channel-like structure. This is thought to be a topotatic transformation due to calcination.

Compared to the DHT structure of Reference Example 4, when looking at the TEM image of the DHT-NIC composite (Example 1-1), the DHT-NIC composite has a smoother surface than the DHT structure as in (c) of B and (c) of C of FIG. 17B, and it can be confirmed that the SAED pattern has a more dispersed ring structure. This indicates the existence of atypical atoms arranged in a short range.

From the TEM images of FIG. 17, it can be confirmed that niclosamide at the molecular level was successfully filled in the porous channel structure of DHT and deposited evenly on the surface of DHT.

Experimental Example 4: Fourier Transform Infrared (FT-IR) Analysis

In order to obtain the FT-IR spectrum, a Jasco FT/IR-6100 spectrometer (Ja-325 pan) instrument was used, and a KBr disk method in transmission mode (spectral range 4000-400 $cm^{-1}$, 326 resolution 1 $cm^{-1}$, 40 scans per spectrum) was used.

The FT-IR spectra were recorded with a Jasco FT/IR-6100 spectrometer (Ja-325 pan) by the standard KBr disk method in transmission mode (spectral range 4000-400 $cm^{-1}$, 326 resolution 1 $cm^{-1}$, 40 scans per spectrum).

Figure 18:
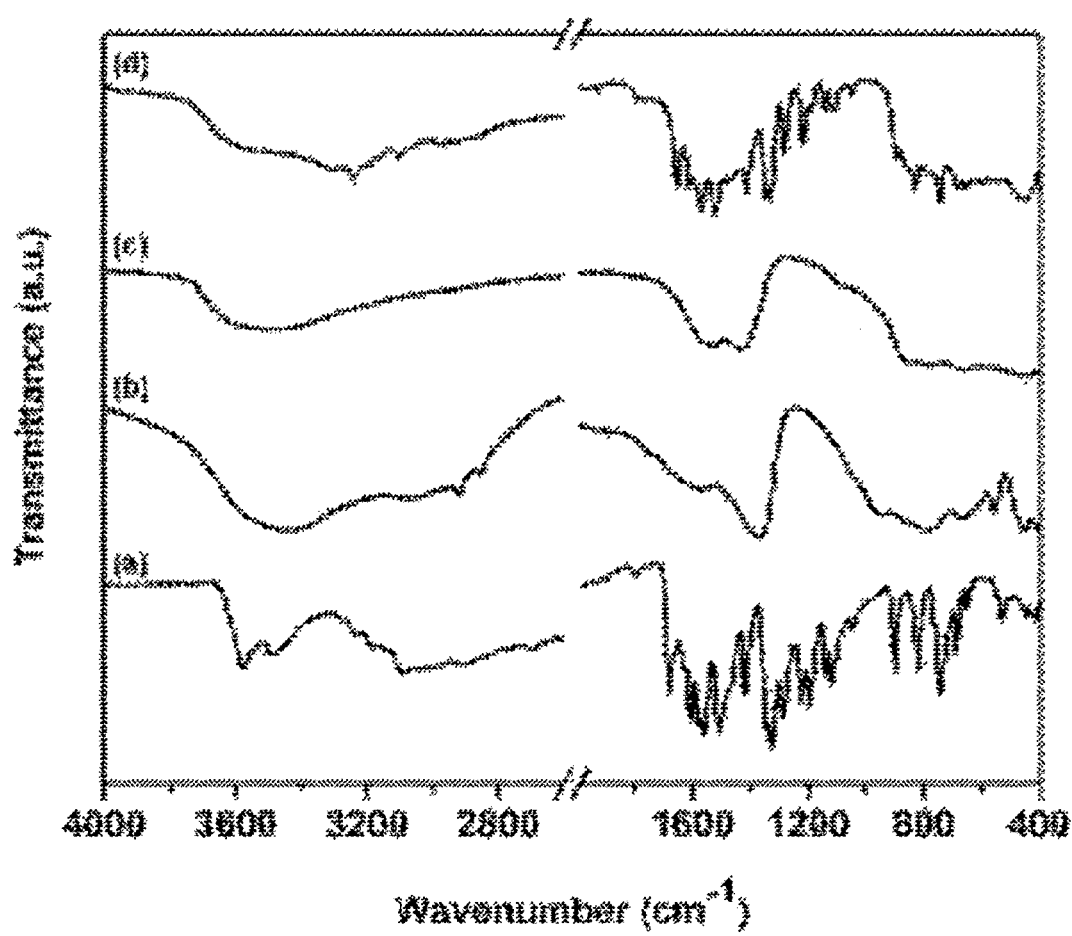
FIG. 18 illustrates a Fourier transform infrared (FT-IR) spectrum graph of NIC, HT (Reference Example 3), DHT (Reference Example 4), and DHT-NIC composite (Example 1-1).
Figure 21:
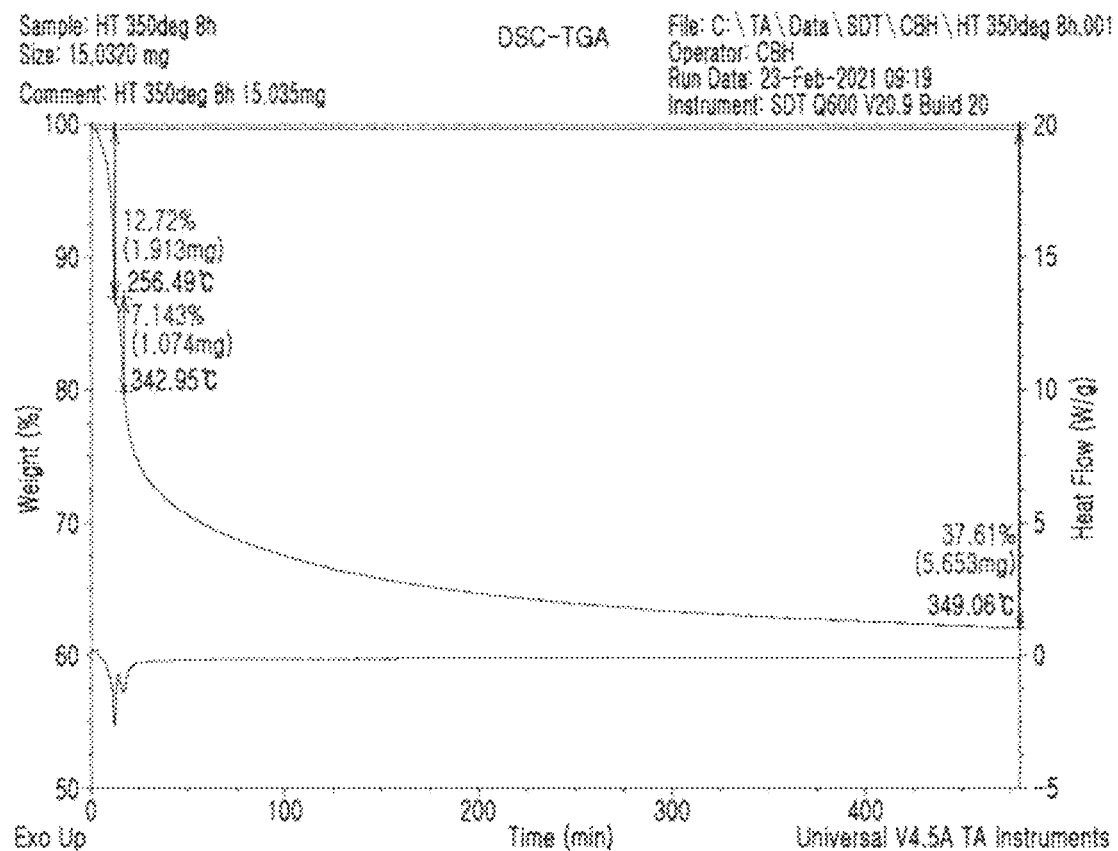
FIG. 21 illustrates a DSC-TGA graph of Example 1-1.

FIG. 18 illustrates Fourier transform infrared (FT-IR) spectra of NIC, HT (Reference Example 3), DHT (Reference Example 4), and DHT-NIC composite (Example 1-1), respectively. The characteristic peaks of NIC appeared at 3577 $cm^{-1}$, 3490 $cm^{-1}$, 1650 $cm^{-1}$, 1517 $cm^{-1}$, and 570 $cm^{-1}$, respectively, and correspond to —OH, —NH, —C=O, —$NO_2$, and C—Cl groups, respectively. In the case of HT, a broad peak appears at 3400 $cm^{-1}$, and at 1630 and 1545 $cm^{-1}$, peaks can be confirmed (see FIG. 19). The peaks may be caused by vibration of the (O—H) group by water in the hydroxide layer and the interlayer. On the other hand, the band having the characteristics of —OH as well as —$CO_3^{2-}$ is noticeably decreased after the calcination step, and this phenomenon can be confirmed by TGA and DTA analysis. Specifically, when looking at the TGA and DTA results of FIG. 21, it can be confirmed that the weight of the material changes during calcination at 350° C. for 8 hours. As the temperature rises to 256.49° C., a weight loss of 12.72% occurs, and a weight loss of 7.143% is added as the temperature rises to 342.95° C. After that, weight loss was added as calcination is proceeded at 350° C. for 8 hours, resulting in the occurrence of a total weight loss of 37.61%. It can be confirmed that physical change of HT occurs as an inflection point occurs in each temperature rise section, and it can be seen that most of the water molecules are eliminated up to the first inflection point (256.49° C.), and as it progresses to the second inflection point (342.95° C.), —OH is gradually erased and changed to form —O, and as the temperature (350° C.) is maintained, —$CO_3^{2-}$ gradually decreases (see FIG. 21). It can be seen that the peak at 1360 $cm^{-1}$ corresponding to carbonate in HT is divided into two peaks in DHT (see FIG. 19), and this phenomenon is due to the transformation of HT to DHT as described above. In addition, a remarkable phenomenon in this experiment is that the band corresponding to —OH and —NH decreases in the DHT-NIC composite structure, thereby capable of confirming that the NIC was successfully loaded into DHT.

Figure 13:
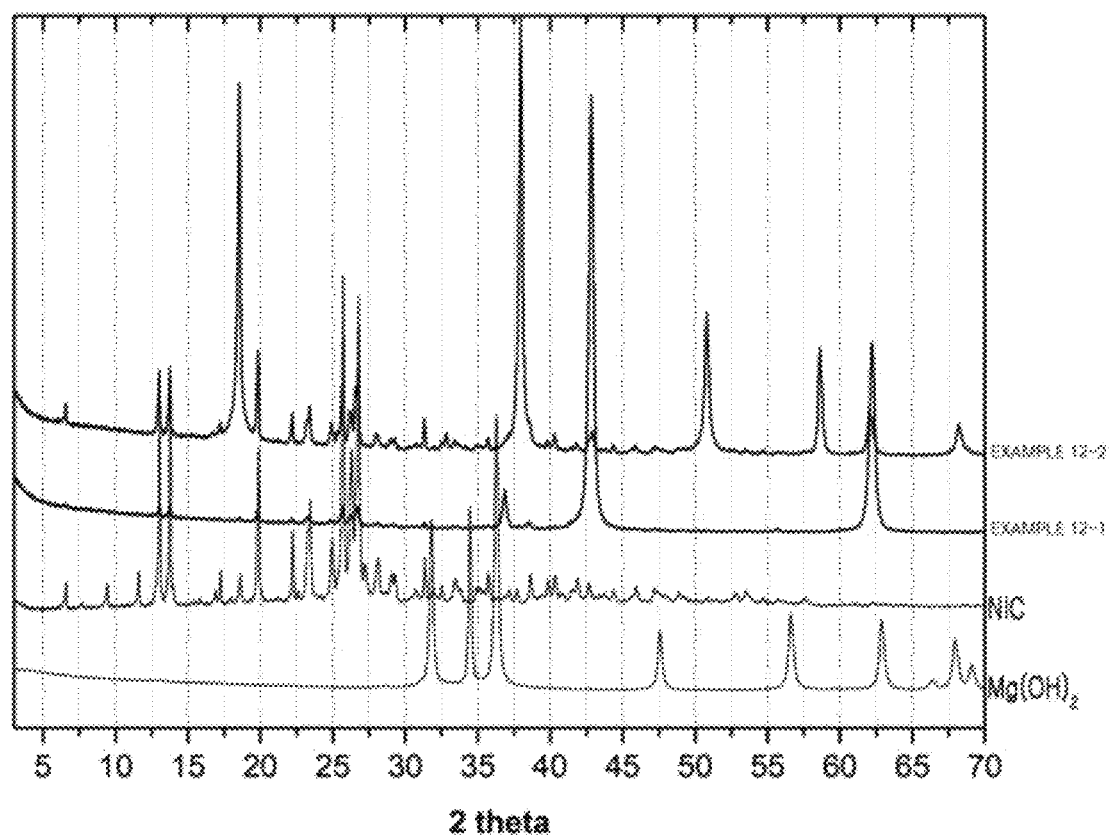
FIG. 13 illustrates an XRD graph for Example 12-1, Example 12-2, NIC, and $Mg(OH)_2$.

FIG. 13 illustrates XRD graphs for Example 12-1 (blue), Example 12-2 (red), NIC (olive), and Mg(OH)$_2$ (grey), respectively.

Figure 14:
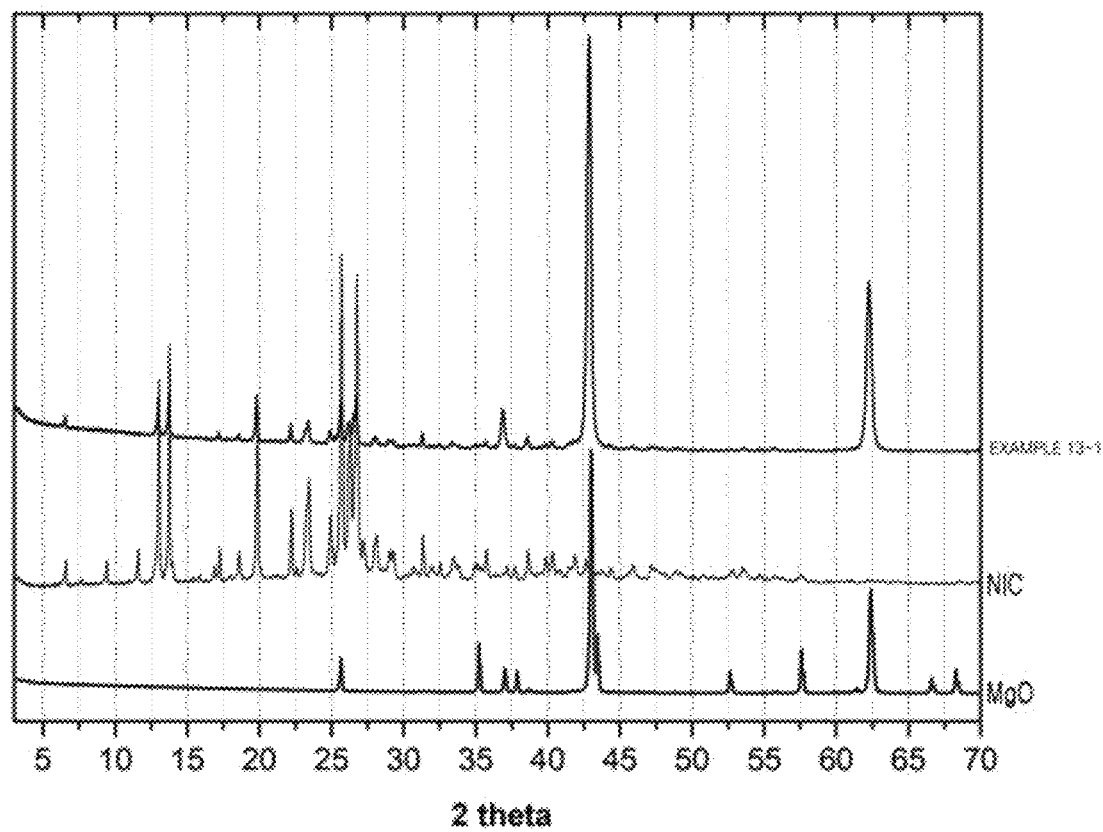
FIG. 14 illustrates an XRD graph for Example 13-1, NIC, and MgO.

FIG. 14 illustrates XRD graphs for Example 13-1 (blue), NIC (olive) and MgO (grey), respectively.

Figure 15:
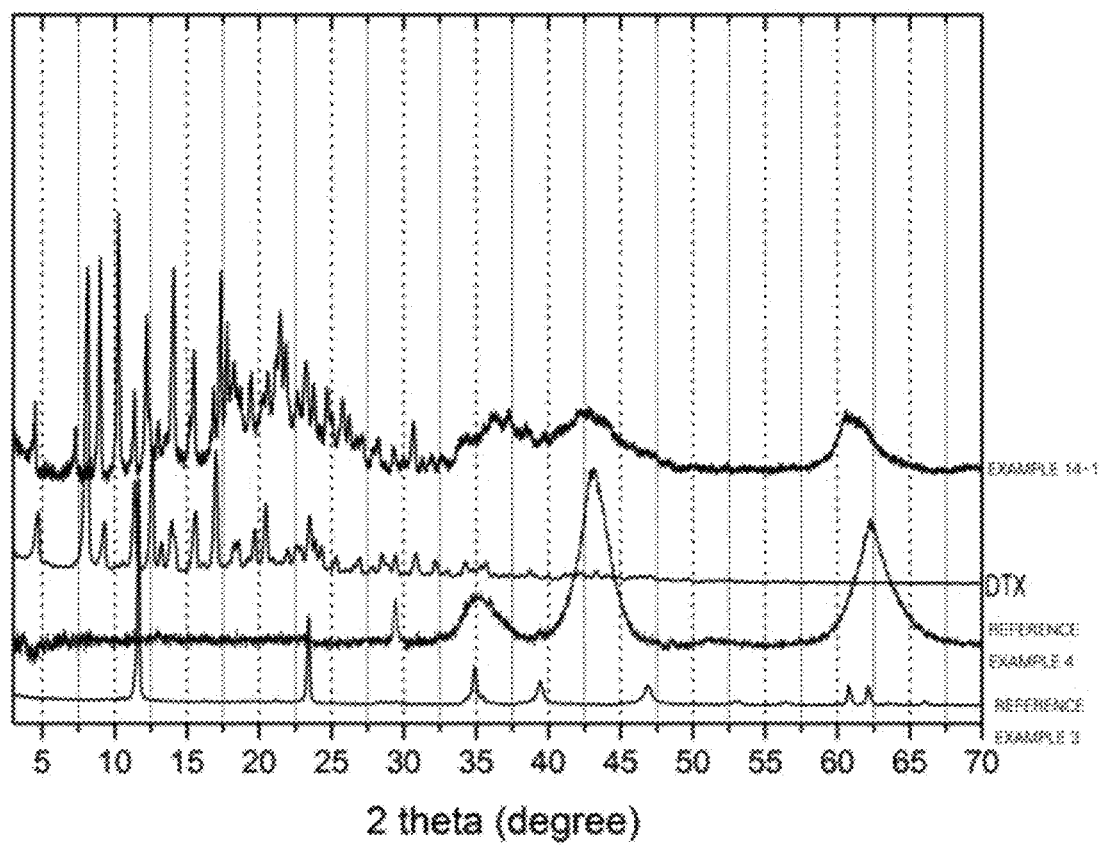
FIG. 15 illustrates an XRD graph for Example 14-1, DTX, Reference Example 4, and Reference Example 3.

FIG. 15 illustrates XRD graphs for Example 14-1 (pink), DTX (green), Reference Example 4 (gray), and Reference Example 3 (black), respectively.

Figure 16:
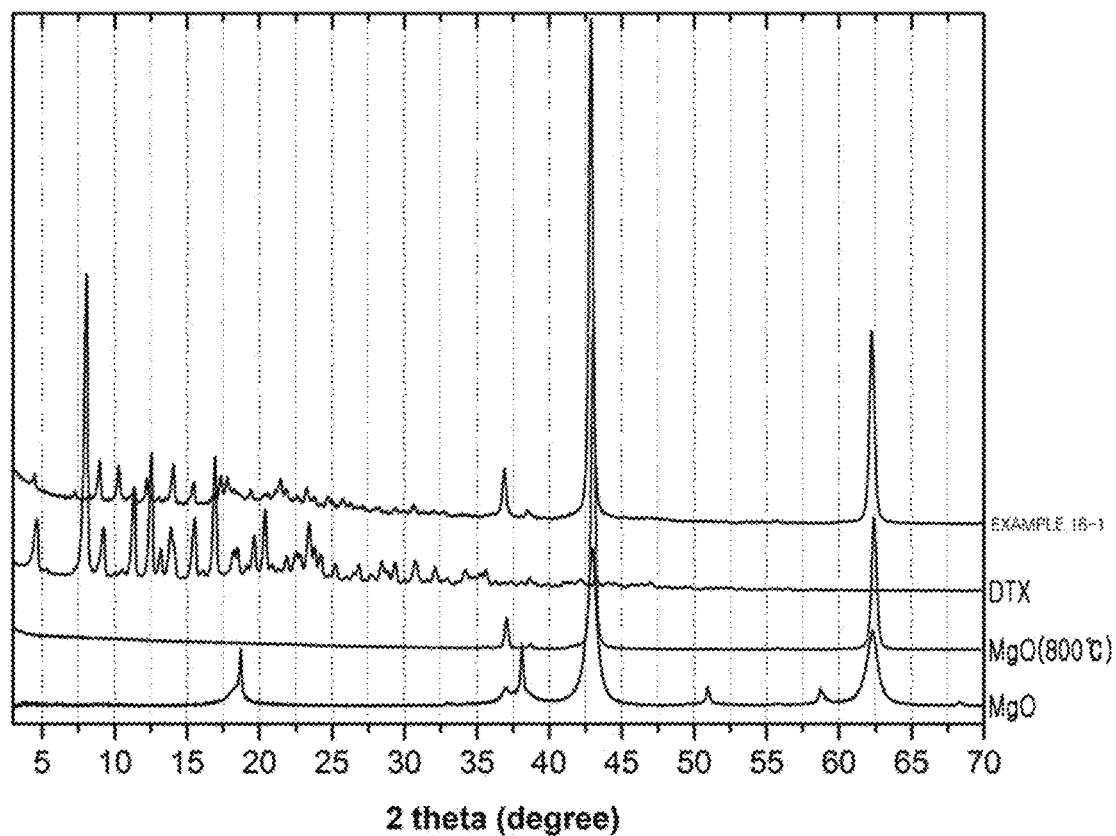
FIG. 16 illustrates an XRD graph for Example 16-1, DTX, MgO(MgO calcined at 800° C.), and MgO (uncalcined MgO).

FIG. 16 illustrates XRD graphs for Example 16-1 (blue), DTX (green), MgO (calcined MgO at 800° C.) (grey), and MgO (uncalcined MgO (black)), respectively.

Experimental Example 5: Analysis of Surface Area and Porosity

A 332 BELSORP II mini instrument (Japan) was used for an analysis of surface area and porosity, and the experiment was performed at 77K(Kelvin temperature).

For the measurement, HT and DHT were subjected to degassing at 100° C. for 6 hours, and degassing was performed on the NIC-DHT composite at room temperature for 12 hours.

Figure 22:
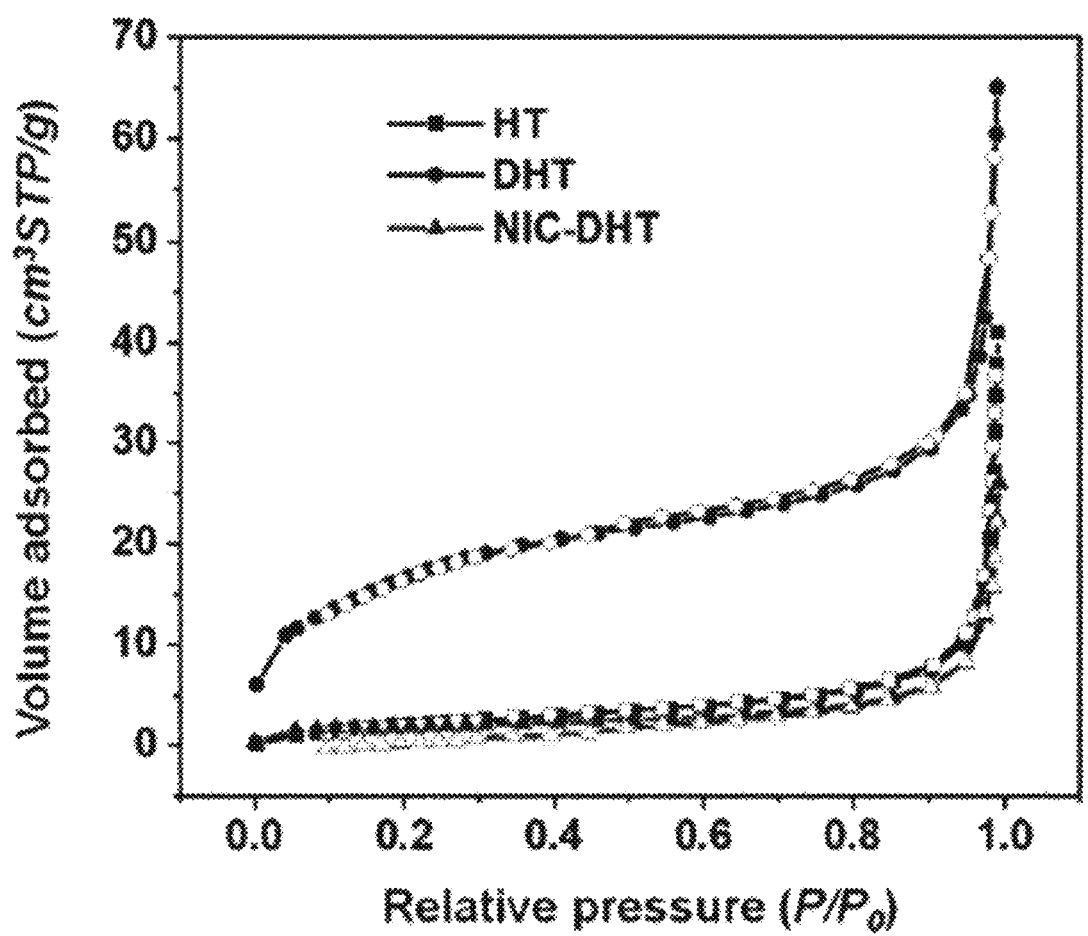
FIG. 22 illustrates a graph of nitrogen adsorption-desorption isotherms of HT (Reference Example 3), DHT (Reference Example 4), and DHT-NIC composite (Example 1-1).

FIG. 22 illustrates graphs of nitrogen adsorption-desorption isotherms of HT (Reference Example 3), DHT (Reference Example 4), and DHT-NIC composite (Example 1-1).

The surface area $S_{BET}$ and total pore volume ($V_p$) values of each of the HT, DHT, and DHT-NIC were calculated from the adsorption isotherms of FIG. 22 using the BET method and are listed in Table 7. Since DHT of Reference Example 4 corresponds to the calcined form, it was confirmed that the DHT had a very large surface area value compared to HT of Reference Example 3 which was not calcined. This is because the DHT takes a structure in which the surface area is concave-convex by calcination. Therefore, the total pore volume increased from 0.0061 to 0.0099 with the change from HT to DHT. On the other hand, the surface area value and total pore volume value of the DHT-NIC composite were lowered compared to that of DHT, which is thought to be because the NIC molecules were attached to the surface of DHT having a non-uniform surface pattern.

TABLE 7

| Classification | $S_{BET}$ (m²/g) | $V_p$ (cm³/g) |
|---|---|---|
| Reference example 3 (HT) | 9.05 | 0.0061 |
| Reference example 4 (DHT) | 62.18 | 0.0099 |
| Example 1-1 (DHT-NIC composite) | 6.85 | 0.0035 |

In Table 7, $S_{BET}$ is the specific surface area value calculated by being corrected with the BET equation, and $V_p$ is the total pore volume calculated from an adsorption amount at P/P0=0.99.

Experimental Example 5: FE-SEM Analysis

For the observation of HT, DHT, and NIC-DHT using FE-SEM, a Sigma 300 (Carl 328 Zeiss, Germany) field-emission scanning electron microscope was used.

Figure 23:
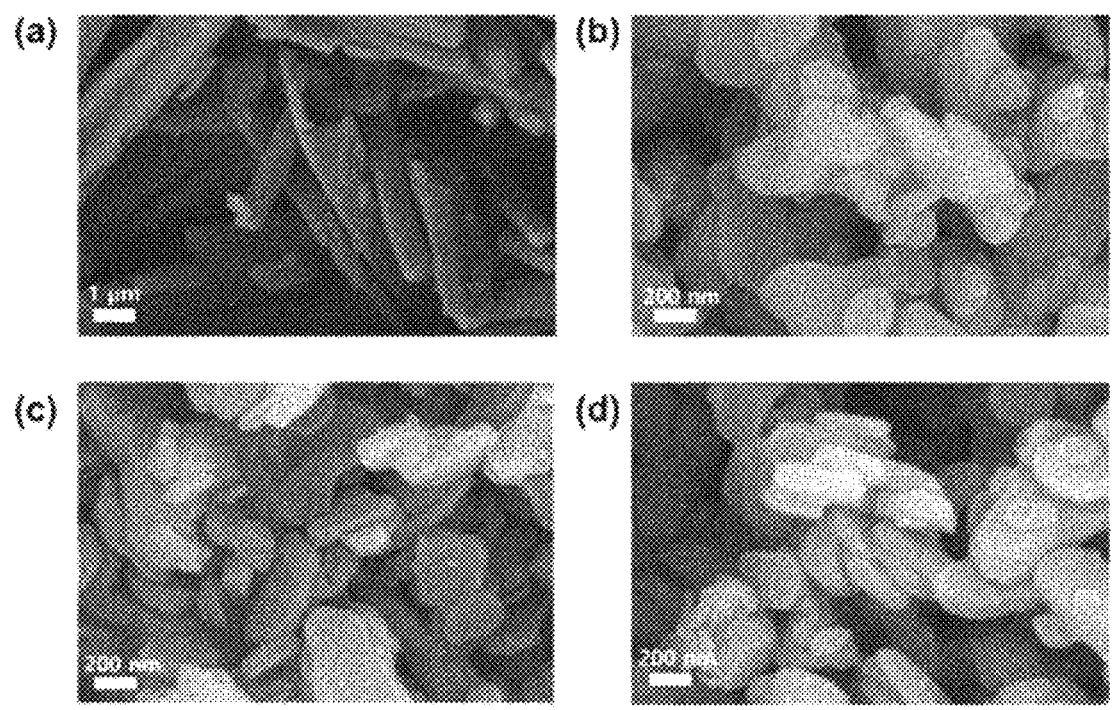
FIG. 23 illustrates field emission scanning electron microscope (FE-SEM) images of HT (Reference Example 3), DHT (Reference Example 4), and DHT-NIC composite (Example 1-1).

FIG. 23 illustrates field emission scanning electron microscope (FE-SEM) images of HT (Reference Example 3), DHT (Reference Example 4), and DHT-NIC composite (Example 1-1), respectively. HT has a plate-like shape with a smooth surface and has a diameter of ~300 nm. The structure described above means the most typical form of a layered material. When looking at the form of DHT, which is a form obtained by calcining the HT, the average particle size of the HT form was almost maintained, but the surface of DHT was more rough than the smooth surface state of the HT, and this change in surface state is thought to be due to the dehydration and decarbonation reactions of HT that occur in the calcination step. On the other hand, it was confirmed that the form of the DHT-NIC composite almost maintained the form of DHT, but the DHT-NIC composite had a non-uniform surface compared to the form of DHT and HT. This is thought to be due to surface adsorption of NIC particles.

Experimental Example 6: Particle Size Analysis

A Particle size analyzer (ELSZ-330 2000ZS; Otsuka, Japan) was used for particle size analysis, and HT, DHT, and NIC-DHT were dispersed in 99.9% ethanol and measured. Measurements were performed in triplicate.

Figure 24:
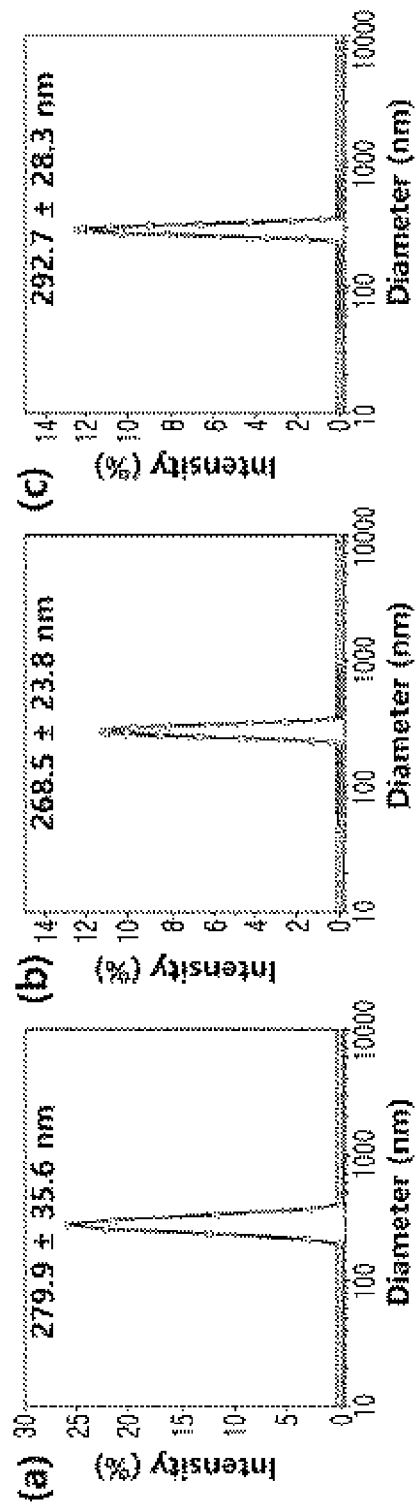
FIG. 24 illustrates graphs for result values by a dynamic light scattering (Dynamic light scattering) analysis, and (a) is a graph of average particle size distribution of HT (Reference Example 3), (b) is a graph of the average particle size distribution of DHT (Reference Example 4), and (c) is a graph of the average particle size distribution of the DHT-NIC composite (Example 1-1).

The result of dynamic light scattering analysis is illustrated in FIG. 24. The average particle sizes of HT (Reference Example 3), DHT (Reference Example 4), and DHT-NIC composite (Example 1-1) were 279.9±35.6, 268.5±23.8, and 292.7±28.3, respectively, and showed similar sizes, and these results are also consistent with the FE-SEM analysis results of Experimental Example 5.

Since the average particle size was in the range of <300 nm (by DLS and FE-SEM analysis), it was confirmed from these results that all of the molecules can be ideally used as anti-viral therapeutic agents. This is because the SARS-CoV-2 virus has a small particle size (50-150 nm), and thus the DHT-NIC composite, which the present inventors are targeting, should also be able to penetrate the virus-infected cell, and penetrate into the cell to exert an anti-viral effect.

The research team established a potential endocytosis mechanism involving hydrotalcite from previous studies. Therefore, if drugs are administered orally or parenterally, it was confirmed that it is very important to protect a drug candidate group that is easily eliminated such as NIC. In most cases reported, it was confirmed that NIC has very low plasma concentrations after oral administration. Therefore, in oral or parenteral administration methods, protecting the NIC using an ideal nanocarrier such as calcined metal (hydr)oxide may help to enhance the therapeutic effect of the NIC.

Experimental Example 8: In-Vivo Pharmacokinetic Analysis of Pharmaceutical Composition Containing Metal (Hydr) Oxide-Niclosamide Composite In-vivo pharmacokinetic analysis was performed using the DHT-NIC composite or MgO-NIC composite. The in-vivo pharmacokinetic analysis was proceeded in a way of performing a single oral administration of pharmaceutical compositions using the DHT-NIC composite or MgO-NIC composite (forms of Examples 5 to 11, or Examples 20 to 22, and 23-1 to 23-3) to hamsters or rats, and plasma drug concentration information was obtained after proceeding the single oral administration in this way.

The experiment was proceeded by administering the composition of Example 5 at doses of 50 mg/kg and 200 mg/kg, respectively. In the case of a higher dose of 200 mg/kg, the experiment was proceeded by confirming the validity of the dosage form so that the dose could be used in vivo. For the compositions of Examples 20 to 22 and Examples 23-1 to 23-3, the experiment was proceeded by administering each composition at dose of 30 mg/kg to rats.

Figure 25:
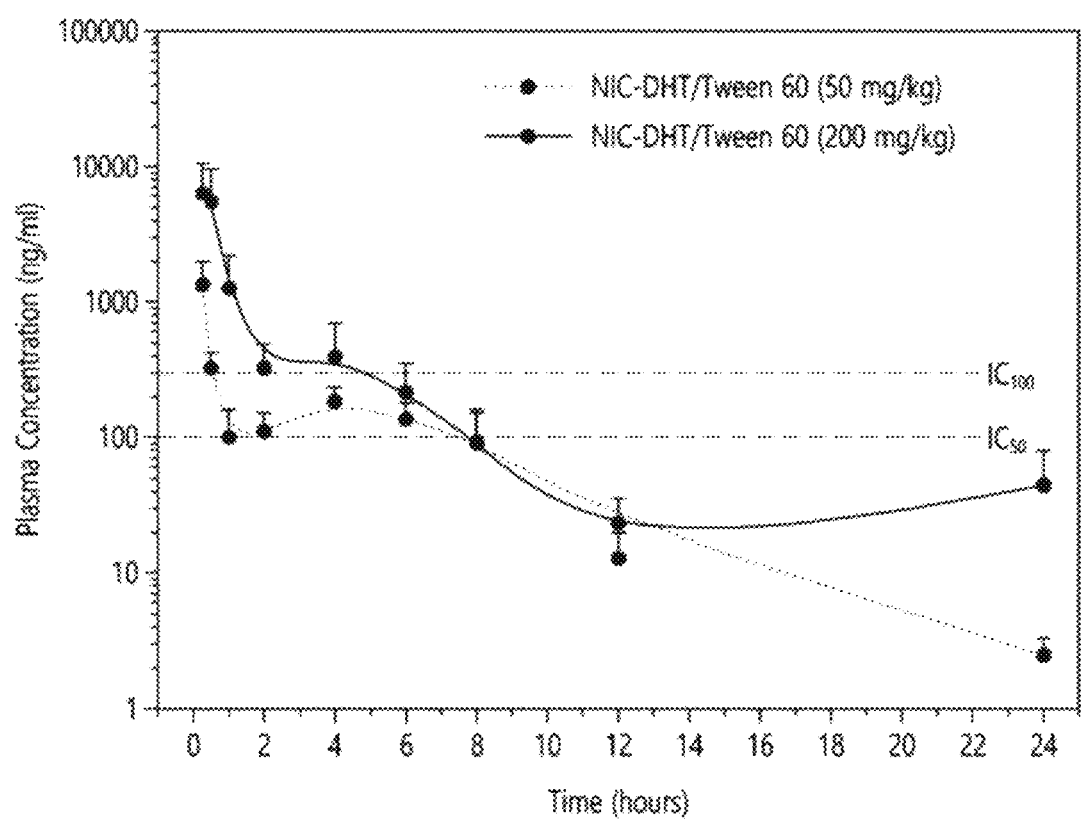
FIGS. 25-35 illustrate graphs of NIC concentrations in plasma over time.
Figure 39:
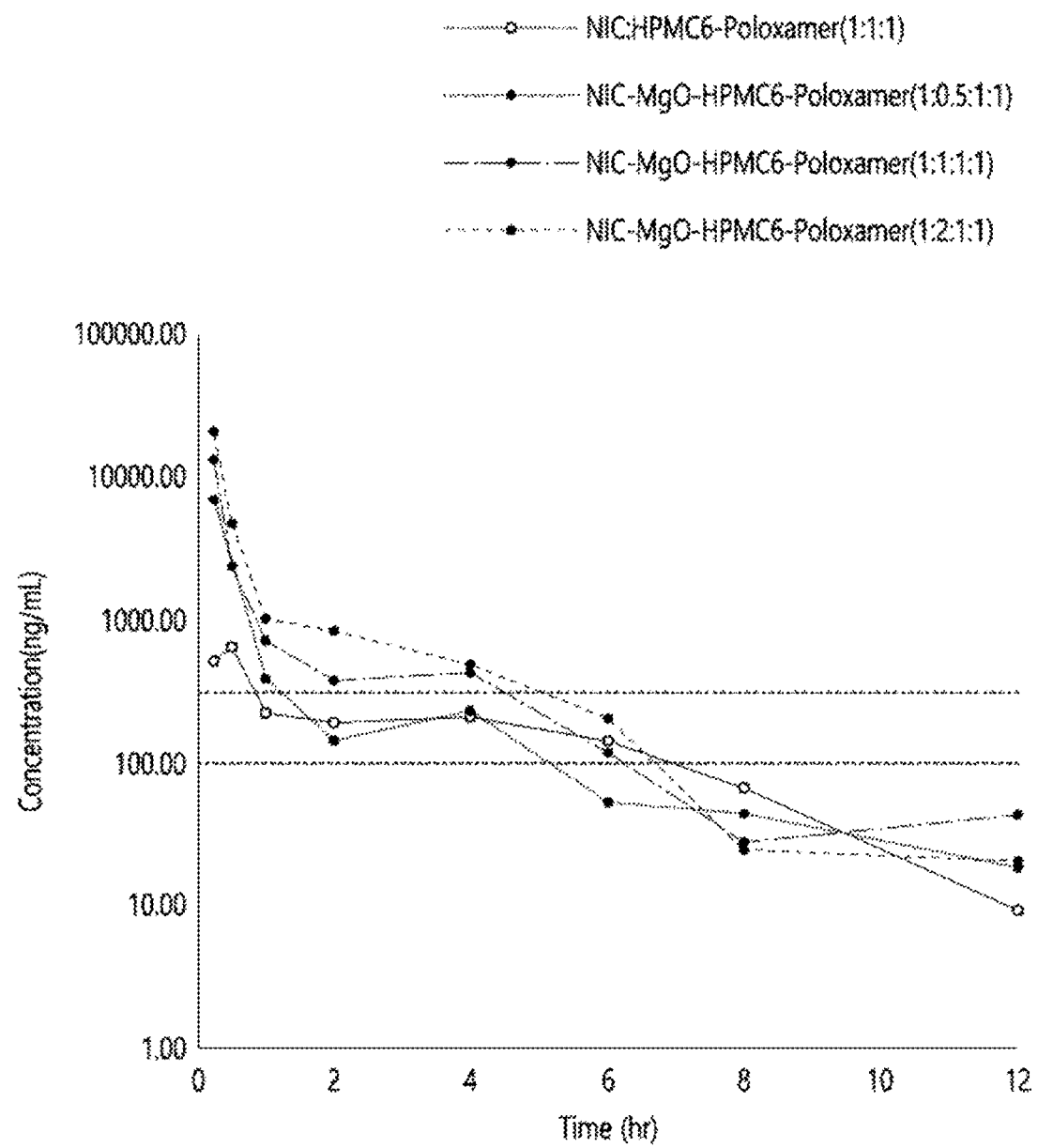
FIG. 39 illustrates a graph for NIC concentration in plasma over time for Example 20 NIC:MgO:HPMC6:poloxamer (1:0.5:1:1)), Example 21 (NIC:MgO:HPMC6:poloxamer (1:1:1:1)), Example 22 (NIC:MgO:HPMC6:poloxamer (1:2:1:1)) and Comparative Example 5 (NIC:HPMC6:poloxamer (1:1:1)).
Figure 40:
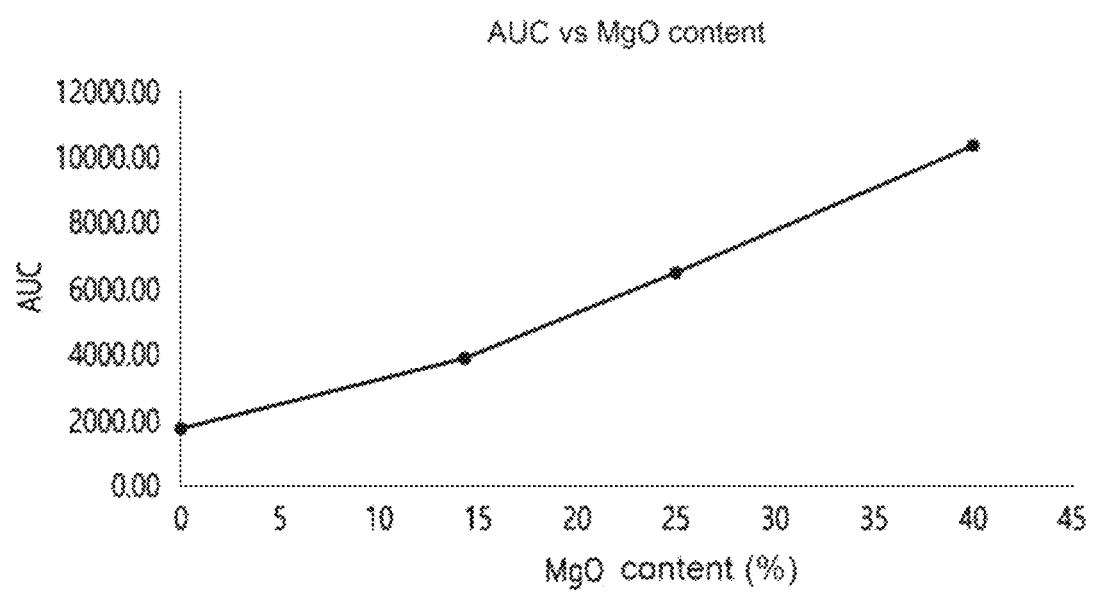
FIG. 40 illustrates a graph for AUC tendency according to the increase of MgO content for Examples 23-1, 23-2 and 23-3.

The results of administration of Example 5 in the above analysis are illustrated in FIG. 25. The results of administration of Examples 20 to 22 are illustrated in FIG. 39, and the results of administration of Examples 23-1 to 23-3 are illustrated in FIG. 40. The graph of FIG. 25 illustrates an NIC concentration in plasma over time in rats. The most important pharmacokinetic parameters are listed in Table 8 below.

TABLE 8

| Parameters | **Yomesan ® (50 mg/kg) | NIC-DHT/Tween 60 (50 mg/kg) | NIC-DHT/Tween 60 (200 mg/kg) |
|---|---|---|---|
| $AUC_{(last)}$ (ng · h/mL) | 1096.81 ± 359.28 | 1823.83 ± 305.26 | 6819.30 ± 2530.40 |
| $C_{max}$ (ng · h/mL) | 155.27 ± 39.92 | 1350.37 ± 613.98 | 6316.60 ± 4270.00 |
| $T_{max}$ (h) | 4.00 ± 0.89 | 0.25 ± .000 | 0.25 ± 1.65 |
| $T_{1/2}$ (h) | 5.72 ± 6.09 | 3.19 ± 0.43 | 2.69 ± 1.46 |

AUC = area under the plasma concentration-time curve; $C_{max}$ = maximum plasma concentration; $T_{max}$ = time required to reach $C_{max}$, $t1_{/2}$ = elimination half-life It could be confirmed that the AUC value of the DHT-NIC composite/Tween 60 formulation was 1823.83±305.3 ng·h/mL, which was about 1.8 times higher than that of Yomesan, which is a commercially available NIC drug. In addition, the $C_{max}$ value of the DHT-NIC composite/Tween 60 formulation was about 1350.4±614.0 ng·h/mL, which appeared after 0.25 hours after oral administration. Therefore, the $T_{max}$ value of the DHT-NIC composite/Tween 60 formulation was about 16 times shorter than that of Yomesan, and in the case of Yomesan, the $C_{max}$ value at 4 hours of the $T_{max}$ value was about 155.3±39.9 ng·h/mL.

The PK profile in Table 8 suggests that sequential optimization is possible by changing the ratio of NIC to DHT and the dosage of the NIC-DHT composite. It was confirmed that the $C_{max}$ value was significantly improved when the dosage was increased from 50 mg/kg to 200 mg/kg. In addition, it was confirmed that the value of AUC increased by about 4 times due to the increase of the dosage. However, it was confirmed that the time required for the NIC to maintain a plasma concentration greater than or equal to the $IC_{50}$ value did not change and the plasma concentration was maintained for about 8 hours.

Figure 26:
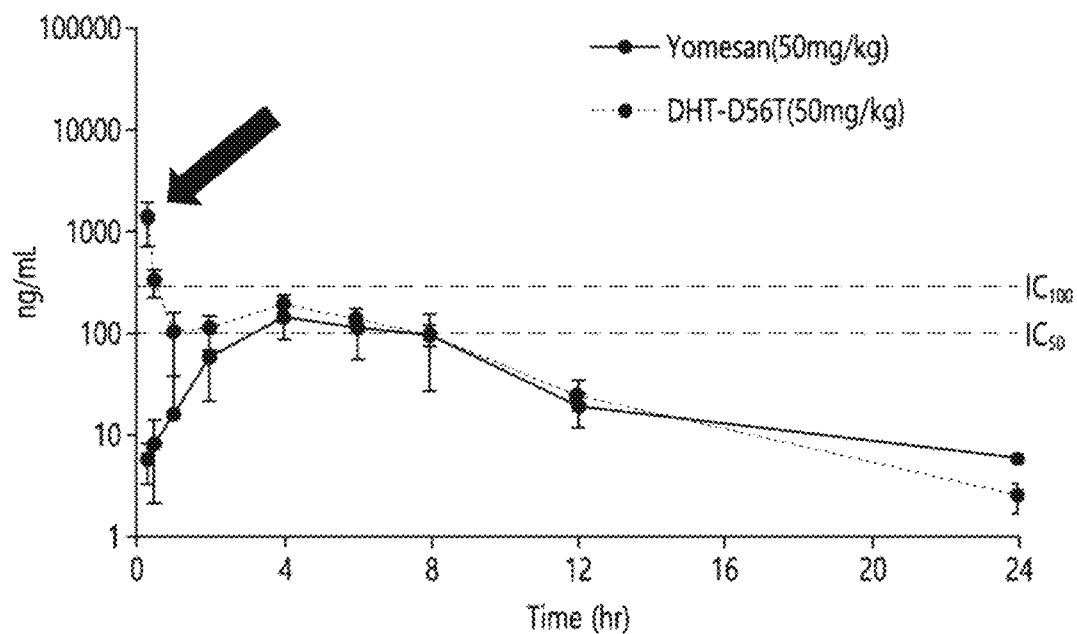

From the above result values, the comparison values with Yomesan are illustrated in FIG. 26.

Figure 27:
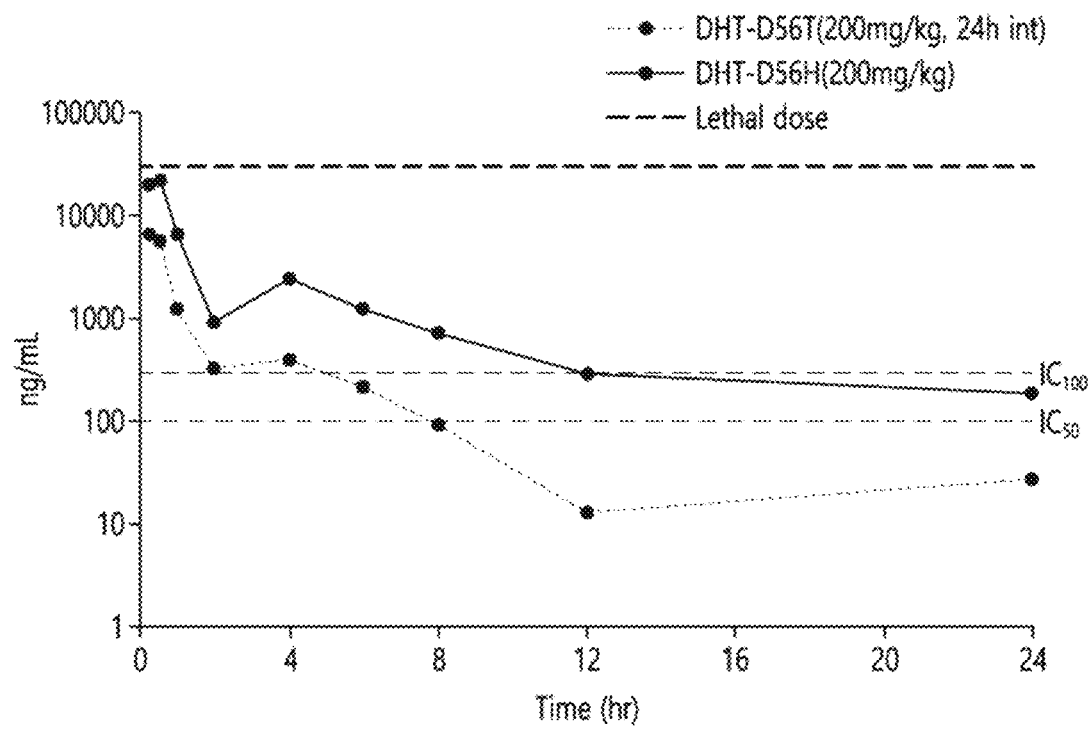

In addition, in the above analysis, the effect values on the change of the types of surfactants are described in FIG. 27. When the composition was prepared by exchanging the surfactant from Tween 60 (Example 9) to HPMC (Example 6), it was confirmed that the $C_{max}$ value was enhanced by 3.9 times and the AUC value by 4.7 times.

Figure 28:
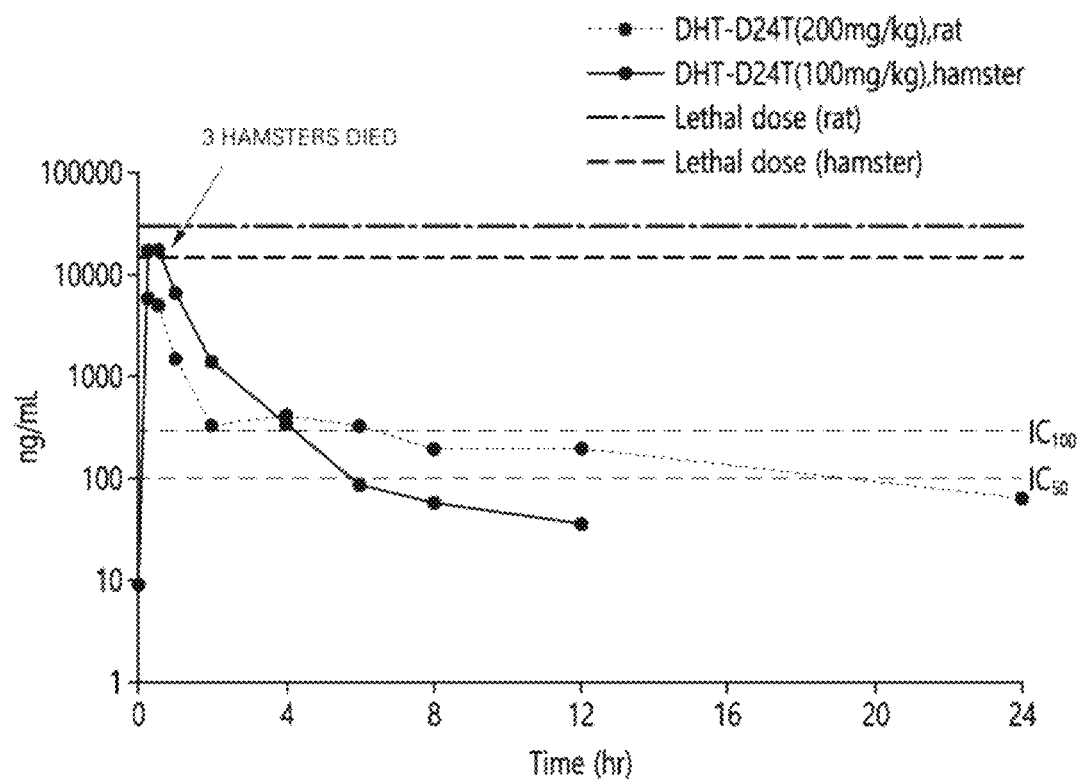

FIG. 28 illustrates result values for comparison between species of hamster and rat. It was confirmed that even if the same drug was administered, the change of the drug concentration in the blood showed a different pattern depending on the animal species. The composition of Example 11 was administered to hamsters and rats at different weights, respectively. The rats were administered at a weight of 200 mg/kg, and the hamsters were administered at a weight of 100 mg/kg. It was confirmed that a drug concentration in blood of 100 ng/mL was maintained for more than 12 hours in rats, but a drug concentration in blood of 100 ng/mL was maintained in hamsters for only about 6 hours.

Figure 29:
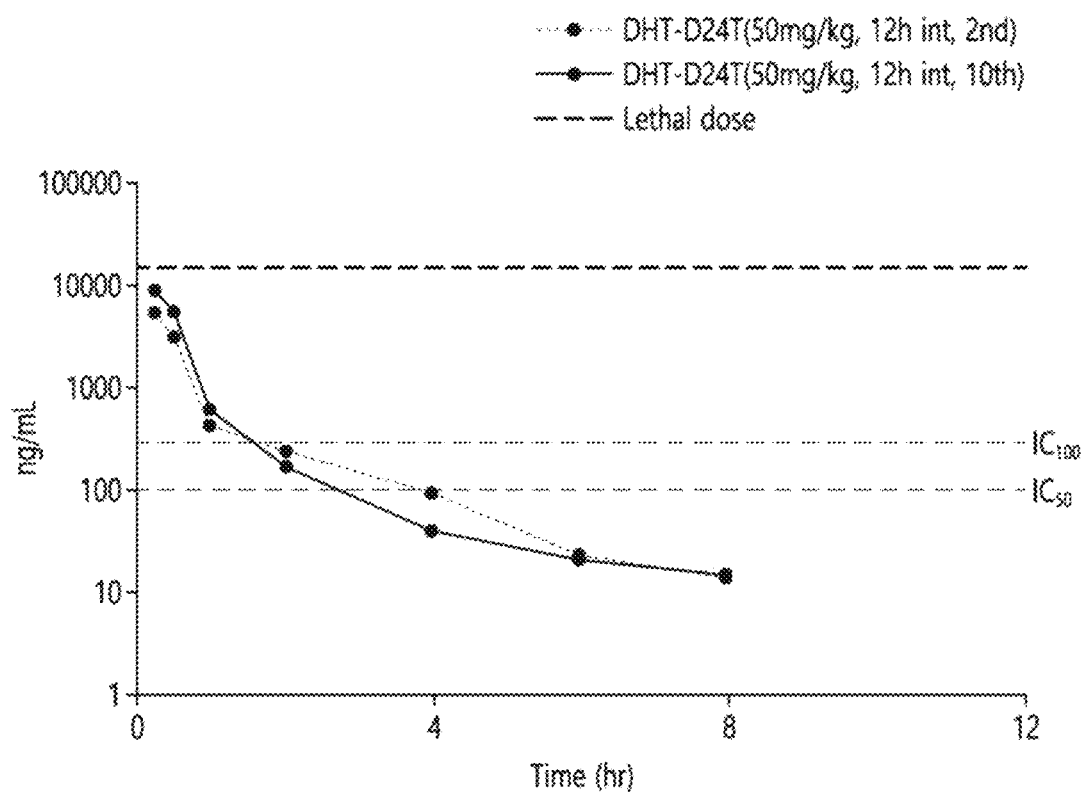

FIG. 29 illustrates a graph of the results of change of the drug concentration in blood according to the number of administrations. A group in which the composition of Example 11 was administered to hamsters twice at 12 hour intervals and a group administered 10 times at 12 hour intervals were respectively measured. In this study, it was confirmed that patterns of drug concentration in blood were formed similarly regardless of the number of administrations.

Figure 30:
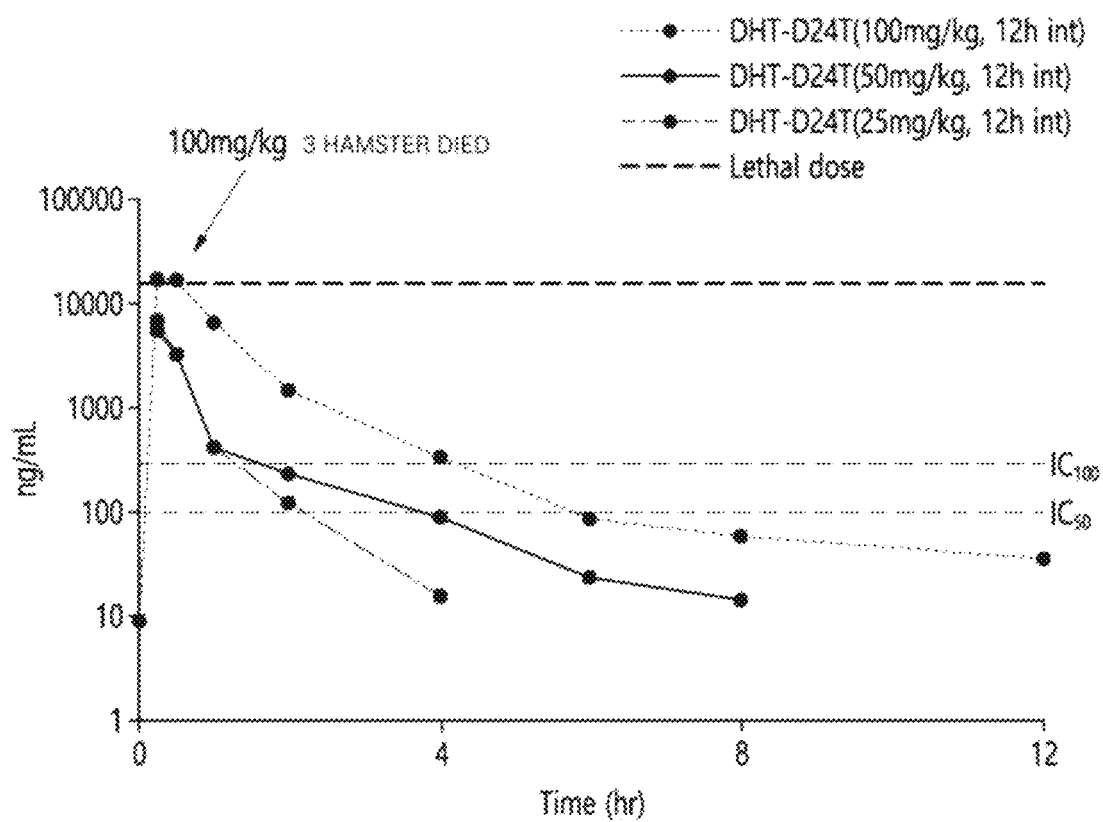

FIG. 30 illustrates a graph of the results of the patterns of drug concentration in blood according to the dose of the composition. The composition of Example 11 was classified into doses of 25 mg/kg, 50 mg/kg and 100 mg/kg, respectively, and administered to the hamsters. According to the results of FIG. 30, it was confirmed that the $C_{max}$ and AUC values increase or decrease in proportion to the dose of the composition.

Figure 31:
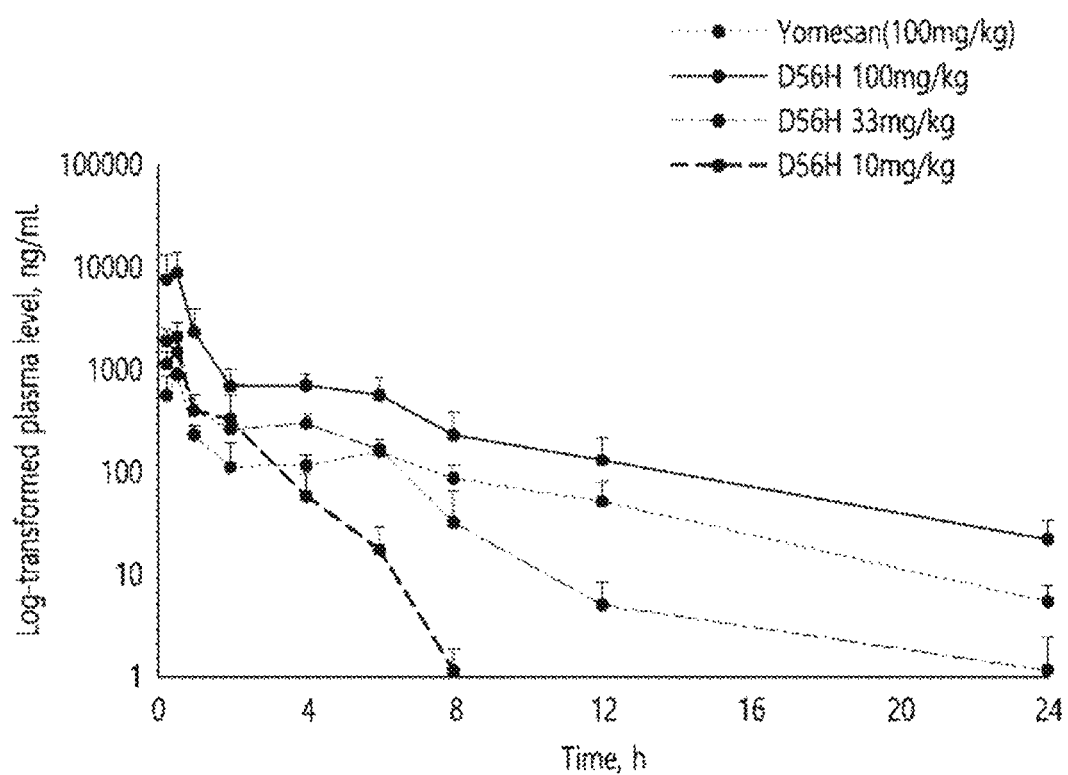

FIG. 31 illustrates a graph of the results of the patterns of drug concentration in blood according to the dose when the composition of Example 6 of the present invention is administered to rats. According to FIG. 26, it was confirmed that the composition of Example 6 of the present invention showed an AUC value similar to that of Yomesan but the $C_{max}$ value was about twice as high at a dose 1/10 smaller than that of Yomesan, and had an effect of about 5 times higher in AUC and about 10 times higher in $C_{max}$ at the same dose as Yomesan. In addition, in the case of Example 6, it was confirmed that as the dose increased, the AUC and $C_{max}$ values increased.

Figure 32:
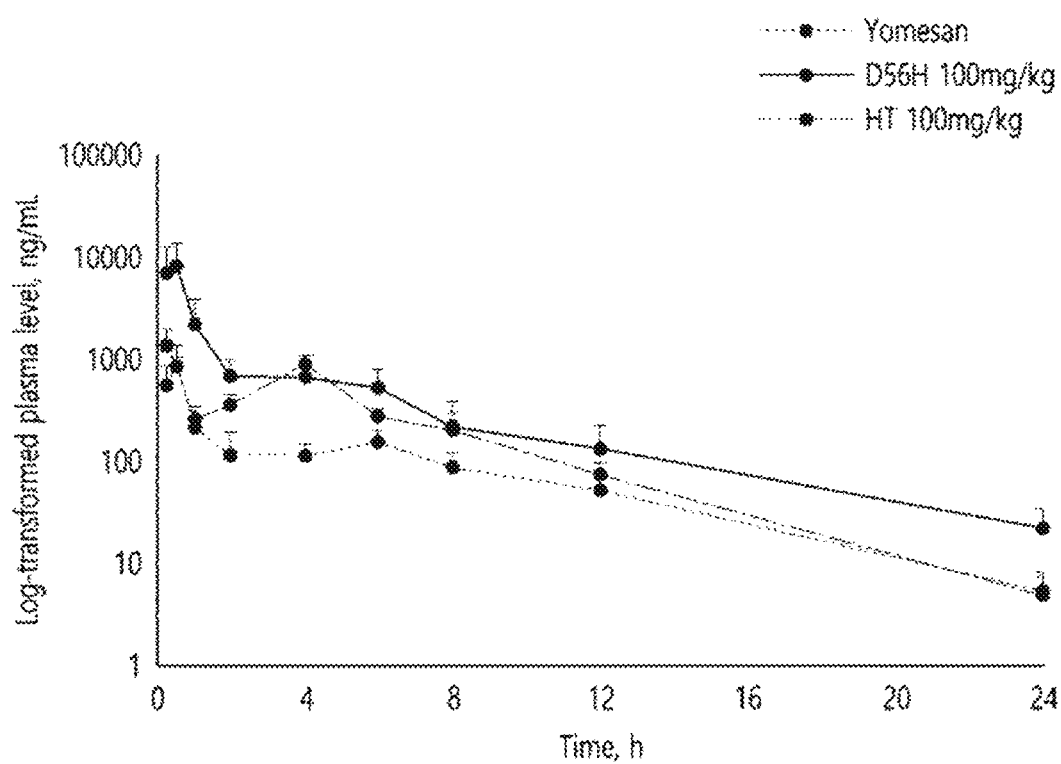

FIG. 32 illustrates a graph of the results of the patterns of drug concentration in blood following single oral administration of the compositions of Yomesan (NIC), Reference Examples 13 and Example 12 to rats at a dose of 100 mg/kg. According to FIG. 32, it can be confirmed that the composition of Example 12 has significantly higher $C_{max}$ values and AUC values, and it was confirmed that the composition of Example 12 had $C_{max}$ values higher than 9.3 times and AUC values 5.8 times higher than those of Yomesan, and AUC values 2.1 times higher than and $C_{max}$ values 5.4 times higher than those of Reference Example 13 in which the simple HT-NIC composite was coated with HPMC.

Figure 33:
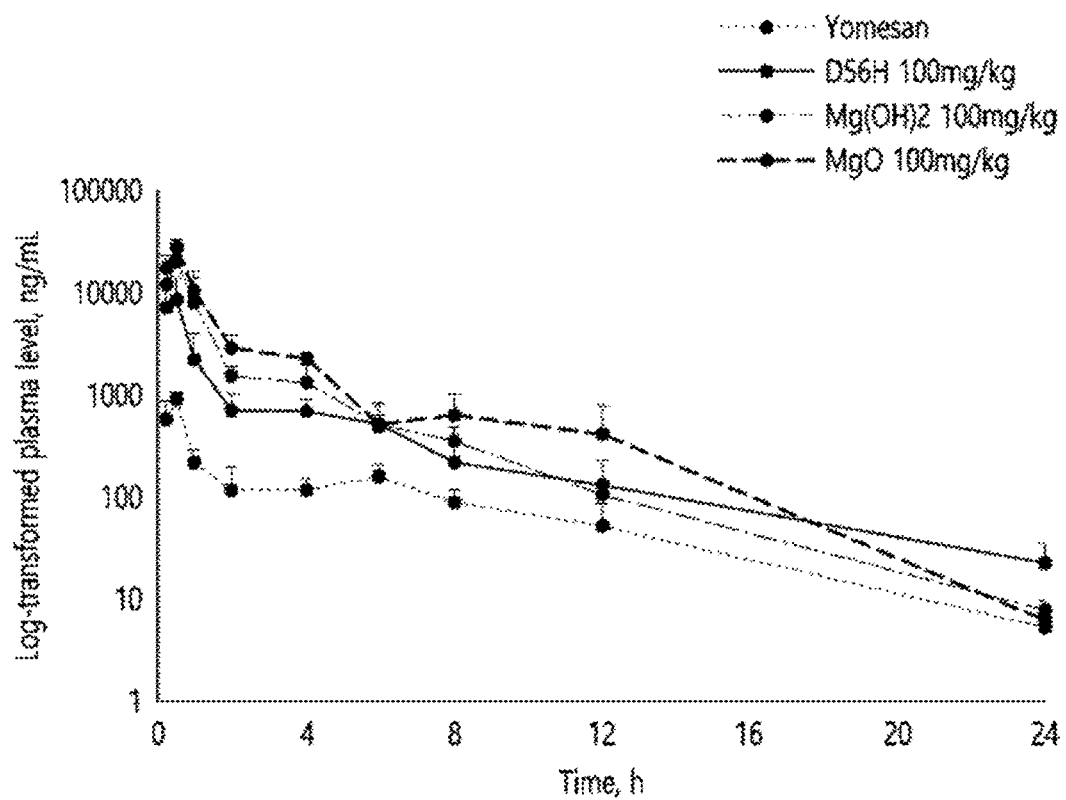

FIG. 33 illustrates a graph of the results of the patterns of drug concentration in blood following single oral administration of a 100 mg/kg dose of a calcined metal (hydr) oxide and a metal oxide, and NIC composite to rats, in addition to DHT. It was confirmed that the calcined $Mg(OH)_2$ and MgO and NIC composites of Examples 12-1 and 13 also significantly increased bioavailability due to the calcination process. In the case of Example 12, it was confirmed that an AUC increase rate of about 11 times and a $C_{max}$ increase rate of about 20.5 times higher than to Yomesan were shown, and in the case of Example 13, an AUC increase rate of about 16.8 times and a $C_{max}$ increase rate of about 25 times higher than Yomesan were shown.

Figure 34:
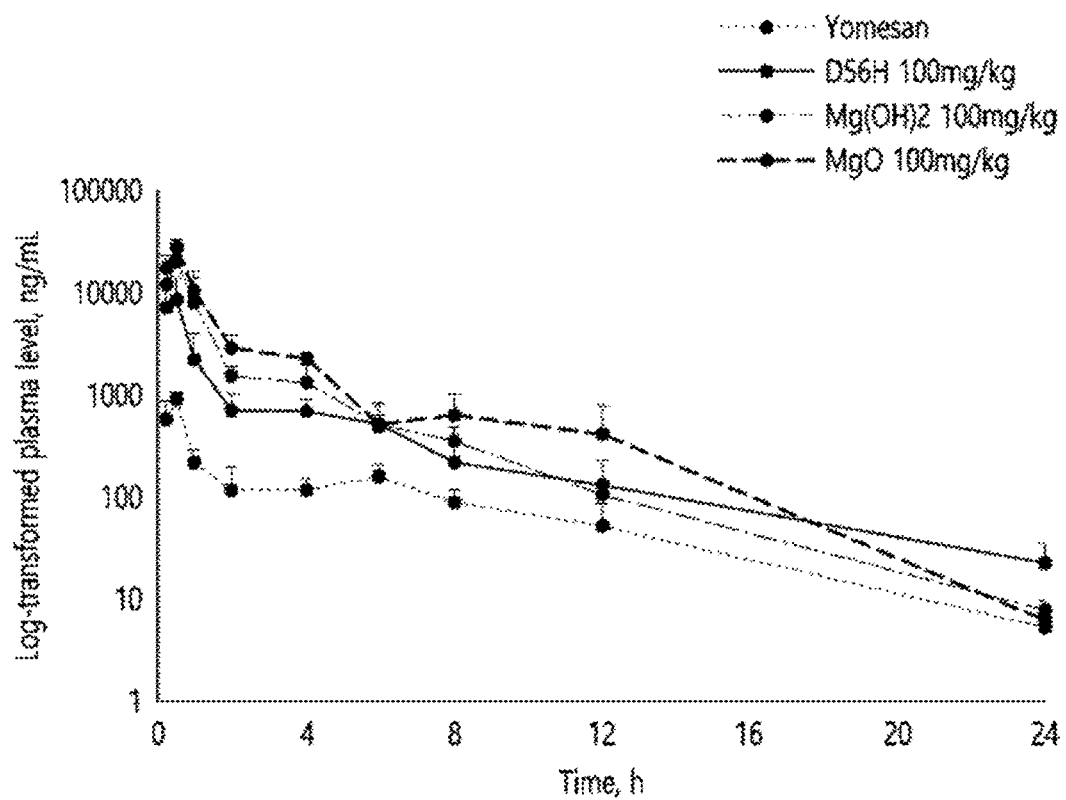

FIG. 34 illustrates a graph of the results of the patterns of drug concentration in blood following single oral administration of the pharmaceutical composition containing the DHT-NIC composite of Example 19 using the anhydrous organic solvent synthesis method and the pharmaceutical composition containing the DHT-NIC composite, which is prepared by the step of mechanochemical synthesizing, at a dose of 100 mg/kg. As can be seen in FIG. 34, it was confirmed that the pharmaceutical composition by the anhydrous organic solvent synthesis method and the mechanochemical synthesis method had a similar effect.

FIG. 39 illustrates a graph relevant to the results of bioavailability change when a compound was used by forming a metal (hydr)oxide composite, or a compound itself was formulated using a surfactant, etc., during preparing a pharmaceutical composition. As confirmed in FIG. 39, in case of Comparative Example 5 not using MgO, it could be confirmed that bioavailability was rapidly reduced, and with the decrease of the MgO content, the bioavailability was somewhat reduced. Specifically, it could be confirmed that the bioavailability of Example 22 when the ratio of niclosamide, MgO and surfactant was (1:2:2), was the best.

The rapid systemic circulation of NIC with improved bioavailability, which can be confirmed from the above results, suggests that it can be a particularly effective treatment strategy against SARS-CoV-2 virus in the early and asymptomatic stages.

The present inventors hypothesize that administration of a composition consisting of metal (hydr)oxide-NIC composite/surfactant could enhance bioavailability by circumventing or altering rapid intestinal or hepatic metabolism by cytochrome-P450 enzymes. It has already been reported that NIC is rapidly metabolized in the liver, and when orally administered, most of the NIC is removed as it changes to NIC-glucuronic acid.

Therefore, the rational molecular engineering strategy of attaching NIC to metal (hydr)oxide to form a composite performed in this study could further improve mucosal adhesions, which could help the NIC to be maintained up to the lymphatic system. This made it possible to achieve high plasma concentrations even after a single oral administration, and these results should be emphasized. To the best of our knowledge, the current study is the first to elucidate the pharmacokinetics of an orally administrable formulation of NIC capable of maintaining the NIC at plasma concentrations in excess of the $IC_{50}$ for 8 hours.

In addition, considering the medical application of the composition consisting of the calcined metal (hydr)oxide-NIC composite/surfactant of the present invention described above, when it is assumed that most orally administered drugs enter the systemic circulation, the composition described above could also achieve the maximum therapeutic NIC concentration in excess of $IC_{100}$. Interestingly, it can be confirmed that the composition containing the calcined metal (hydr)oxide-NIC composite/surfactant prepared as described above was able to maintain therapeutic concentrations in plasma for up to 8 hours (see FIG. 25, FIG. 39 and FIG. 40).

Experimental Example 9: In-Vivo Pharmacokinetic Analysis of Pharmaceutical Composition Containing Niclosamide Composite According to Metal (Hydr)Oxide Content To confirm the influence of the metal (hydr)oxide content in-vivo pharmacokinetics, an experiment for confirming AUC value changes according to MgO contents was designed. In-vivo pharmacokinetic analysis was performed using a MgO-NIC composite. Examples of changing the MgO content while forming pharmaceutical compositions (forms of Examples 5 to 11, or Examples 20 to 24) using the MgO-NIC composite were prepared (see Examples 23-1 to 23-3). The experiment was performed by a single oral administration method to hamsters or rats, and after performing the method, plasma drug concentration information was obtained.

The experiment was performed by administering each of the compositions of Examples 23-1 to 23-3 at a dose of 30 mg/kg.

The analysis results are shown in FIG. 40. It could be confirmed that AUC effects were proportionally increased with the increase of the MgO content. From these results, it could be confirmed that MgO plays a very important role in improving bioavailability.

Experimental Example 10: In-Vivo Pharmacokinetic Analysis of Pharmaceutical Composition Containing Metal (Hydr) Oxide-Docetaxel Composite In-vivo pharmacokinetic analysis was performed using a pharmaceutical composition including the DHT-docetaxel composite. The in-vivo pharmacokinetic analysis was proceeded in a way of performing a single oral administration of a pharmaceutical composition including the DHT-docetaxel composite to hamsters or rats, and plasma drug concentration information was obtained after proceeding the single oral administration in this way. The in-vivo pharmacokinetic study was proceeded by coating a pharmaceutical composition containing the DHT-docetaxel composite with HPMC, and forming docetaxel (DTX) as orally administrable compositions (Examples 14 and 16).

Figure 35:
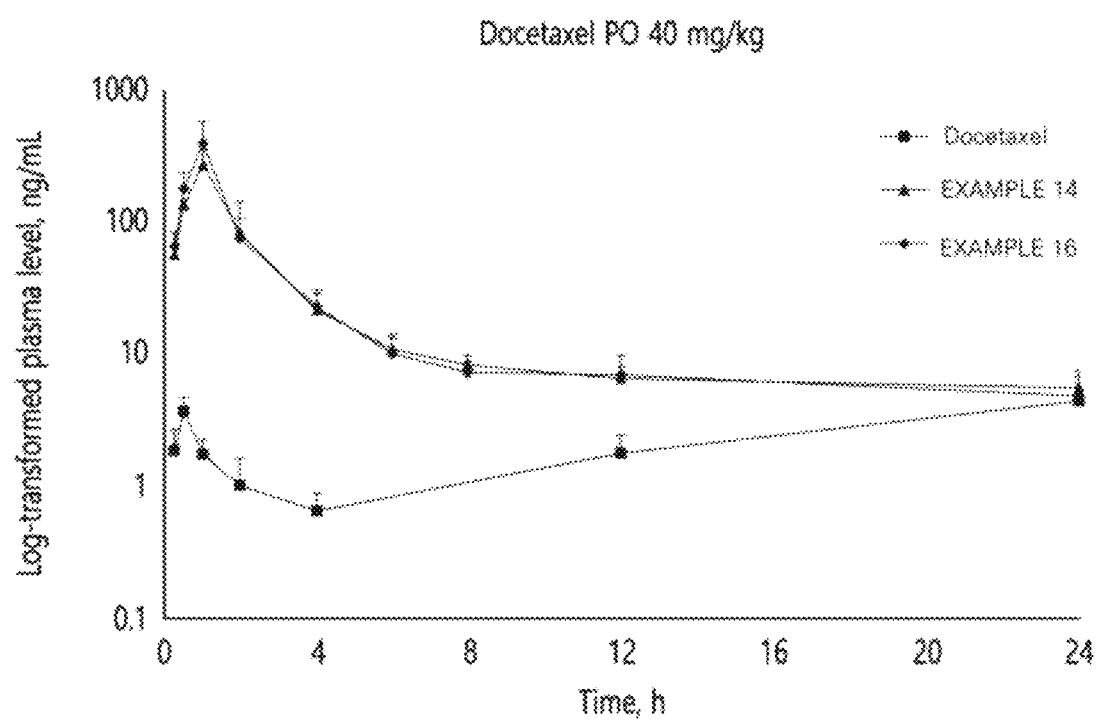
Figure 36:
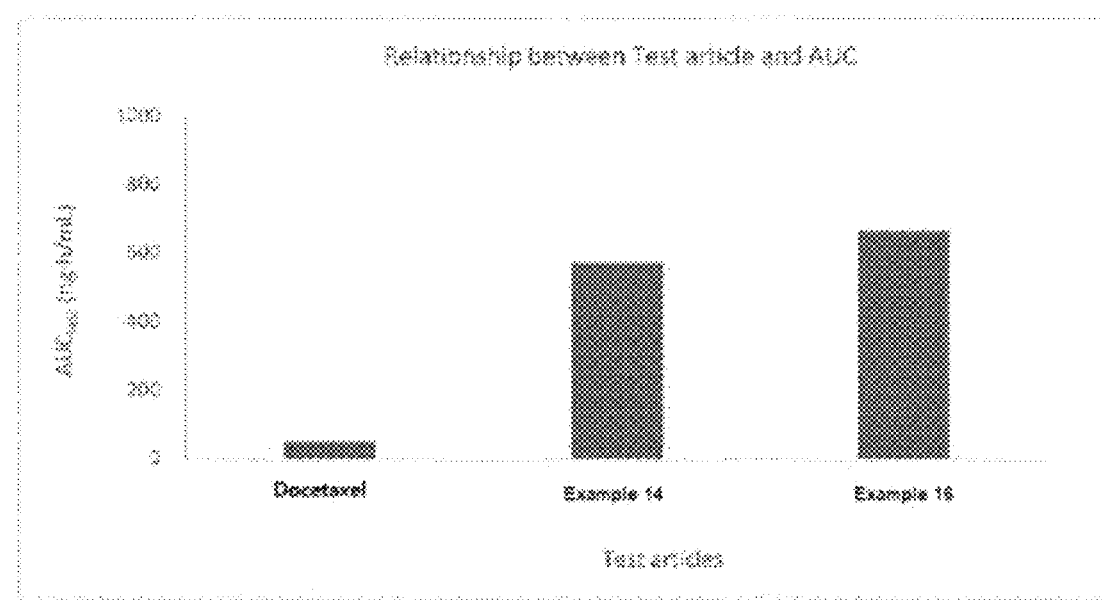
FIG. 36 illustrates a graph of AUC results for docetaxel, Example 14, and Example 16.

In addition, each of the compositions of Examples 14 and 16 was dissolved in a 5% Tween solution by a solution amount of 10 mL/kg at a dose of 40 mg/kg and administered orally once, and the results are illustrated in FIGS. 35 and 36, and specific data values are listed in Table 9 below.

TABLE 9

| | Docetaxel PO 40 mg/kg | | |
|---|---|---|---|
| PK Parameters | Docetaxel | Example 14 | Example 16 |
| AUC (last) | 47.46 | 571.89 | 663.25 |
| Cmax | 5.26 | 268.41 | 388.72 |
| Tmax | 0.50 | 1.00 | 1.00 |
| $T_{1/2}$ | 9.41 | 24.33 | 17.41 |

The control group was administered only docetaxel without additional formulation at a dose of 40 mg/kg, and it could be confirmed that when the pharmaceutical compositions of Examples 14 and 16 of the present invention were administered, the bioavailability increased by 10 times or more compared to the control group when docetaxel was simply administered. As can be seen from the results of Table 9, docetaxel has low bioavailability when administered orally. It was confirmed that, in the oral administration experiment using rats, the AUC of docetaxel was 47.46 and $C_{max}$ was 5.25, but when organic-inorganic hybrid technology was applied as in Examples 14 and 16, the AUC increased by 12 times and 14 times, respectively, and the $C_{max}$ increased by 51 times and 74 times, respectively. Therefore, it was confirmed, for the docetaxel which was difficult to develop as the oral dosage form due to its low bioavailability, that the bioavailability could be dramatically increased by applying the organic-inorganic hybrid technology.

Experimental Example 11: In-Vivo Pharmacokinetic Analysis of Pharmaceutical Composition of Metal (Hydr)Oxide Including a Compound Having Solubility in Water of 0.01 or Higher and/or not Including Hydroxyl Group In-vivo pharmacokinetic analysis was performed using the compound itself and pharmaceutical compositions prepared by forming metal (hydr)oxide composites (Comparative Examples 2 to 4).

The experiment was performed in a manner of a single oral administration of 5-FU, lipoic acid, artesunate, and the pharmaceutical compositions of Comparative Example 2, Comparative Example 3 and Comparative Example 4, to hamsters or rats, and after performing the method, plasma drug concentration information was obtained.

Figure 41:
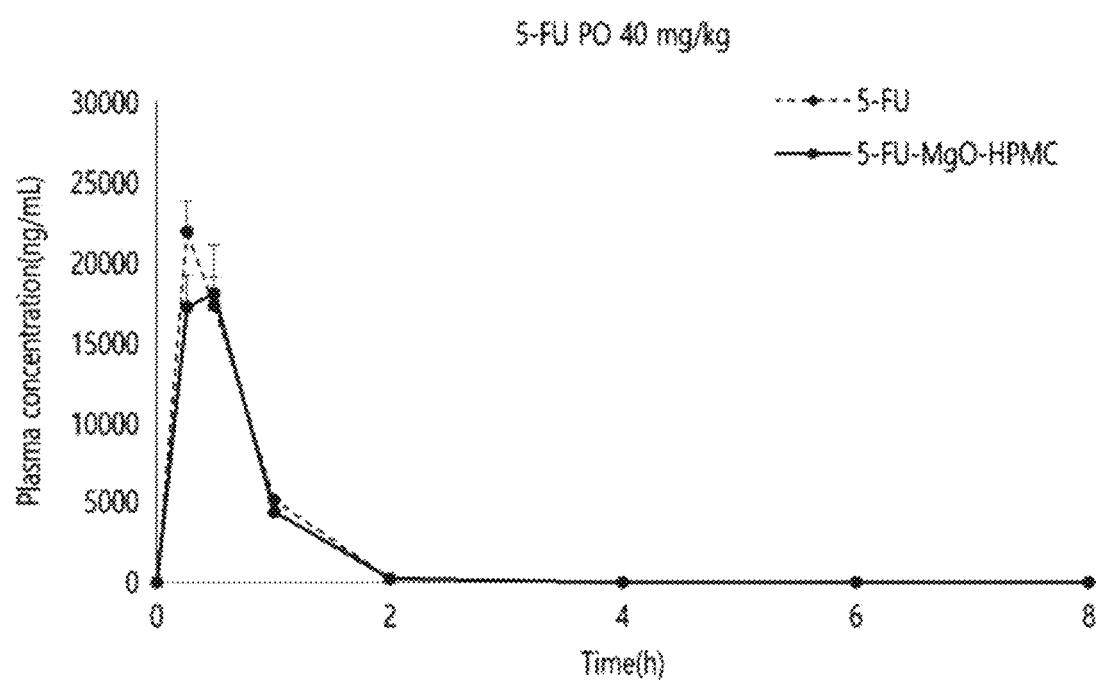
FIG. 41 illustrates a graph for drug concentration in plasma over time for a control group (simple 5-FU) and Comparative Example 2 (5-FU:MgO:HPMC).
Figure 42:
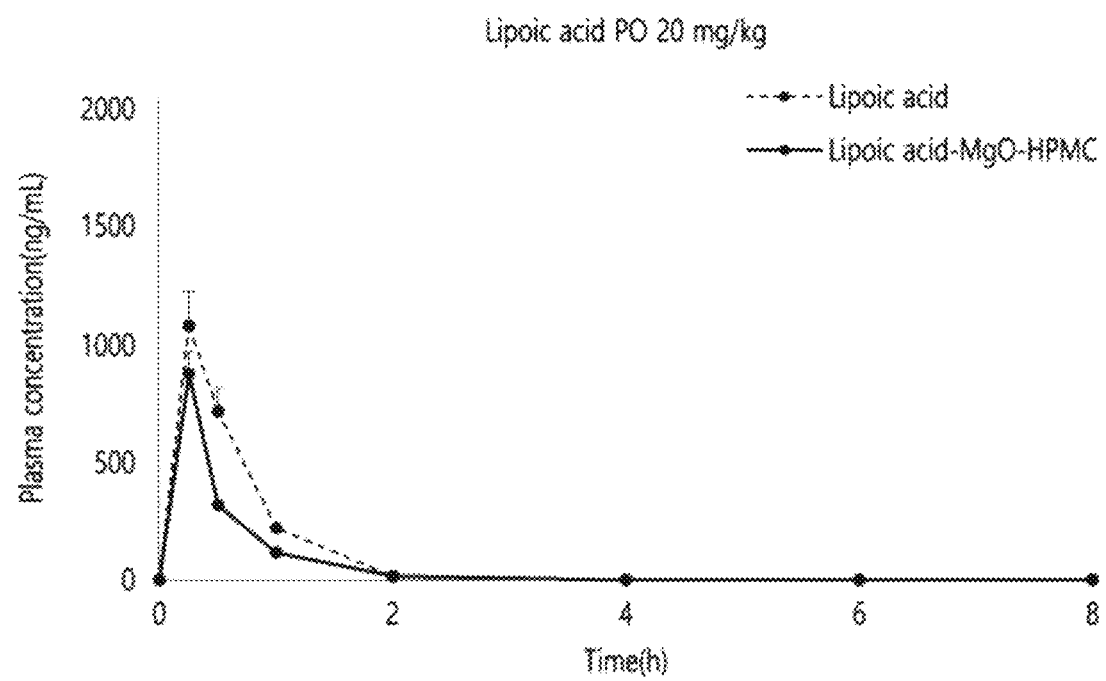
FIG. 42 illustrates a graph for drug concentration in plasma over time for a control group (simple lipoic acid) and Comparative Example 3 (lipoic acid:MgO:HPMC).
Figure 43:
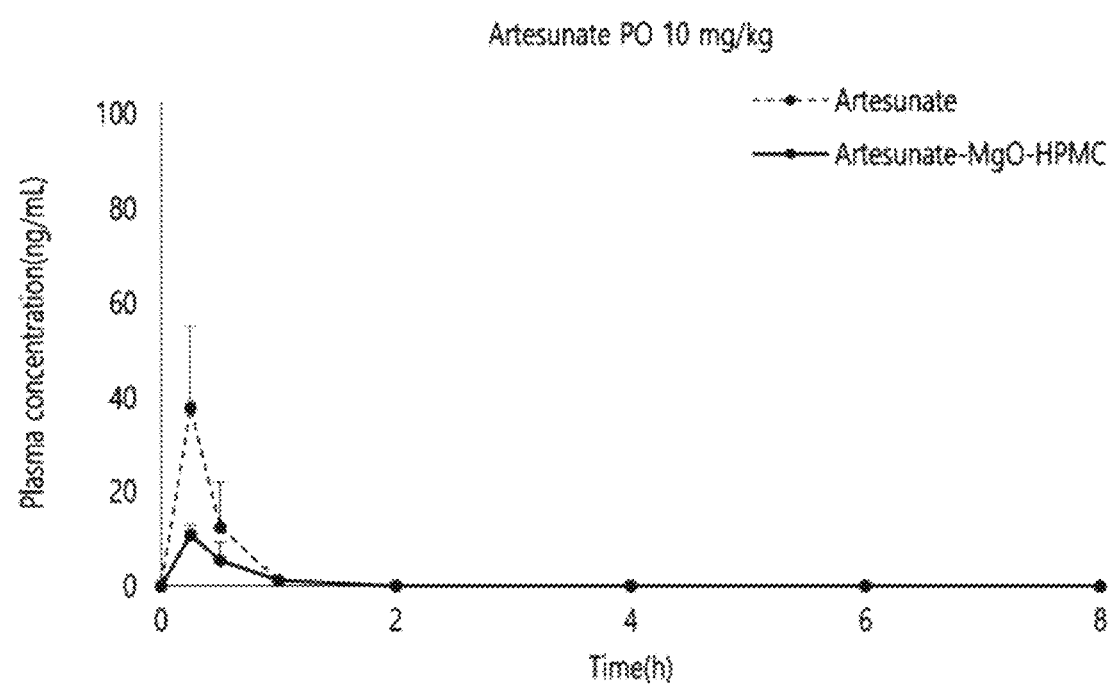
FIG. 43 illustrates a graph for drug concentration in plasma over time for a control group (simple artesunate) and Comparative Example 4 (artesunate:MgO:HPMC).
Figure 44:
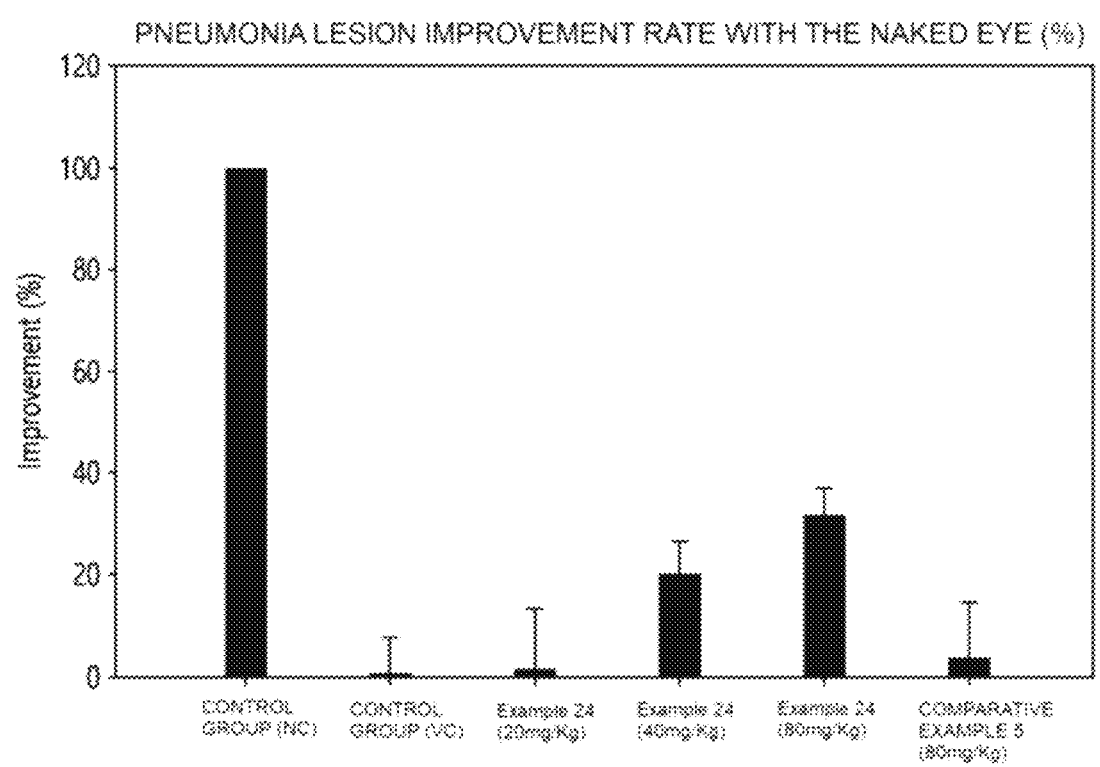
FIG. 44 illustrates a graph for pneumonia lesion improvement rate seen with the naked eye for a virus-uninfected control group (NC), a virus-infected control group (VC), and groups administering 20 mg/Kg, 40 mg/Kg, and 80 mg/Kg of the pharmaceutical composition of Example 24, and 80 mg/Kg of the composition of Comparative Example 5, to virus-infected hamsters.

In addition, the experiment was performed by administering the compound and the pharmaceutical compositions of Comparative Examples 2 to 4 at a dose of 40 mg/kg, respectively, and the results are shown in FIG. 41 to FIG. 43.

The control group corresponds to administering each of 5-FU, lipoic acid and artesunate without additional formulation at a dose of 40 mg/kg, and in the cases of 5-FU, lipoic acid and artesunate, it could be confirmed that bioavailability of the compounds was not improved due to the chemical structure or solubility properties in water, though metal (hydr)oxide composites were prepared using MgO.

Experimental Example 12: Drug Release Experiment

Drug release experiment was proceeded at 37° C. using 500 mL of artificial intestinal fluid (pH 6.8) with 2% Tween 60 added. Experiments were proceeded using Example 6

(D56H), Example 12-1 (Mg(OH)$_2$), Example 13 (MgO), Reference Example 13 (HT), and Comparative Example 1 (Yomesan).

Figure 37:
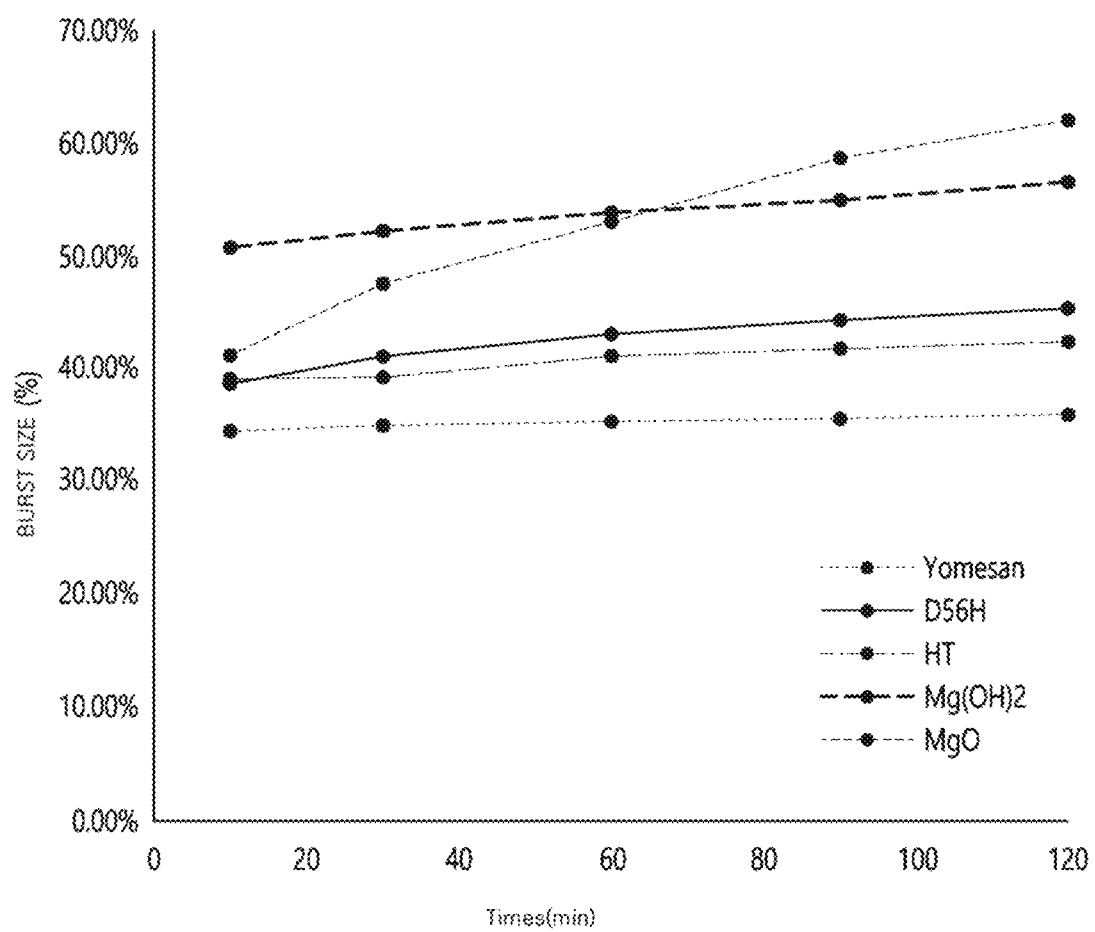
FIG. 37 illustrates a graph for results of release rates of Example 6 (D56H), Example 12-3 (Mg(OH)$_2$), Example 13-2 (MgO), Comparative Example 4 (HT), and Comparative Example 1 (Yomesan).

Referring to FIG. 37, it can be seen that the release rate of the NIC loaded on the metal (hydr)oxide is higher than that of Yomesan, and it could be confirmed that the release rate of the NIC loaded on the calcined metal (hydr)oxide was further increased compared to Reference Example 13.

From the drug release results, it can be confirmed that the bioavailability of the poorly soluble drug becomes higher when the metal (hydr)oxide composite of the present invention is used.

Experimental Example 13: Antiviral Efficacy Test

Figure 38:
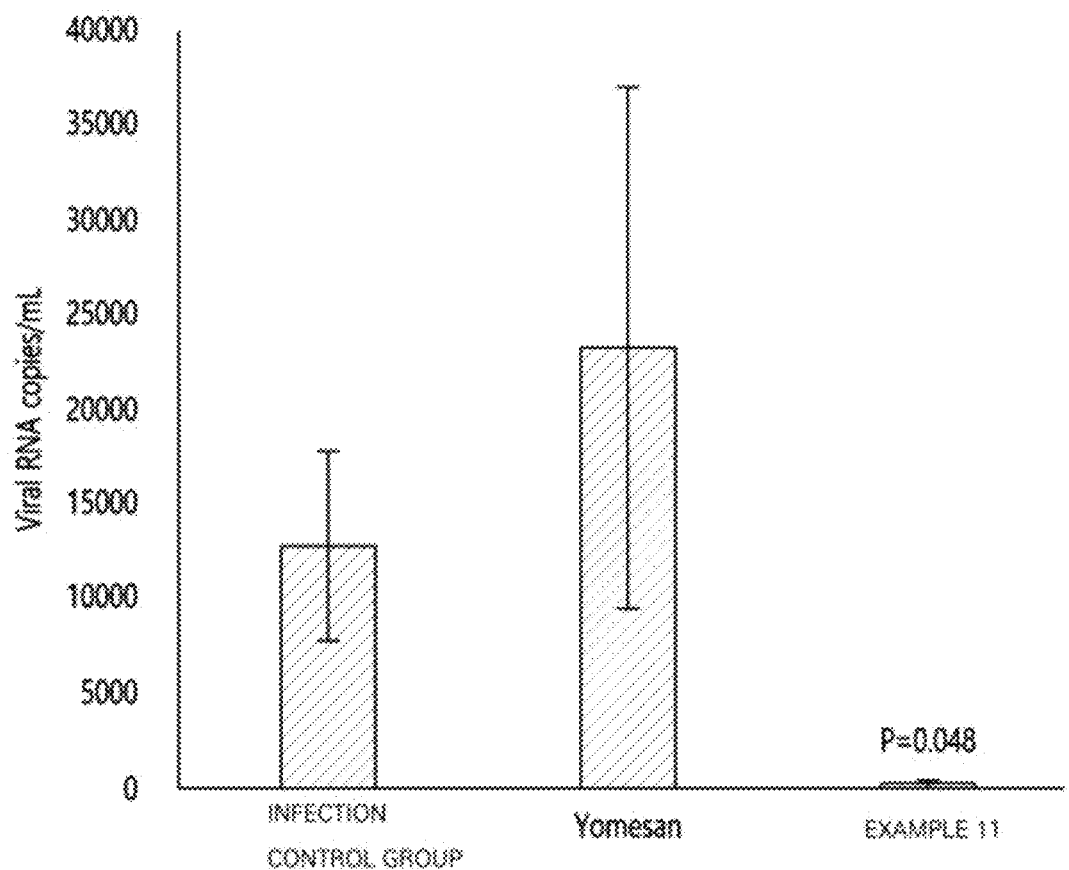
FIG. 38 illustrates a graph of virus killing results for an infection control group, Yomesan, and Example 11.

Test Model: Golden Syrian Hamster
Administered drug: D24T (CP-COV03)
Drug dose: 25 mg/kg
Dosage volume: 20 mL/kg The composition of Example 11 was orally administered to a hamster infected with the Corona 19 virus (SARS-CoV2) every 4 hours from the day after infection. As a result of RT-qPCR analysis of blood collected from the hamster on the second day of infection (one day after administration), it was confirmed that the viral RNA concentration in blood was significantly (ANOVA, P<0.05) reduced compared to the infection control group (untreated group) (see FIG. 38). On the other hand, it was confirmed that the group administered 25 mg/kg of Yomesan of Comparative Example 1 did not reduce the viral concentration in blood due to low bioavailability (see FIG. 38).

Experimental Example 14: Antiviral efficacy test

Test Model: Golden Syrian Hamster
Administered drug: Example 24
Drug dose: 20, 40 and 80 mg/kg
Dosage volume: 20 mL/kg In the case of the composition of Example 24, the administration dose was based on each of the drug dosage, and in the case of the composition of Comparative Example 5, the drug was administered with a dose of 80 mg/Kg with an interval of 12 hours after 6 hours from the infection by corona 19 virus (SARS-CoV2), and at day 4 from the infection, a model was dissected. After dissecting a hamster, observation on lung with the naked eye, observation on lung tissue lesions, viral load measurement, etc. were performed, and the results are shown in FIG. 44 to FIG. 48.

If pneumonia progresses by the infection of SARS-CoV-2, lung lesions occur. When compared to uninfected hamster control group (NC: negative control) and infected hamster control group (VC: vehicle control), the number of lung lesions of the uninfected hamster was calculated as 100, and the number of lung lesions of the infected hamster was calculated as 1. In the case of Comparative Example 5, the improvement rate of lung lesions was just 4.1% though 80 mg/kg was administered. Meanwhile, in the case of Example 24, the improvement rate of lung lesions was increased according to the increase of CP-COV03 dose, and it was confirmed that the lung lesions was improved by 31.6% with 80 mg/kg (see FIG. 44).

Figure 45:
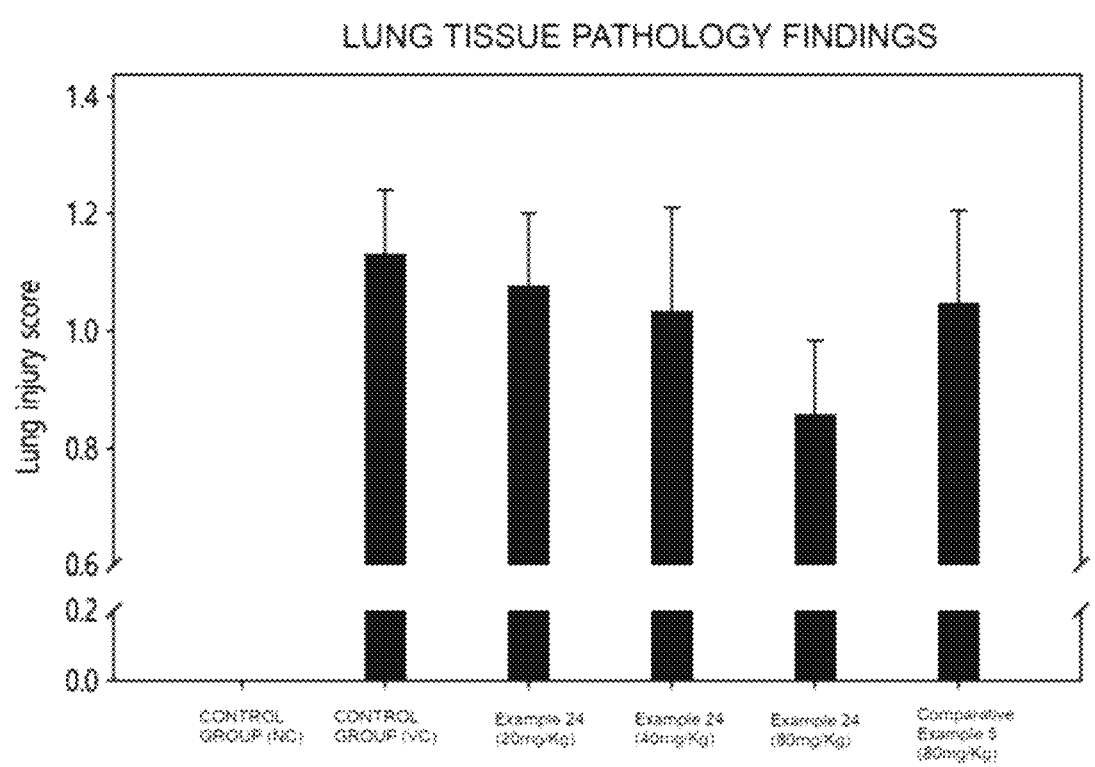
FIG. 45 illustrates a graph for lung tissue pathology findings for a virus-uninfected control group (NC), a virus-infected control group (VC), and groups administering 20 mg/Kg, 40 mg/Kg, and 80 mg/Kg of the pharmaceutical composition of Example 24, and 80 mg/Kg of the composition of Comparative Example 5, to virus-infected hamsters.

In addition, lung tissues removed by dissection were fixed and stained, and injury score according to detailed observation and pathological findings was computed and shown in FIG. 45. In the case of the infected hamster (VC), lung injury score was 1.13, and in the case of Comparative Example 5, though 80 mg/kg was administered, the injury score was not improved significantly (lowered) (injury score: 1.05). Meanwhile, in the case of Example 24, the injury score was lowered according to the increase of the dose, and specifically, if 80 mg/kg was administered, the injury score was lowered to 0.86, and significantly improved effects were confirmed (see FIG. 45).

Figure 46:
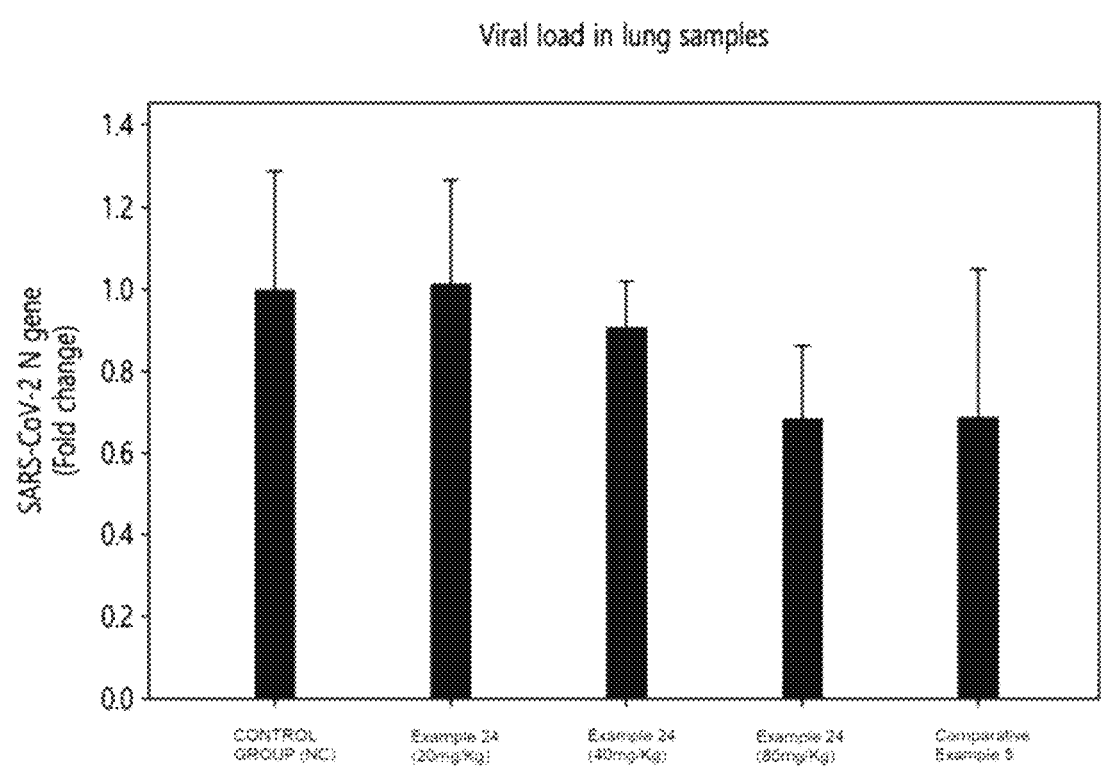
FIG. 46 illustrates a graph for viral load in lung sample for a virus-infected control group (VC), and groups administering 20 mg/Kg, 40 mg/Kg, and 80 mg/Kg of the pharmaceutical composition of Example 24, and 80 mg/Kg of the composition of Comparative Example 5, to virus-infected hamsters.
Figure 47:
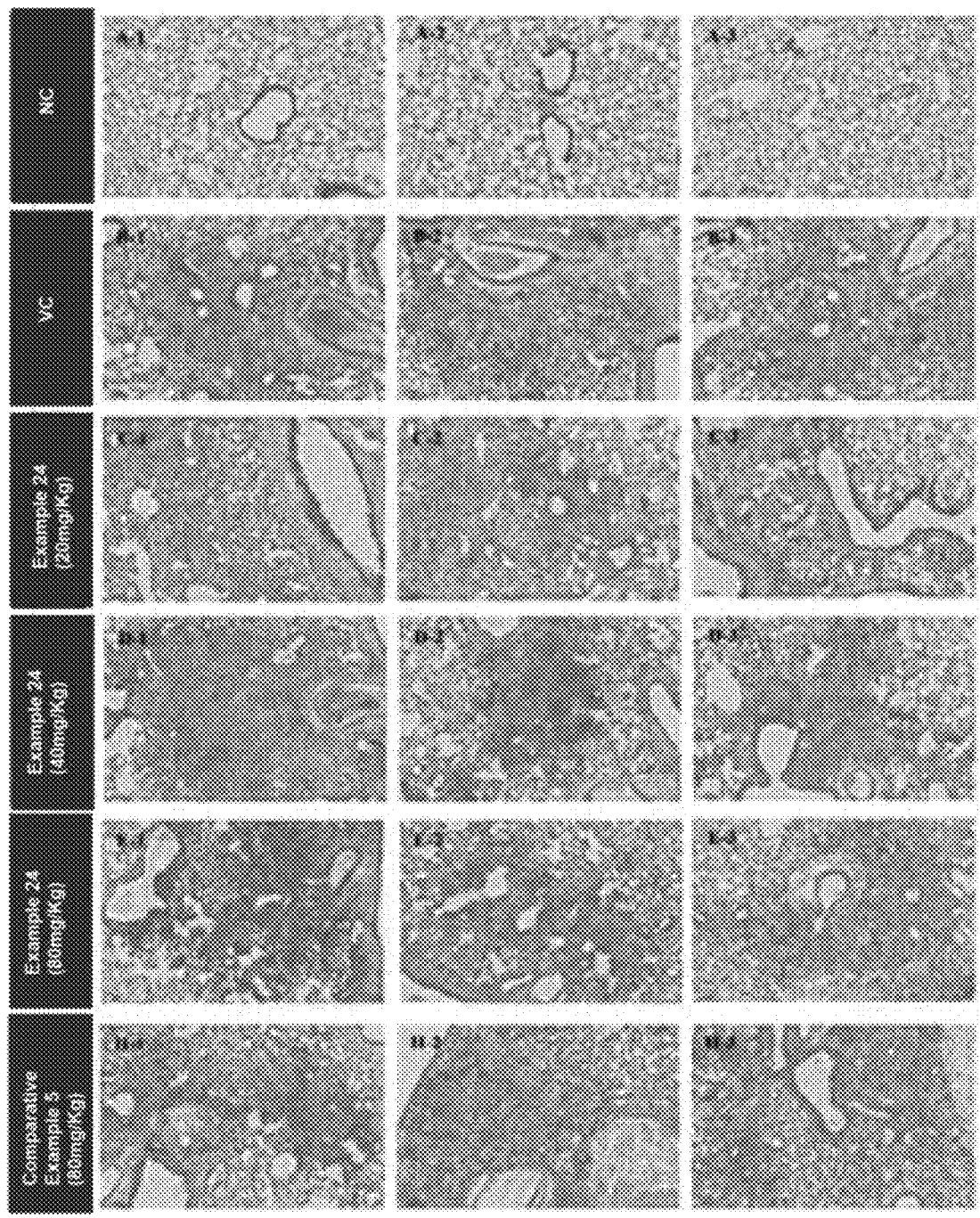
FIG. 47 illustrates cell pictures that serve the basis of lung tissue pathology findings for a virus-uninfected control group (NC), a virus-infected control group (VC), and groups administering 20 mg/Kg, 40 mg/Kg, and 80 mg/Kg of the pharmaceutical composition of Example 24, and 80 mg/Kg of the composition of Comparative Example 5, to virus-infected hamsters.

Finally, the viral load in lung tissues was quantified with RT-qPCR, and the results are shown in FIG. 46. The viral load of the administration group administering Comparative Example 5, showed a large deviation, and when compared to the control group (VC), the reduction of the viral load or not was uncertain. Meanwhile, in the case of Example 24, distinct antiviral activity was shown, and the viral load was reduced according to the increase of the dose (see FIG. 46).

The invention claimed is:
1. A metal (hydr)oxide composite comprising:
a metal (hydr)oxide; and
a compound comprising at least one or more hydroxyl groups in the compound or a salt thereof,
wherein the metal (hydr)oxide is one or more selected from the compounds represented by the following Chemical Formulas 3 to 5:

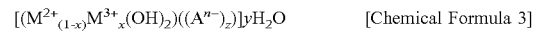
$$[(M^{2+}_{(1-x)}M^{3+}_x(OH)_2)((A^{n-})_z)]yH_2O \qquad \text{[Chemical Formula 3]}$$

(in Chemical Formula 3,
$M^{2+}$ is a divalent metal cation selected from the group consisting of $Mg^{2+}$, $Ni^{2+}$, $Cu^{2+}$, $Co^{2+}$, and $Zn^{2+}$,
$M^{3+}$ is a trivalent metal cation selected from the group consisting of $Al^{3+}Fe^{3+}V^{3+}$, $Ti^{3+}$, $Mn^{3+}$, and $Ga^{3+}$,
x is a number having a range of greater than 0 and less than or equal to 0.5,
A is an anion selected from the group consisting of $CO_3^{2-}$, $NO_3^-$, $Br^-$, $Cl^-$, $SO_4^{2-}$, $HPO_4^{2}$ and $F^-$,
n is a charge number of the anion A,
n is a number having a range of 0.5 or more and 2 or less,
z is a number having a range of 0 or more and 1 or less, and
y is a positive number greater than 0),

$$[(M^{2+}(OH)_{2-x})((A^{n-})_z)]yH_2O \qquad \text{[Chemical Formula 4]}$$

(in Chemical Formula 4,
$M^{2+}$ is a divalent metal cation selected from the group consisting of $Mg^{2+}$, $Ni^{2+}$, $Cu^{2+}$, $Co^{2+}$, and $Zn^{2+}$,
x is a number having a range of 0 or more and 0.4 or less,
A is an anion selected from the group consisting of $CO_3^{2-}$, $NO_3^-$, $Br^-$, $Cl^-$, $SO_4^{2-}$, $HPO_4^{2-}$ and $F^-$,
n is a charge number of anion A,
n is a number having a range of 0 or more and 2 or less,
z is a number having a range of 0 or more and 1 or less, and
y is a positive number greater than 0), and

$$[(M^{2+}(O)_{2-x})((A^{n-})_z)]yH_2O \qquad \text{[Chemical Formula 5]}$$

(in Chemical Formula 5,
$M^{2+}$ is $Mg^{2+}$, $Ni^{2+}$, $Cu^{2+}$, or $Zn^{2+}$,
x is a number of 1 or more and less than 2,
A is an anion selected from the group consisting of $CO_3^{2-}$, $NO_3^-$, $Br^-$, $Cl^-$, $SO_4^{2-}$, $HPO_4^{2-}$, and $F^-$,
n is a charge number of the anion A,
n is a number having a range of 0 or more and 2 or less,
z is a number having a range of 0 or more and 1 or less, and
y is a positive number greater than 0),
wherein the compound comprising at least one or more hydroxyl groups in the compound, is one or more compounds selected from the compounds represented by the following Chemical Formula 1 or Chemical Formula 2:

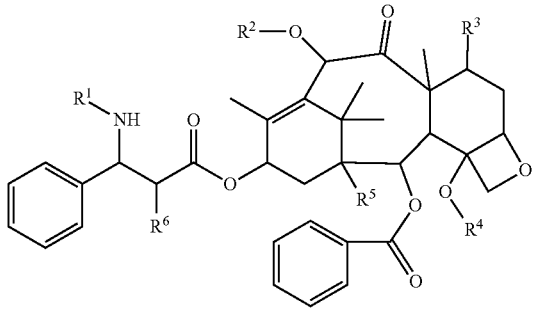

(in Chemical Formula 1,
R1 to R6 are each independently a hydrogen atom, a halogen atom, a hydroxyl group, an alkoxy group, an ester group, an acyl group, an aromatic ring or a nitro group, and
at least one or more among R1 to R6 are hydroxyl groups),

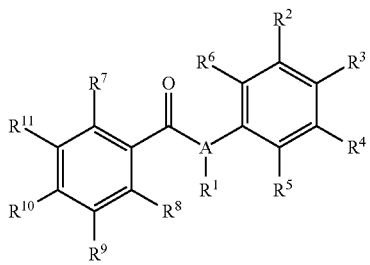

(in Chemical Formula 2,
A is a nitrogen atom or an oxygen atom,
if A is a nitrogen atom, $R^1$ may be a hydrogen atom, a halogen atom, a hydroxyl group, or an alkyl group, and if A is an oxygen atom, $R^1$ does not have a substituent,
$R^2$ to $R^{11}$ are each independently a hydrogen atom, a halogen atom, a hydroxyl group, a methoxy group, an ester group, an acyl group, or a nitro group, and
at least one or more among $R^1$ to $R^{11}$ are hydroxyl groups).

2. The metal (hydr)oxide composite of claim 1, wherein the compound comprising at least one or more hydroxyl groups in the compound or a salt thereof, has a solubility in water of less than 0.01 mM.

3. The metal (hydr)oxide composite of claim 1, wherein the compound comprising at least one or more hydroxyl groups in the compound or a salt thereof, comprises one or more selected from niclosamide, oxyclozanide, docetaxel, paclitaxel.

4. The metal (hydr)oxide composite of claim 1, wherein the metal (hydr)oxide composite is for preventing or treating any one or more diseases among viral infectious diseases, inflammatory diseases and malignant tumor diseases.

5. A pharmaceutical composition comprising: a metal (hydr)oxide; a compound comprising at least one or more hydroxyl groups in the compound or a salt thereof, and an additive, wherein the metal (hydr)oxide is one or more selected from the compounds represented by the following Chemical Formulas 3 to 5:

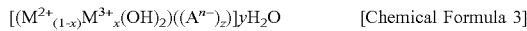  [Chemical Formula 3]

(in Chemical Formula 3,
$M^{2+}$ is a divalent metal cation selected from the group consisting of $Mg^{2+}$, $Ni^{2+}$, $Cu^{2+}$, $Co^{2+}$, and $Zn^{2+}$,
$M^{3+}$ is a trivalent metal cation selected from the group consisting of $Al^{3+}$ $Fe^{3+}$ $V^{3-}$, $Ti^{3+}$, $Mn^{3+}$, and $Ga^{3+}$,
x is a number having a range of greater than 0 and less than or equal to 0.5,
A is an anion selected from the group consisting of $CO_3^{2-}$, $NO_3^-$, $Br^-$, $Cl^-$, $SO_4^{2-}$, $HPO_4^{2-}$ and $F^-$,
n is a charge number of the anion A,
n is a number having a range of 0.5 or more and 2 or less,
z is a number having a range of 0 or more and 1 or less, and
y is a positive number greater than 0),

  [Chemical Formula 4]

(in Chemical Formula 4,
$M^{2+}$ is a divalent metal cation selected from the group consisting of $Mg^{2+}$, $Ni^{2+}$, $Cu^{2+}$, $Co^{2+}$, and $Zn^{2+}$,
x is a number having a range of 0 or more and 0.4 or less,
A is an anion selected from the group consisting of $CO_3^{2-}$, $NO_3^-$, $Br^-$, $Cl^-$, $SO_4^{2-}$, $HPO_4^{2-}$, and $F^-$,
n is a charge number of anion A,
n is a number having a range of 0 or more and 2 or less,
z is a number having a range of 0 or more and 1 or less, and
y is a positive number greater than 0), and

  [Chemical Formula 5]

(in Chemical Formula 5,
$M^{2+}$ is $Mg^{2+}$, $Ni^{2+}$, $Cu^{2+}$, or $Zn^{2+}$,
x is a number of 1 or more and less than 2,
A is an anion selected from the group consisting of $CO_3^{2-}$, $NO_3^-$, $Br^-$, $Cl^-$, $SO_4^{2-}$, $HPO_4^{2-}$ and $F^-$,
n is a charge number of the anion A,
n is a number having a range of 0 or more and 2 or less,
z is a number having a range of 0 or more and 1 or less, and
y is a positive number greater than 0),
wherein the compound comprising at least one or more hydroxyl groups in the compound or a salt thereof, is one or more compounds selected from the compounds represented by the following Chemical Formula 1 or Chemical Formula 2:

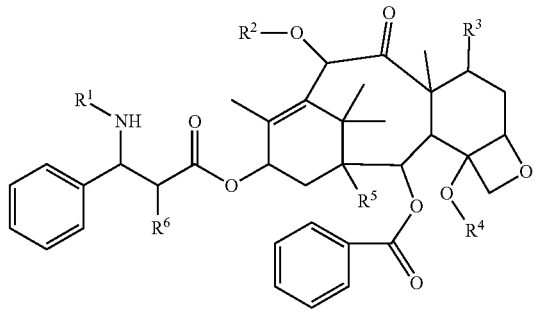

(in Chemical Formula 1,
R1 to R6 are each independently a hydrogen atom, a halogen atom, a hydroxyl group, an alkoxy group, an ester group, an acyl group, an aromatic ring or a nitro group, and at least one or more among R1 to R6 are hydroxyl groups),

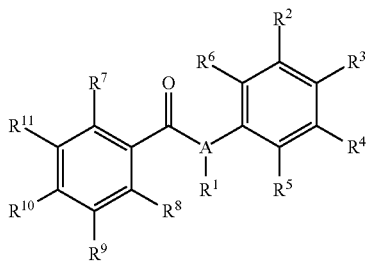

(in Chemical Formula 2,
A is a nitrogen atom or an oxygen atom,
if A is a nitrogen atom, R1 may be a hydrogen atom, a halogen atom, a hydroxyl group, or an alkyl group, and if A is an oxygen atom, R1 does not have a substituent,
R2 to R11 are each independently a hydrogen atom, a halogen atom, a hydroxyl group, a methoxy group, an ester group, an acyl group, or a nitro group, and
at least one or more among R1 to R11 are hydroxyl groups).

6. The pharmaceutical composition of claim 5,
wherein the compound comprising at least one or more hydroxyl groups in the compound or a salt thereof, comprises one or more selected from niclosamide, oxyclozanide, docetaxel, paclitaxel.

7. The pharmaceutical composition of claim 5,
wherein 10 to 60 wt % of the metal (hydr) oxide, 0.1 to 60 wt % of the compound or a salt thereof, and 10 to 80 wt % of the additive are comprised based on total 100 wt % of the pharmaceutical composition.

8. The pharmaceutical composition of claim 5,
wherein the additive is a surfactant.

9. The pharmaceutical composition of claim 5,
wherein the metal (hydr) oxide and the compound comprising at least one or more hydroxyl groups in the compound or a salt thereof, are comprised in a rate of 1:0.1 to 10.

10. The pharmaceutical composition of claim 5,
wherein the pharmaceutical composition is for preventing or treating any one or more diseases from viral infectious diseases, inflammatory diseases and malignant tumor diseases.

11. The pharmaceutical composition of claim 8,
wherein the surfactant is one or more selected from a polyoxyethylene sorbitan fatty acid ester-based surfactant, a poloxamer-based surfactant, a lecithin-based surfactant, a glycerol fatty acid ester-based surfactant, a sorbitan fatty acid ester-based surfactant, a polyethylene glycol (PEG)-based surfactant, a long chain of sugar, a gum-based surfactant, a gelling agent-based surfactant, a thickening polysaccharide-based surfactant and a sodium dodecyl sulfate.

12. The metal (hydr)oxide composite of claim 1, wherein the compound comprising at least one or more hydroxyl groups comprises niclosamide or docetaxel.

13. The metal (hydr)oxide composite of claim 1,
wherein the metal (hydr)oxide is the compounds represented by the Chemical Formula 5, and
wherein, in the Chemical Formula 5, $M^{2+}$ is $Mg^{2+}$.

14. The metal (hydr)oxide composite of claim 13,
wherein the compound comprising at least one or more hydroxyl groups in the compound or a salt thereof, comprises one or more selected from niclosamide, oxyclozanide, docetaxel, paclitaxel.

15. The pharmaceutical composition of claim 5, wherein the compound comprising at least one or more hydroxyl groups comprises niclosamide or docetaxel.

16. The pharmaceutical composition of claim 5,
wherein the metal (hydr)oxide is the compounds represented by the Chemical Formula 5, and
wherein, in the Chemical Formula 5, $M^{2+}$ is $Mg^{2+}$.

17. The pharmaceutical composition of claim 16,
wherein the compound comprising at least one or more hydroxyl groups in the compound or a salt thereof, comprises one or more selected from niclosamide, oxyclozanide, docetaxel, paclitaxel.

\* \* \* \* \*